(12) United States Patent
Eckert et al.

(10) Patent No.: US 10,010,488 B2
(45) Date of Patent: *Jul. 3, 2018

(54) DENTAL COMPOSITION AND USE THEREOF

(71) Applicant: 3M INNOVATIVE PROPERTIES COMPANY, St. Paul, MN (US)

(72) Inventors: Adrian S. Eckert, Herrsching (DE); Michael Cub, Munich (DE); Bettina Hailand, Ammersee (DE); Marion B. Kestel, Munich (DE); Christoph Thalacker, Wilheim (DE); Karsten Dede, Landsberg (DE)

(73) Assignee: 3M Innovative Properties Company, St. Paul, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/116,873

(22) PCT Filed: Feb. 10, 2015

(86) PCT No.: PCT/US2015/015160
§ 371 (c)(1),
(2) Date: Aug. 5, 2016

(87) PCT Pub. No.: WO2015/126666
PCT Pub. Date: Aug. 27, 2015

(65) Prior Publication Data
US 2017/0165152 A1    Jun. 15, 2017

(30) Foreign Application Priority Data

Feb. 18, 2014 (EP) .................................... 14155585

(51) Int. Cl.
| | | |
|---|---|---|
| C08F 2/46 | (2006.01) | |
| C08F 2/50 | (2006.01) | |
| C08G 61/04 | (2006.01) | |
| A61K 6/083 | (2006.01) | |
| A61K 6/00 | (2006.01) | |
| A61C 13/00 | (2006.01) | |

(52) U.S. Cl.
CPC ........ *A61K 6/0835* (2013.01); *A61C 13/0022* (2013.01); *A61K 6/0052* (2013.01); *A61K 6/0073* (2013.01); *A61K 6/0088* (2013.01)

(58) Field of Classification Search
CPC .............. A61K 6/00835; A61K 6/0073; A61K 6/0088; A61K 6/0052; A61C 13/022
USPC ............. 522/25, 7, 6, 1, 71, 189, 184; 520/1
See application file for complete search history.

(56) References Cited

U.S. PATENT DOCUMENTS

| | | |
|---|---|---|
| 3,347,954 A | 10/1967 | Bredereck |
| 3,541,068 A | 11/1970 | Taylor |
| 3,729,313 A | 4/1973 | Smith |
| 3,741,769 A | 6/1973 | Smith |
| 3,808,006 A | 4/1974 | Smith |
| 3,853,962 A | 12/1974 | Gander |
| 4,071,424 A | 1/1978 | Dart |
| 4,250,053 A | 2/1981 | Smith |
| 4,259,075 A | 3/1981 | Yamauchi |
| 4,394,403 A | 7/1983 | Smith |
| 4,443,587 A | 4/1984 | Schmitt |
| 4,499,251 A | 2/1985 | Omura |
| 4,537,940 A | 8/1985 | Omura |
| 4,539,382 A | 9/1985 | Omura |
| 4,544,742 A | 10/1985 | Schmitt |
| 4,642,126 A | 2/1987 | Zador |
| 4,652,274 A | 3/1987 | Boettcher |
| 4,744,827 A | 5/1988 | Winkel |
| 4,772,530 A | 9/1988 | Gottschalk |
| 4,872,936 A | 10/1989 | Engelbrecht |
| 4,874,450 A | 10/1989 | Gottschalk |
| 4,954,414 A | 9/1990 | Adair |
| 5,055,372 A | 10/1991 | Shanklin |
| 5,057,393 A | 10/1991 | Shanklin |

(Continued)

FOREIGN PATENT DOCUMENTS

| | | | |
|---|---|---|---|
| EP | 0455854 | 11/1991 | |
| EP | 0712622 | 5/1996 | |
| EP | 1051961 | 11/2000 | |
| EP | 1340472 | 9/2003 | |
| WO | WO-2008005173 A1 * | 1/2008 | ............... A61K 6/09 |
| WO | WO 2009-042574 | 4/2009 | |
| WO | WO 2009-151957 | 12/2009 | |
| WO | WO 2012-003136 | 1/2012 | |
| WO | WO 2013-082337 | 6/2013 | |

OTHER PUBLICATIONS

Houben-Weyl, Methoden Der Organischen Chemie, 55, (1965).
Houben-Weyl, Methoden Der Organischen Chemie, 59, (1965).
Sakaguchi, "Analysis of strain gage method for measurement of post-gel shrinkage in resin composites", Dental Materials, 1997, vol. 13, pp. 233-239.
International Search Report for PCT International Application No. PCT/US2015/015160, dated May 29, 2015, 4pgs.

*Primary Examiner* — Jessica Whiteley

(57) ABSTRACT

A dental composition comprising a polymerizable monomer (1), initiator, filler component(s) in an amount of more than about 20 wt.-%, wt.-% with respect to the whole weight of the composition, the polymerizable monomer (1) being characterized as follows: having exactly two (meth)acrylate reactive moieties, having an unsymmetrical backbone as linkage between the (meth)acrylate reactive moieties, the two (meth)acrylate reactive moieties being attached onto the unsymmetrical monomer backbone as alkyl esters, the unsymmetrical backbone comprising one aromatic moiety of the phenolic type, the polymerizable monomer (1) not containing an acidic moiety, other atoms than carbon, hydrogen, nitrogen, and oxygen, a bisphenol moiety. The invention is also directed to the use of the dental composition as or for producing a dental filling material, dental cement, crown and bridge material, inlay, onlay, veneer, orthodontic device or dental mill blank.

12 Claims, No Drawings

(56) References Cited

U.S. PATENT DOCUMENTS

| | | |
|---|---|---|
| 5,130,347 A | 7/1992 | Mitra |
| 5,530,038 A | 6/1996 | Yamamoto |
| 5,545,676 A | 8/1996 | Palazzotto |
| 5,624,260 A | 4/1997 | Wilcox |
| 5,865,803 A | 2/1999 | Major |
| 5,893,714 A | 4/1999 | Arnold |
| 5,918,772 A | 7/1999 | Keller |
| 5,944,419 A | 8/1999 | Streiff |
| 6,444,725 B1 | 9/2002 | Trom |
| 6,458,868 B1 | 10/2002 | Okada |
| 6,730,156 B1 | 5/2004 | Windisch |
| 6,769,912 B2 | 8/2004 | Beuschel |
| 2003/0008967 A1 | 1/2003 | Hecht |
| 2003/0132539 A1 | 7/2003 | Althoff |
| 2003/0175659 A1* | 9/2003 | Tiba ............... A61K 6/0023 433/217.1 |
| 2005/0236586 A1 | 10/2005 | Hartung |
| 2006/0187752 A1 | 8/2006 | Keller |
| 2007/0090079 A1 | 4/2007 | Keller |
| 2007/0172789 A1 | 7/2007 | Muller |
| 2010/0076115 A1 | 3/2010 | Utterodt |
| 2011/0315928 A1* | 12/2011 | Jin ............... A61K 6/09 252/301.35 |
| 2012/0068388 A1 | 3/2012 | Sakamoto |
| 2013/0109777 A1* | 5/2013 | Eckert ............... A61K 6/0023 522/175 |

* cited by examiner

DENTAL COMPOSITION AND USE THEREOF

FIELD OF THE INVENTION

The invention relates to a dental composition which is in particular useful for restorative purposes. The composition comprises a hardenable resin matrix comprising non-acidic hardenable components, a filler and an initiator and shows improved physical properties like compressive strength.

BACKGROUND ART

There are different dental filling materials which are used for restorative purposes, including amalgam and dental composite materials. In order to fulfill its function (replacement of lost tooth structure), dental filling materials need to have adequate physical properties. In particular, they have to have sufficient strength to be able to absorb and resist chewing forces. If, however, the material is too hard, it will also become more brittle. Thus, a dental filling material not only needs to be sufficiently hard, but also needs to be to some extend flexible.

To address these needs, commercially available dental composite filling materials typically contain a certain amounts of resin matrix, filler and initiator.

A widely used polymerizable (meth)acrylate component contained in the resin matrix is bisphenol A-glycidyl methacrylate (Bis-GMA) or other bisphenol based (meth)acrylate monomers.

Compositions containing bisphenol-based monomers are said to have a variety of advantageous properties like high compressive strength, thus enabling the practitioner to formulate a variety of different dental compositions for restorative purposes.

Some literature, however, seems to indicate that bisphenol based monomers are not always recommended for all purposes. Alternative polymerizable (meth)acrylate components are thus needed.

US 2010/076115 (Heraeus Kulzer) relates to compositions for dental composites comprising acrylic acid esters of tricyclo[5.2.1.02.6] decane with urethane groups U.S. Pat. No. 3,853,962 (Gander) relates to dental restorative cements comprising the methacrylate monomer 1,3-bis[2-,3-di(methacryloxy)-propoxy]-benzene. Restorative compositions containing this kind of monomer are said to have improved compressive strength and related physical properties.

U.S. Pat. No. 4,744,827 (Winkel) describes (meth)acrylic acid derivatives of a tricyclodecane exhibiting considerably less polymerization shrinkage.

WO 2012/003136 (3M) relates to a dental composition comprising a hardenable compound with a comparable rigid backbone, which may comprise urethane moieties. The composition is said to have advantageous properties e.g. with respect to shrinkage stress.

WO 2009/042574 (3M) describes methacrylate based monomers containing a urethane linkage showing a well balanced properties with respect to viscosity, refractive index, molecular weight and shrinkage value.

US 2011/0315928 (Jin et al.) describes a low stress flowable dental composition comprising an oligomeric resin, a second resin and a filler. The composition is said to be self-leveling and be suitable as bulk fill material. The oligomeric resin contains a photoresponsive moiety which may be derived from any conventional initiator.

DESCRIPTION OF THE INVENTION

Generally, there is a need for a dental composition having adequate physical properties, which can be formulated without the need of using Bis-GMA or other bisphenol based (meth)acrylate monomers or components.

In particular, it is one object of the present invention to provide a dental composition showing improved physical properties, like compressive strength, however, without negatively influencing shrinkage stress upon polymerization. Further, it would be desirable, if the dental composition can be formulated without using bisphenol moieties containing (meth)acrylate components.

In particular, it is an object of the present invention to provide a Bis-GMA free dental composition showing improved physical properties, like compressive strength, however, without negatively influencing shrinkage stress upon polymerization.

To address this object, the present invention features a dental composition as described in the claims comprising
  Polymerizable monomer (1),
  Initiator component(s) suitable to initiate the curing or hardening of the polymerizable monomer (1),
  Filler component(s) in an amount of more than about 20 wt.-%, wt.-% with respect to the whole weight of the composition,
the polymerizable monomer (1) being characterized as follows:
  having exactly two (meth)acrylate reactive moieties,
  having an unsymmetrical backbone as linkage between the (meth)acrylate reactive moieties,
  the two (meth)acrylate reactive moieties being attached onto the unsymmetrical backbone as alkyl esters,
  the unsymmetrical backbone comprising preferably only one aromatic moiety of the phenolic type,
  the hydroxyl group(s) of the aromatic moiety of the phenolic type being always attached via alkyl-aryl ethers onto alkyl residues,
  having one or two urethane moieties within the unsymmetrical backbone,
the polymerizable monomer (1) not containing
  other atoms than carbon, hydrogen, nitrogen and oxygen,
  other aromatic moieties than aromatic moieties of the phenolic type,
  bisphenol moieties.

Moreover, the invention features a method of using the composition as described in the text of the invention for producing or as dental filling material, crown and bridge material (e.g. temporary and long-term), inlay, onlay, veneer, orthodontic device or dental mill blank.

Unless defined differently, for this description the following terms shall have the given meaning:

A "dental composition" or a "composition for dental use" or a "composition to be used in the dental field" is any composition which can and is to be used in the dental field. In this respect the composition should not be detrimental to the patients' health and thus free of hazardous and toxic components being able to migrate out of the composition. Examples of dental compositions include permanent and temporary crown and bridge materials, artificial crowns, anterior or posterior dental filling materials, dental mill blanks and orthodontic devices.

Dental compositions are typically hardenable compositions. Dental compositions for hardening in the mouth can be hardened at ambient conditions, including a temperature range from about 15 to 50° C. or from about 20 to 40° C. within a time frame of about 30 min or 20 min or 10 min. Higher temperatures are not recommended as they might cause pain to the patient and may be detrimental to the patient's health. Dental compositions are typically provided to the practitioner in comparable small volumes, that is volumes in the range from about 0.1 to about 100 ml or from about 0.5 to about 50 ml or from about 1 to about 30 ml. Thus, the storage volume of useful packaging devices is typically within these ranges.

A "dental filling material" is a hardenable material designed to restore missing tooth structure, in particular to fill a cavity in hard dental tissue.

A "crown and bridge material" within the meaning of the invention is a hardenable material used for making dental crowns and bridges. These materials are typically used during the time period a dental technician needs for producing a permanent prosthetic work such as a crown or bridge. These time periods can last from a few days (1 to about 6 days), a few weeks (1 to about 4 weeks) or a few months (1 to about 6 month). A long term crown and bridge material is typically used over a time period of about 6 to 24 months.

By "dental milling block" or "dental mill blank" is meant a solid block (3-dim article) of material from which a dental article can be machined. A dental milling block has typically a geometrically defined shape. A dental milling block may have a size of about 20 mm to about 30 mm in two dimensions, for example may have a diameter in that range, and may be of a certain length in a third dimension. A block or blank for making a single crown may have a length of about 15 mm to about 30 mm, and a block or blank for making bridges may have a length of about 40 mm to about 80 mm. A typical size of a block or blank as it is used for making a single crown has a diameter of about 24 mm and a length of about 19 mm. Further, a typical size of a block or blank as it is used for making bridges has a diameter of about 24 mm and a length of about 58 mm. Besides the above mentioned dimensions, a dental milling block may also have the shape of a cube, a cylinder or a cuboid. Larger milling blocks may be advantageous if more than one crown or bridge should be manufactured out of one blank. For these cases, the diameter or length of a cylindric or cuboid shaped mill blank may be in a range of about 80 to about 200 mm, with a thickness being in the range of about 10 to about 30 mm.

By "machining" is meant milling, grinding, cutting, carving, or shaping a material by a machine. Milling is usually faster and more cost effective than grinding.

An "initiator system" or "initiator" shall include those components of the dental composition being able to start or initiate the curing process of the hardenable components, also described herein as "curing the hardenable components".

A "resin matrix" shall mean the organic part of the dental composition being composed of the hardenable components and organic diluents, if present.

A "hardenable component or material" (e.g., "polymerizable component" or "crosslinkable component") is any component which can be cured or solidified e.g., by heating to cause polymerization, chemical crosslinking, radiation-induced polymerization or crosslinking by using a redox initiator. A hardenable component may contain, for example, only one, two, three or more polymerizable groups. Typical examples of polymerizable groups include unsaturated carbon groups, such as a vinyl group being present e.g. in a (meth)acrylate group.

A "curable composition" is a mixture of two or more components, the mixture being able to be cured or solidified e.g., by heating to cause chemical crosslinking, radiation-induced polymerization or crosslinking by using a redox initiator. A curable composition may advantageously include a hardenable component.

A "monomer" is any chemical substance which can be characterized by a chemical formula, bearing one or more polymerizable groups (including (meth)acrylate groups) which can be polymerized to oligomers or polymers thereby increasing the molecular weight. The molecular weight of monomers can usually simply be calculated based on the chemical formula given.

As used herein, "(meth)acryl" is a shorthand term referring to "acryl" and/or "methacryl". For example, a "(meth) acryloxy" group is a shorthand term referring to either an acryloxy group (i.e., $CH_2$=CH—C(O)—O—) and/or a methacryloxy group (i.e., $CH_2$=C($CH_3$)—C(O)—O—). Similarly, (meth)acrylate is a shorthand term referring to "acrylate" and/or "methacrylate."

"Curing," "hardening," and "setting reaction" are used interchangeably and refer to a reaction wherein physical properties such as viscosity and hardness of a composition change (e.g., increase) over time due to a chemical reaction between the individual components.

A "polymerizable monomer(s) with acidic moieties" is meant to include monomers, oligomers, and polymers having ethylenic unsaturation and acid and/or acid-precursor functionality. Acidic-precursor functionalities include, e.g. anhydrides, acid halides and pyrophosphates. The acidic group preferably comprises one or more carboxylic acid residues, such as —COOH or —CO—O—CO—, phosphoric acid residues, such as —O—P(O)(OH)OH, phosphonic acid residues such as C—P(O)(OH)OH, sulfonic acid residues, such as —$SO_3$H or sulfinic acid residues such as —$SO_2$H.

A "phenolic type" moiety is generally understood as an aromatic moiety bearing at least one oxygen atom directly attached onto an aromatic residue, more precisely, a moiety comprising the structural element [C6RxO] with x being 1, 2, 3, 4, 5 or 6, R being H, alkyl (e.g. C1 to C8), —O—, —CO— or C(O)O— and C6 forming an aromatic ring. For example, "C6H5O—" (phenoxy) represents the most simple "phenolic type" moiety.

A "powder" means a dry, bulk solid composed of a large number of very fine particles that may, for example, flow freely when shaken or tilted.

A "particle" means a substance being a solid having a shape which can be geometrically determined. Particles can typically be analysed with respect to e.g. particle size or diameter. Particles may be amorphous or crystalline.

"Radiation curable" shall mean that the component (or composition, as the case may be) can be cured by applying radiation, preferably electromagnetic radiation with a wavelength in the visible light spectrum under ambient conditions and within a reasonable time frame (e.g. within about 15, 10 or 5 min). The term "visible light" is used to refer to light having a wavelength of about 400 to about 700 nanometers (nm).

"Hard dental tissue" means dentin and enamel.

"Ambient conditions" mean the conditions which the inventive composition is usually subjected to during storage and handling. Ambient conditions may, for example, be a pressure of about 900 to about 1100 mbar, a temperature of about −10 to about 60° C. and a relative humidity of about 10 to about 100%. In the laboratory ambient conditions can be adjusted to about 23° C. and about 1013 mbar and about 50% relative humidity. In the dental and orthodontic field ambient conditions are reasonably understood as a pressure of about 950 to about 1050 mbar, temperature of about 15 to about 40° C. and relative humidity of about 20 to about 80%.

A composition is "essentially or substantially free of" a certain component within the meaning of the invention, if the composition does not contain said component as an essential feature. Thus, said component is not willfully added to the composition either as such or in combination with other components or ingredient of other components. A composition being essentially free of a certain component usually contains the component in an amount of less than about 1 wt.-% or less than about 0.1 wt.-% or less than about 0.01 wt.-% with respect to the whole composition. Ideally, the composition or solution does not contain the said component at all. However, sometimes the presence of a small amount of the said component is not avoidable e.g. due to impurities.

As used herein, "a", "an", "the", "at least one" and "one or more" are used interchangeably. The terms "comprises" or "contains" and variations thereof do not have a limiting meaning where these terms appear in the description and claims. The term "comprising" also includes the more limited expressions "consisting essentially of" and "consisting of".

Also herein, the recitations of numerical ranges by endpoints include all numbers subsumed within that range (e.g., 1 to 5 includes 1, 1.5, 2, 2.75, 3, 3.80, 4, 5, etc.).

Adding an "(s)" to a term means that the term should include the singular and plural form. E.g. the term "additive(s)" means one additive and more additives (e.g. 2, 3, 4, etc.).

Unless otherwise indicated, all numbers expressing quantities of ingredients, measurement of physical properties such as described below and so forth used in the specification and claims are to be understood as being modified in all instances by the term "about."

DETAILED DESCRIPTION OF THE INVENTION

It has been found that the composition described in the present text is superior with respect to a variety of properties:

A hardened dental composition comprising the asymmetric (i.e. non symmetric), polymerizable monomers described in the present text shows improved physical properties, especially with respect to compressive strength.

Further, the desired dental composition can be formulated without using bisphenol moiety(s) containing monomers or components.

The asymmetric, polymerizable monomers described in the present text typically do not solidify at room temperature and thus facilitate the incorporation of a sufficient amount of filler, an amount which is typically needed for formulating a dental filling or crown and bridge material or dental mill blank.

In certain embodiments the dental composition fulfills at least one or more, sometimes all of the following features before hardening:
pH value, if brought in contact with water: neutral (e.g. about 6 to about 8) or acidic (e.g. about 2 to about 5), radiation or redox curable;
storage stable;
being provided as a one or two-component system.

If desired and more precisely, the viscosity can be determined under the following conditions: 23° C.; shear rate: 100 1/s; measured with a cone/plate geometry CP25-1 with a Physica MCR 301 Rheometer, Anton Paar GmbH, Graz, Austria.

If dissolved, dispersed (e.g. 1 g composition in 10 ml water) or brought in contact with in water, the composition typically exhibits a pH value in the range from about 6 to about 8 or about 7. That is, the composition as a whole essentially has a neutral pH, if brought in contact with water, or is slightly acidic.

The invention provides a composition which can be hardened in an acceptable time frame, e.g., less than about 300 seconds (s) or less than about 180 s or less than about 120 s, and to a sufficient depth using visible light source equipment already available in the dental office.

In certain embodiments the dental composition fulfills at least one or more, sometimes all of the following properties (after hardening):
compressive strength: at least about 380 MPa or at least about 400 or at least about 420 MPa;
shrinkage stress: not more than about 2350 µstrain or not more than about 2200 µstrain or not more than about 2050 µstrain.

If desired, the compressive strength can be determined according to ISO 4049 using specimens having the dimension of 3 mm×3 mm×5 mm.

If desired, the shrinkage stress can be determined according to the procedure described by Sakaguchi et al. (Dent. Mater. 1997, 13, 233-239) by irritating 45 mg samples for 40 s using a 3M XL3000 (650 mW) irradiation device.

The dental composition comprises a resin matrix. The polymerizable monomer (1) represents one component of the resin matrix.

The polymerizable monomer (1) can also be described as unsymmetrical, di-functional urethane (meth)acrylate monomer.

In more detail, the polymerizable monomer (1) can be described as follows:
having exactly two (meth)acrylate reactive moieties,
having an unsymmetrical backbone as linkage between the (meth)acrylate reactive moieties,
the two (meth)acrylate reactive moieties being attached onto the unsymmetrical backbone as alkyl esters,
the unsymmetrical backbone comprising an aromatic moiety of the phenolic type,
the hydroxyl group(s) of the aromatic moiety of the phenolic type being always attached via alkyl-aryl ethers onto alkyl residues,
having one or two urethane moieties within the unsymmetrical backbone,
typically not more than two additional aromatic moieties within the unsymmetrical backbone not being part of the linkage between the reactive groups but being attached onto this linkage between the reactive groups,
the polymerizable monomer (1) not containing
other atoms than carbon, hydrogen, nitrogen and oxygen,
other aromatic moieties than aromatic moieties of the phenolic type,
bisphenol moieties.

The polymerizable monomer (1) can also be characterized by at least one of the following features:
having a molecular weight within a range of about 300 to 1,000,
the aromatic moiety of the phenolic type comprising a tyrosol moiety, hydroxy benzylic alcohol moiety, hydroxy benzoic acid moiety, resorcinol moiety, catechol moiety.

Some embodiments of the polymerizable monomer (1) comprise a glycerol moiety (—O—CH2—CH(OH)—CH2—O—) and/or a phenylglycerol moiety (—O—CH2—CH(O—)—CH2—OPh).

The polymerizable monomer (1) is typically characterized by the following embodiment:

Embodiment (I)

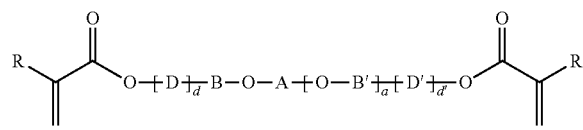

with:

[-D-]$_d$-B-O-A-[-O-B'-]$_a$-[-D'-]$_{d'}$ representing the unsymmetrical backbone as linkage between the polymerizable moieties, a=0 or 1,

A=

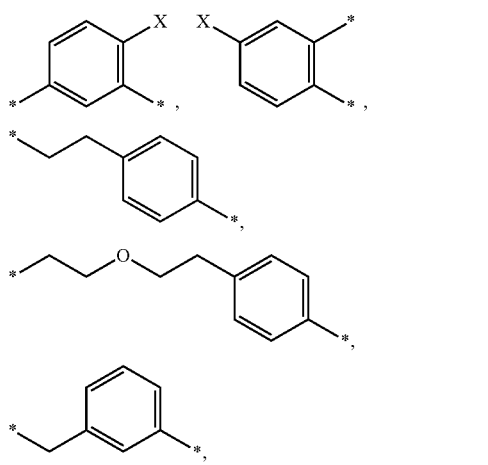

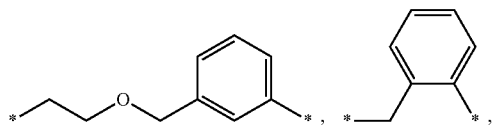

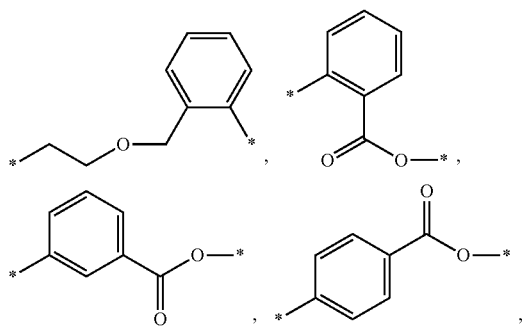

A being always attached as aryl-alkyl ether onto B and/or B',

B=*—$(CH_2)_b$—*, *—$(CH_2—CH_2—O—CH_2—CH_2)$—*,
  *—$(CH_2—CH_2—O—CH_2—CH_2—CH_2)$—*,
  *—$(CH_2—CH_2—CH_2—O—CH_2—CH_2—CH_2)$—*,

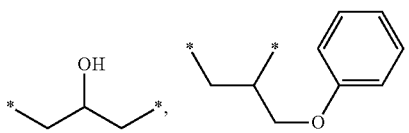

B being attached as alkyl ester onto the (meth)acrylate reactive group or as urethane onto D, b=2 to 6, B'=*—$(CH_2)_{b'}$—*, *—$(CH_2—CH_2—O—CH_2—CH_2)$—*,

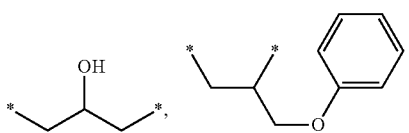

B' being attached as alkyl ester onto the (meth)acrylate reactive group or as urethane onto D', b'=2-6, D, D' being independently selected from *—$(CH_2)_n$—NH—(C=O)—O—*, *—$(CH_2—C(CH_3)_2—CH_2)$—NH—(C=O)—O—*, *—$(CH_2—CH_2—C(CH_3)_2)$—NH—(C=O)—O—*

D and D' being always attached via the oxygen of the urethane linkage onto B and/or B', d=0,1 and d'=0,1 with the proviso that (d+d')=1 or 2, n=2 to 5, R being independently selected from H, methyl, X being independently selected from H and C1 to C6 alkyl (e.g. methyl, ethyl, hexyl, tert-butyl).

The polymerizable monomer (1) may also be characterized by either of the following embodiments:

Embodiment (Ia)

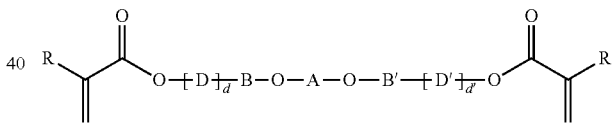

with:

[-D-]$_d$-B-O-A-O-B'-[-D'-]$_{d'}$ representing the unsymmetrical monomer backbone as linkage between the reactive groups,

A=

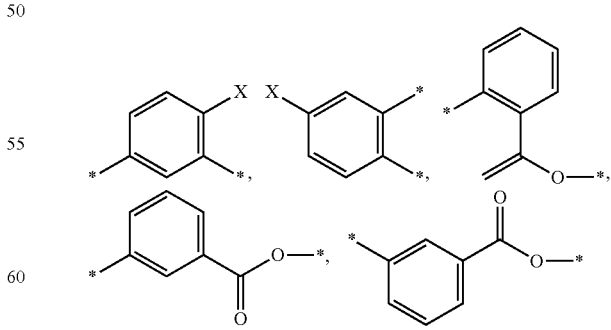

A being always attached as aryl-alkyl ether onto B and/or B',

B=*—$(CH_2)_b$—*, *—$(CH_2—CH_2—O—CH_2—CH_2)$—*,
  *—$(CH_2—CH_2—O—CH_2—CH_2—CH_2)$—*,
  *—$(CH_2—CH_2—CH_2—O—CH_2—CH_2—CH_2)$—*,

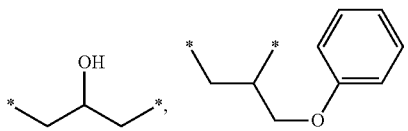

B being attached as alkyl ester onto the (meth)acrylate reactive group or as urethane onto D,
b=2 to 6,
B'=*—(CH$_2$)$_{b'}$—*, *—(CH$_2$—CH$_2$—O—CH$_2$—CH$_2$)—*,

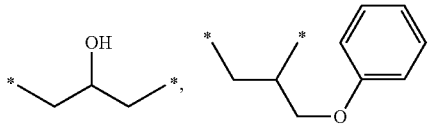

B' being attached as alkyl ester onto the (meth)acrylate reactive group or as urethane onto D',
b'=2 to 6,
D, D' being independently selected from *—(CH$_2$)$_n$—NH—(C=O)—O—*, *—(CH$_2$—C(CH$_3$)$_2$—CH$_2$)—NH—(C=O)—O—*, *—(CH$_2$—CH$_2$—C(CH$_3$)$_2$)—NH—(C=O)—O—*
D, D' being always attached via the oxygen of the urethane linkage onto B and/or B',
d=0 or 1 and d'=0 or 1 with the proviso that (d+d')=1 or 2,
n=2 to 5,
R being independently selected from H, methyl,
X being independently selected from H and C1 to C6 alkyl (e.g. methyl, ethyl, hexyl, tert-butyl).

Embodiment (Ib)

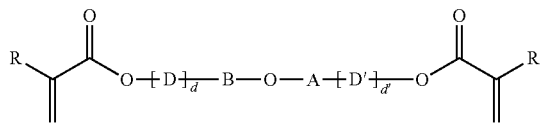

with:
[-D-]$_d$-B-O-A-[-D'-]$_{d'}$ representing the unsymmetrical backbone as linkage between the reactive groups,
A=

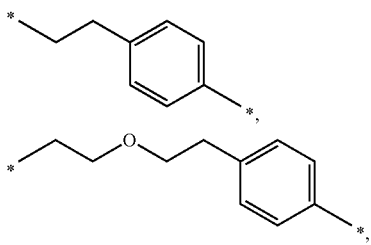

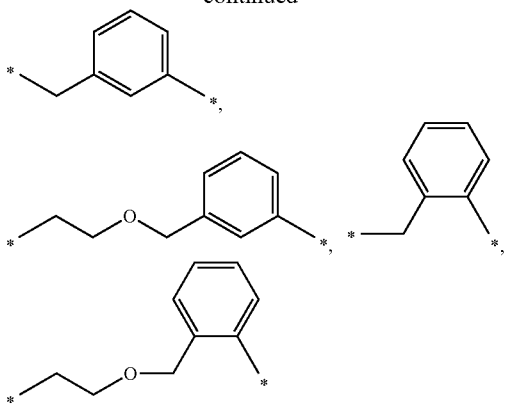

A being attached as aryl-alkyl ether onto B and attached as alkyl ester onto the (meth)acrylate reactive group or as urethane onto D',
B=*—(CH$_2$)$_b$—*, *—(CH$_2$—CH$_2$—O—CH$_2$—CH$_2$)—*,

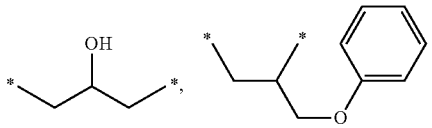

B being attached as alkyl ester onto the (meth)acrylate reactive group or as urethane onto D,
b=2 to 6,
D, D' being independently selected from *—(CH$_2$)$_n$—NH—(C=O)—O—*, *—(CH$_2$—C(CH$_3$)$_2$—CH$_2$)—NH—(C=O)—O—*, *—(CH$_2$—CH$_2$—C(CH$_3$)$_2$)—NH—(C=O)—O—*
D, D' being always attached via the oxygen of the urethane linkage onto B and/or B',
d=0 or 1 and d'=0 or 1 with the proviso that (d+d')=1 or 2,
n=2 to 5,
R being independently selected from H and methyl.
"*" representing those sites of a moiety of the monomer, where that moiety is bonded to another moiety of the monomer.

In all the above formulas R can independently be selected from H and CH3, meaning that in each component R can be either methyl or hydrogen, or that one R is methyl and the other R is hydrogen.

The polymerizable monomer (1) can also be classified with respect to the backbone. According to one embodiment, the backbone contains ether moieties and can be regarded as rather non polar. According to another embodiment, the backbone contains ether moieties and can be regarded as rather polar. According to a further embodiment, the backbone contains ether and ester moieties and can be regarded as rather polar.

Specific examples of polymerizable monomer (1) with a rather non polar backbone containing ether moieties include:

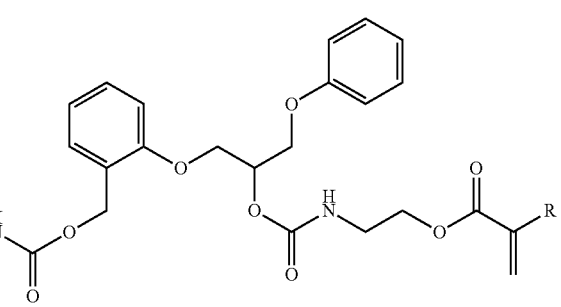

-continued
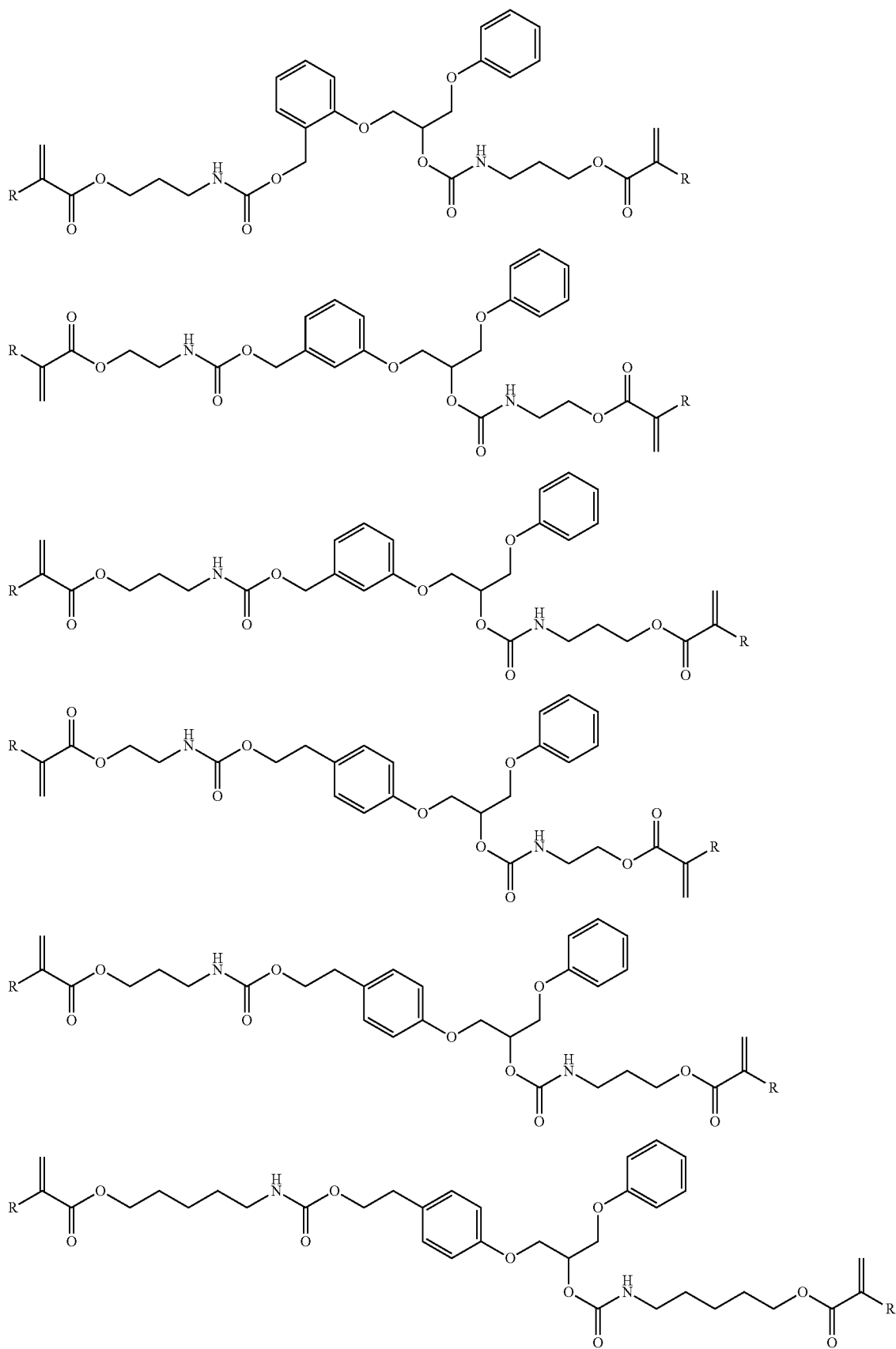

-continued
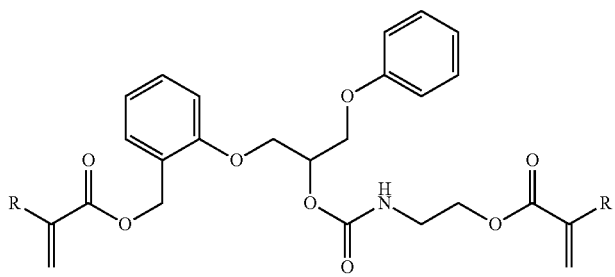
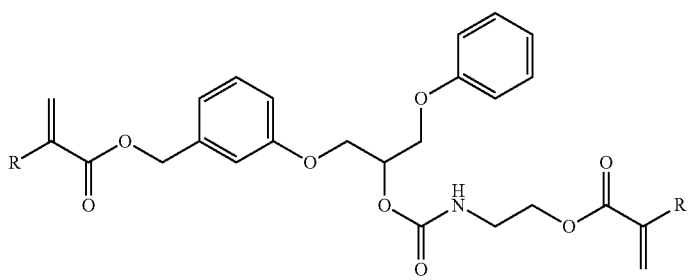
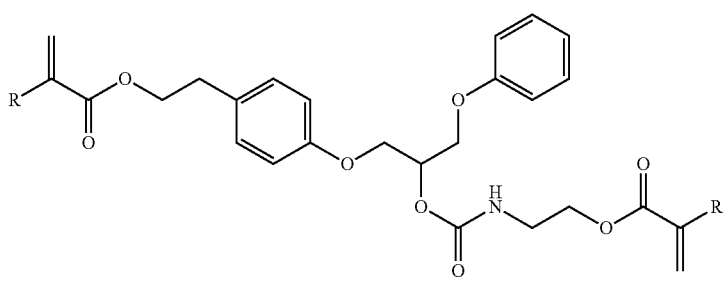
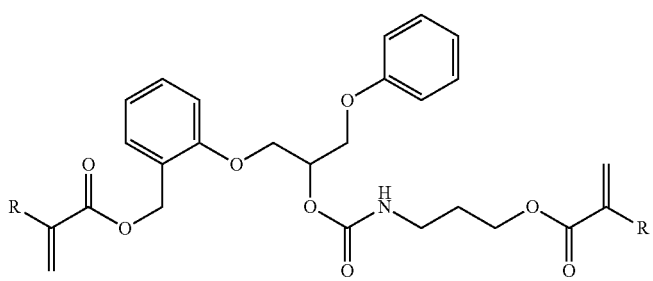
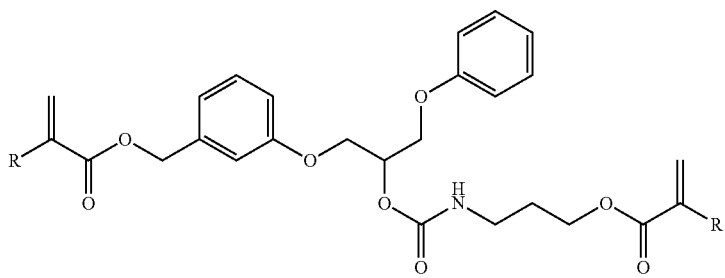
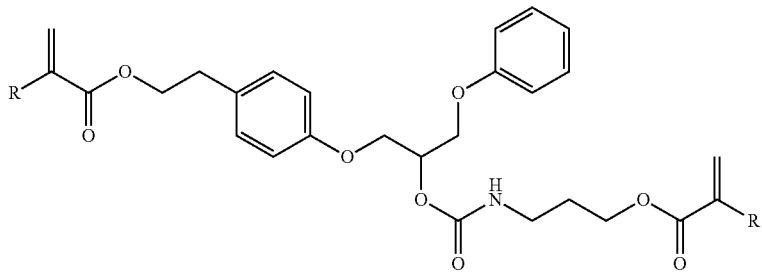

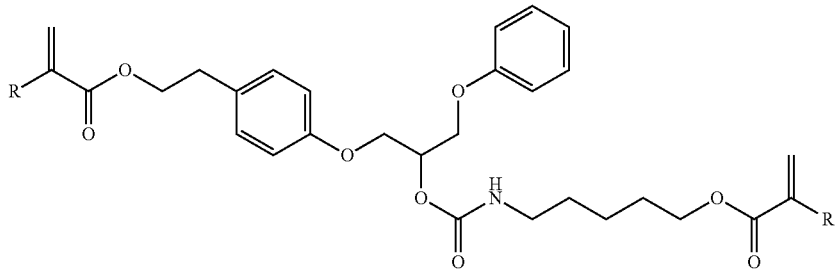
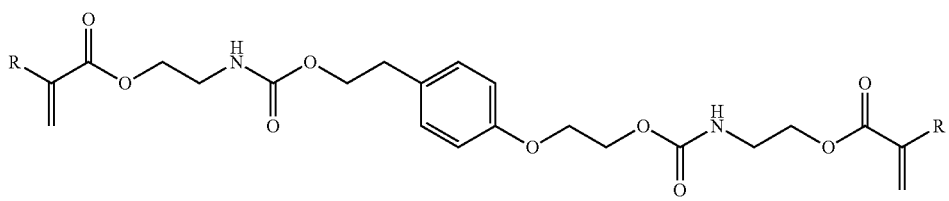
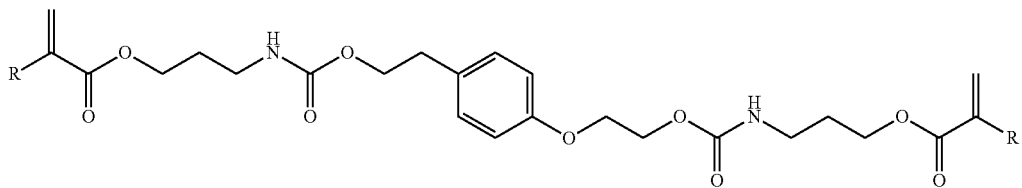
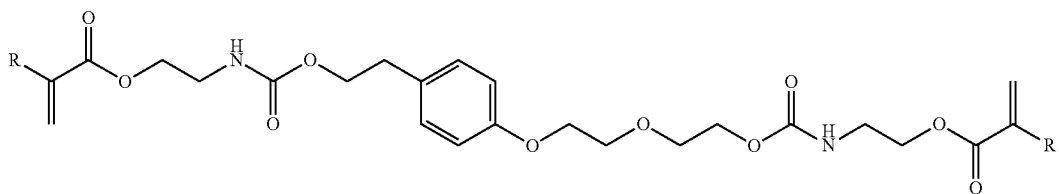
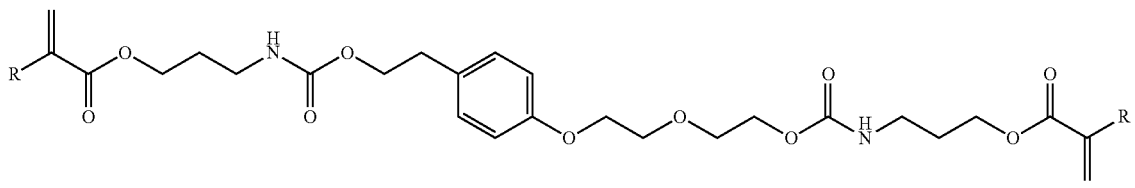
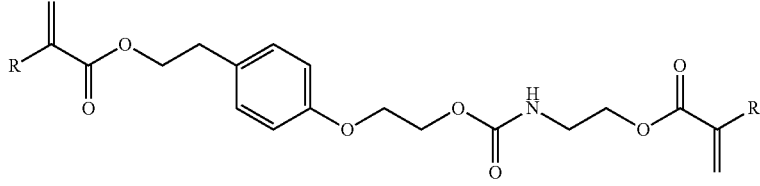
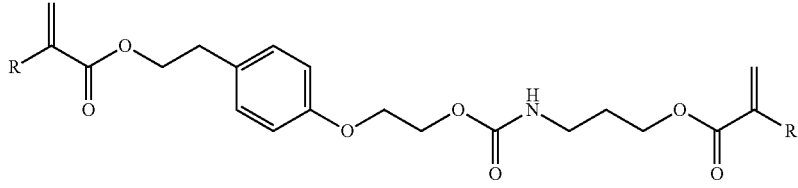
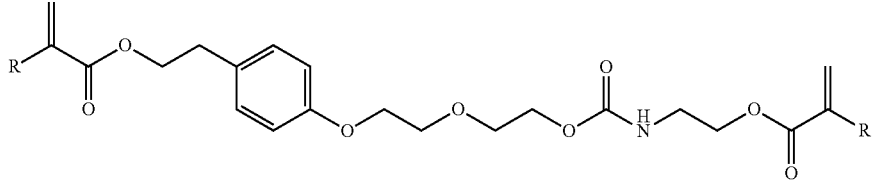

-continued
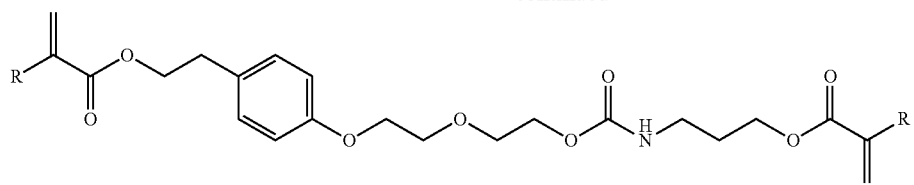
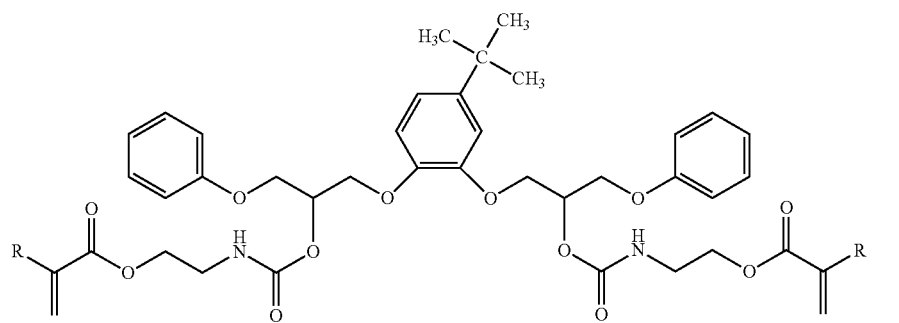
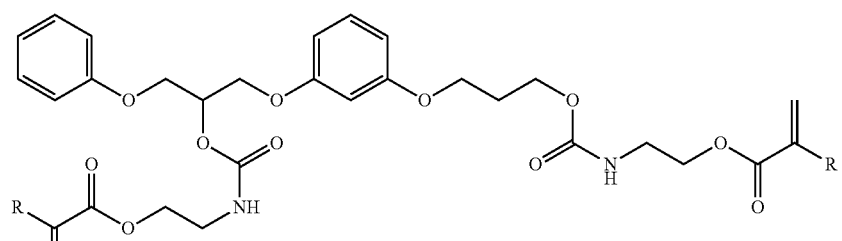
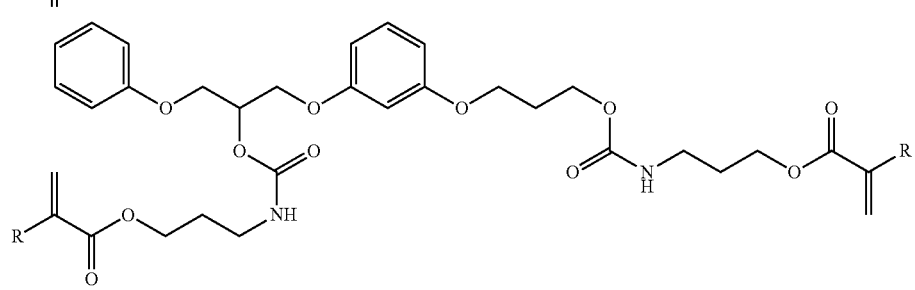
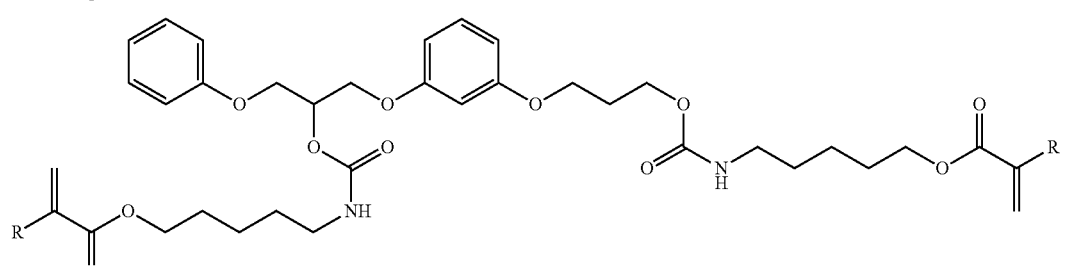
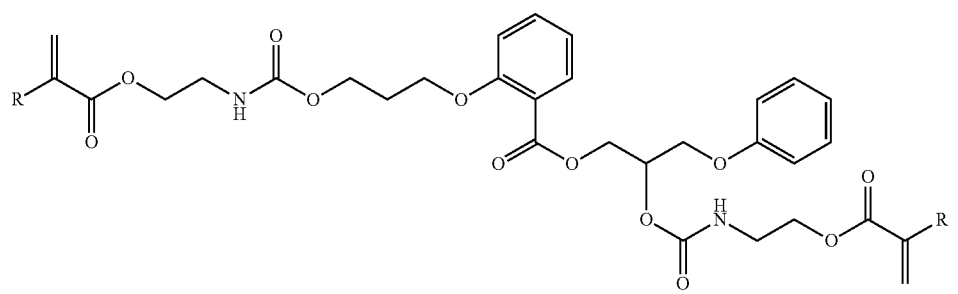

-continued
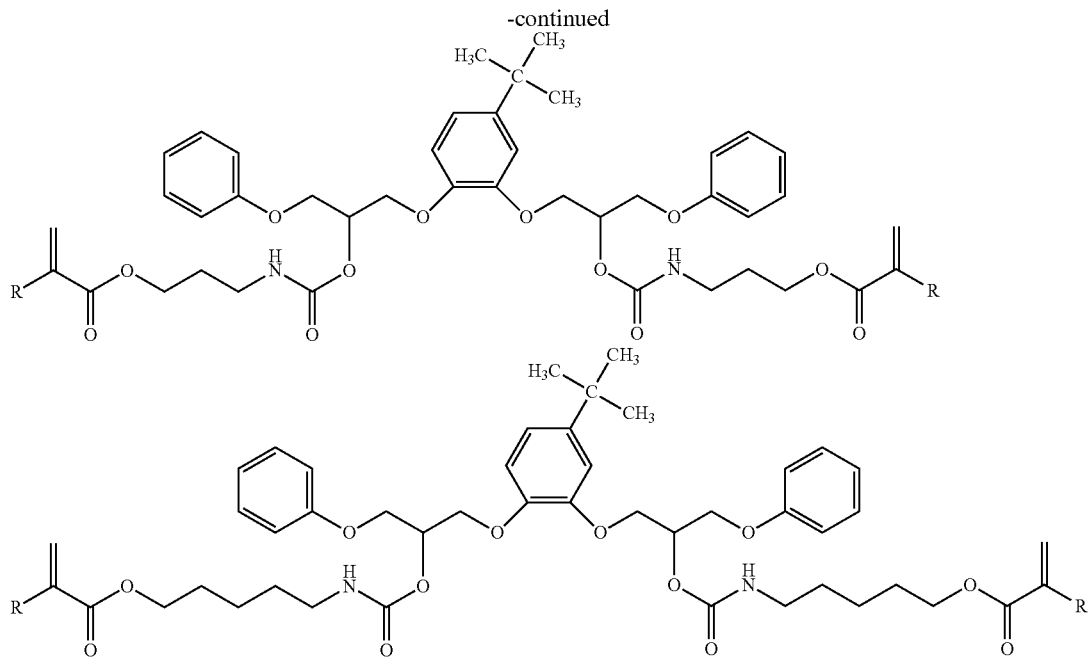
with R being independently selected from H and C1-C4 alkyl (in particular CH3).
Specific examples of polymerizable monomer (1) with a rather polar backbone containing ether moieties include:
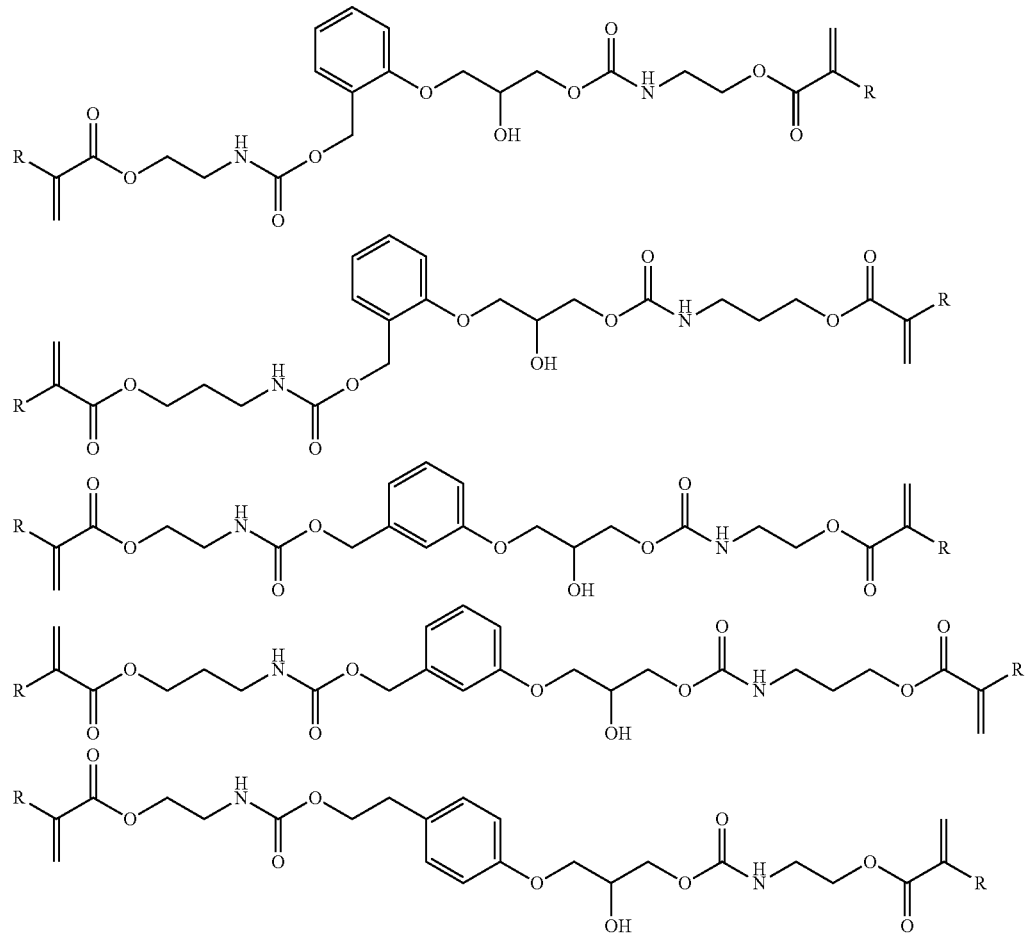

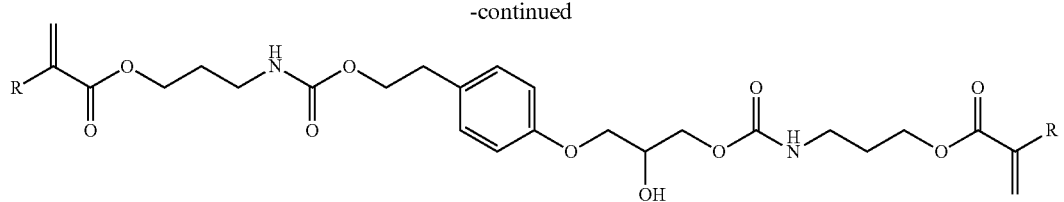
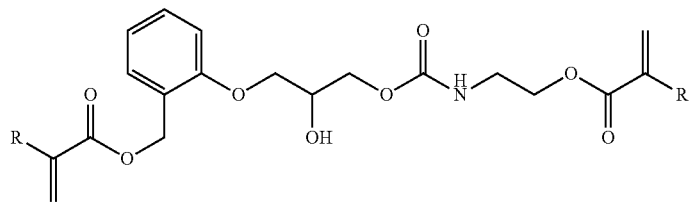
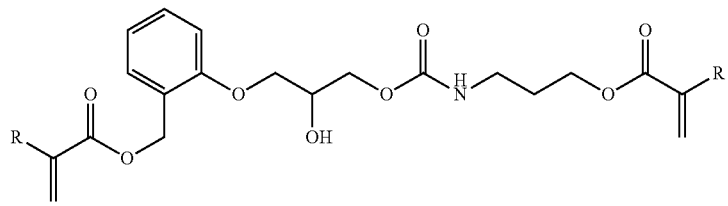
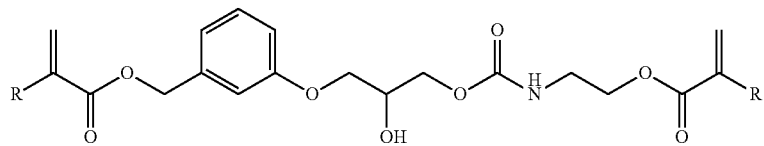
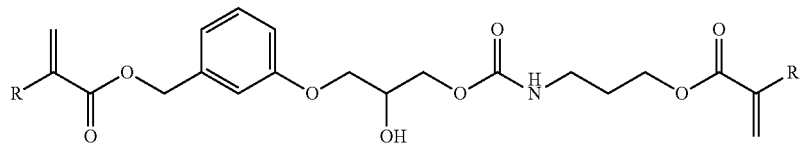
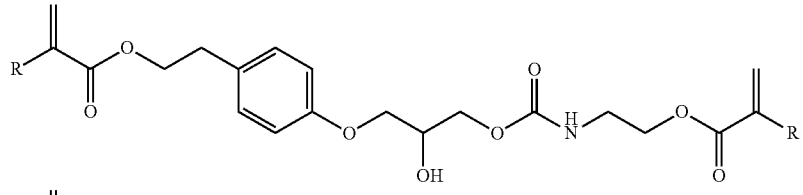
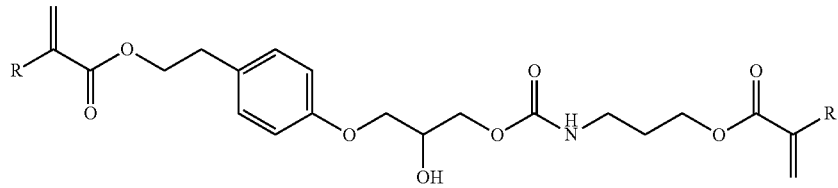
with R being independently selected from H and C1-C4 alkyl (in particular CH3).
Specific examples of polymerizable monomer (1) with a rather polar backbone containing ether and ester moieties include:

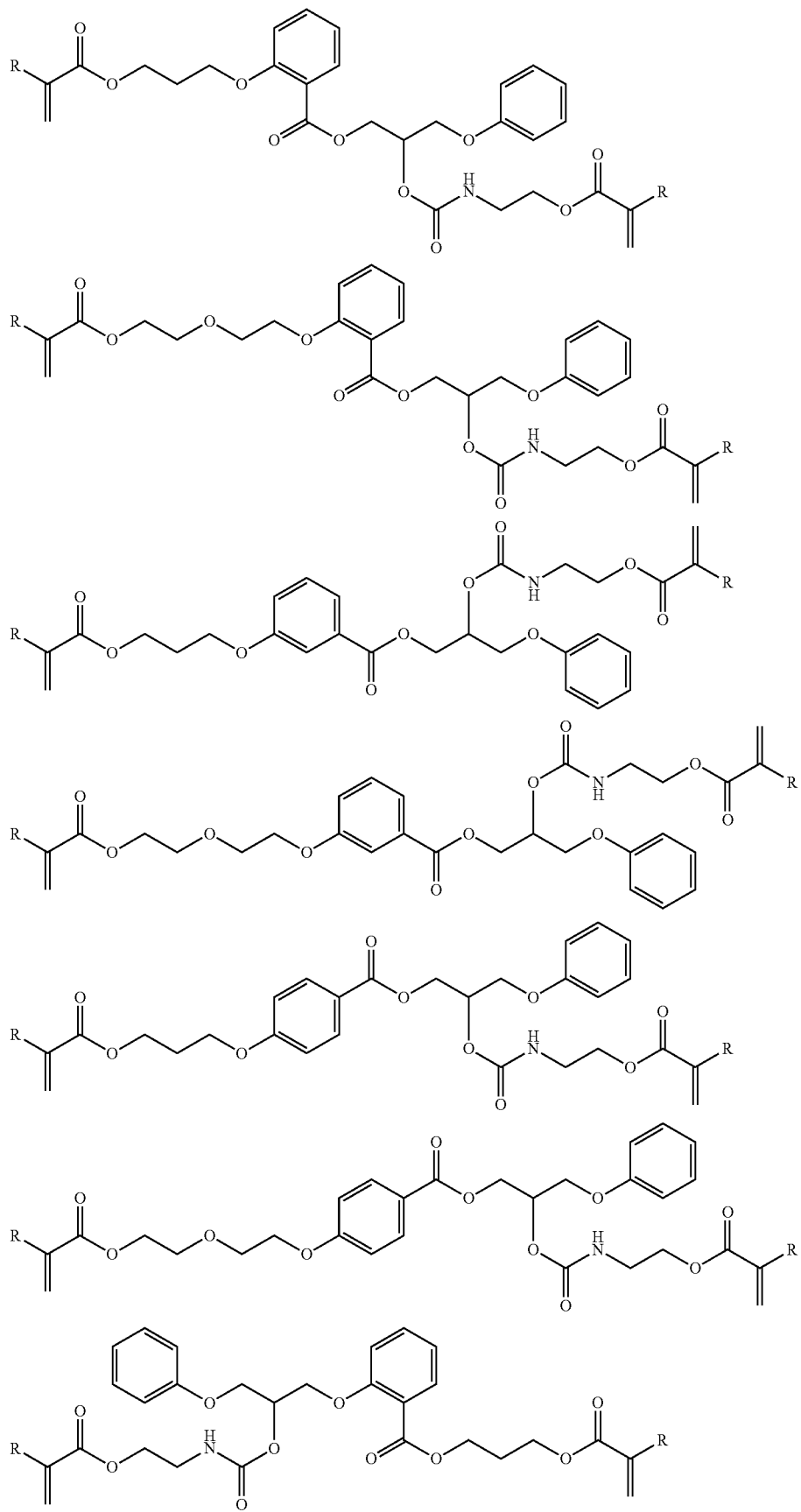

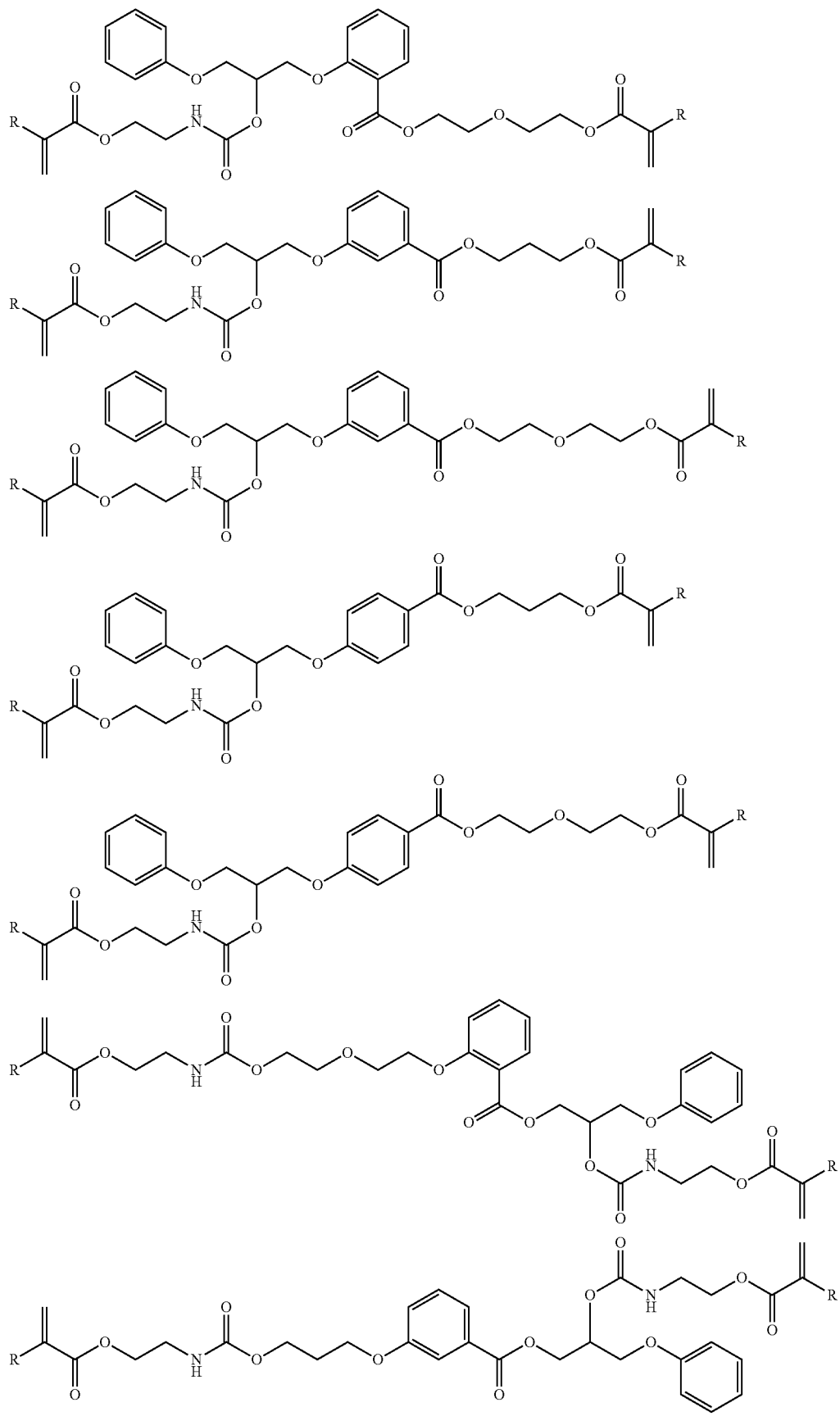

-continued
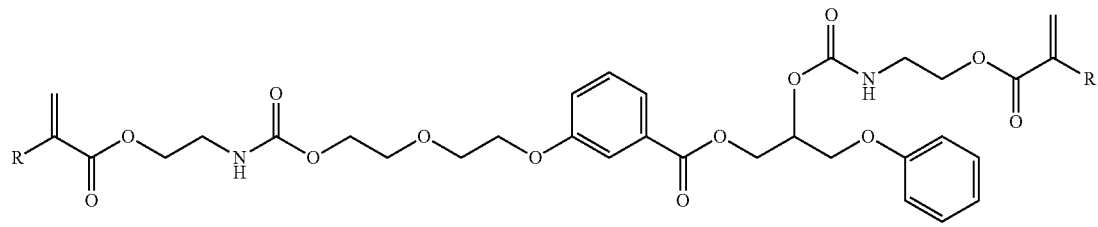
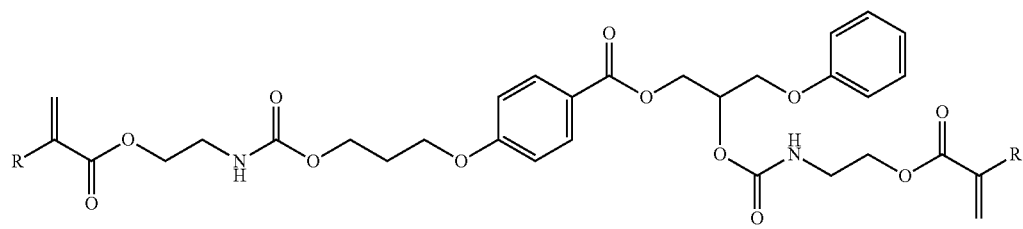
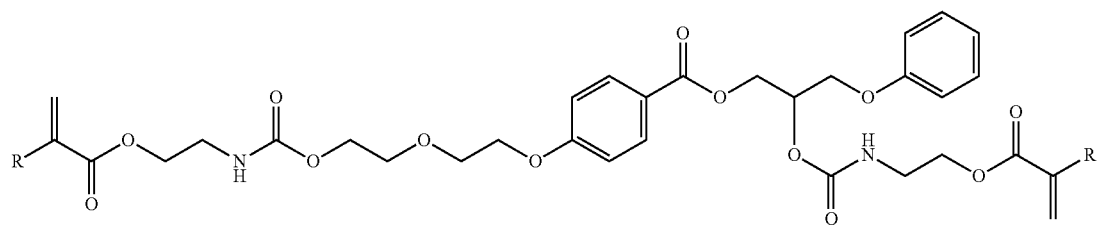
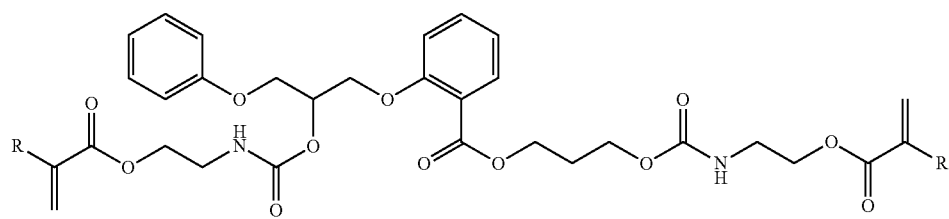
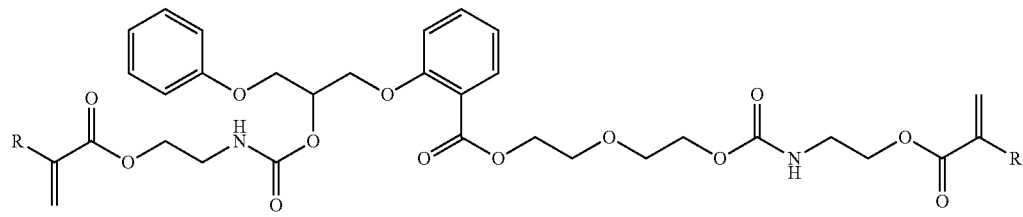
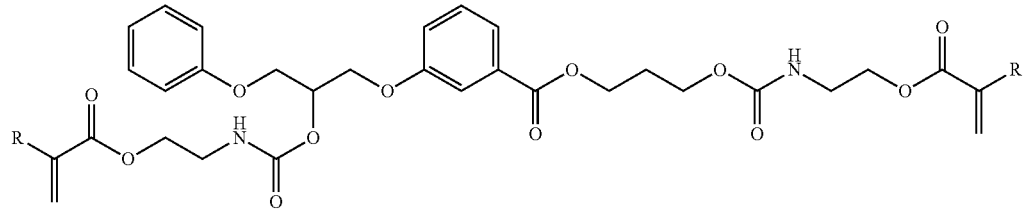
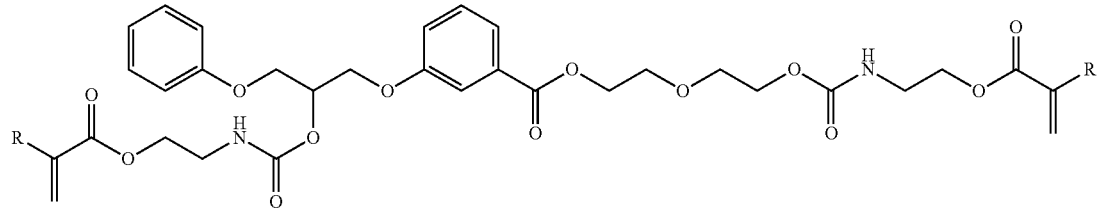

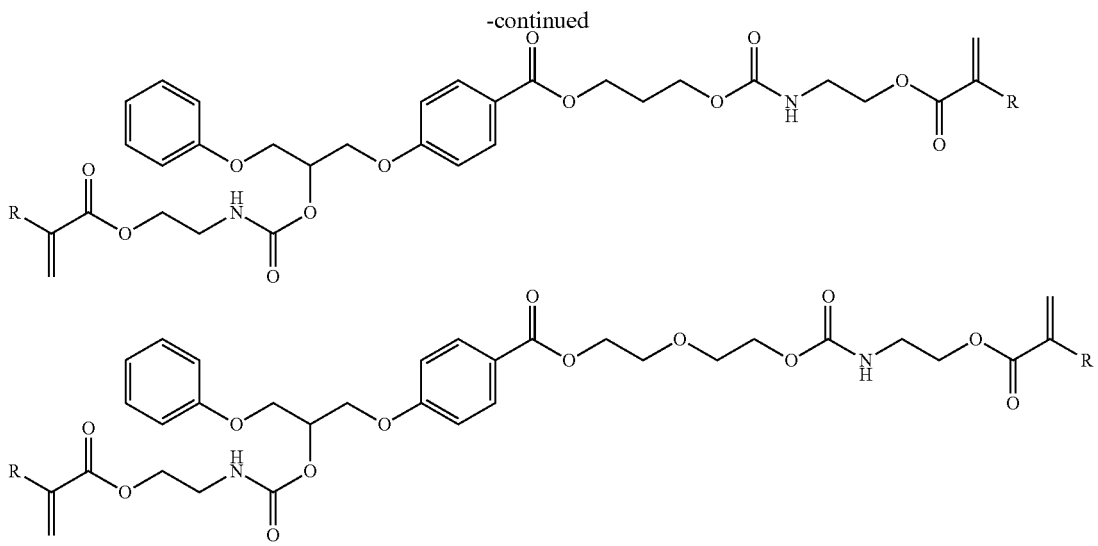

with R being independently selected from H and C1-C4 alkyl (in particular CH3).

Mixtures of two, three or more of the polymerizable monomers (1) can be used, if desired.

The polymerizable monomer (1) is typically contained in the following amounts:

Lower limit: at least about 1 or at least about 5 or at least about 10 wt.-%
Upper Limit: up to about 75 or up to about 70 or up to about 65 wt.-%
Range: from about 1 to about 75 or from about 5 to about 70 or from about 10 to about 65 wt.-%, wt.-% with respect to the amount of the whole composition.

Besides polymerizable monomer(s) without acidic groups like polymerizable monomer (1), the composition can also comprise polymerizable monomer(s) with acidic moieties (2) as part of the resin matrix.

Thus, the composition described in the present text may further comprise a polymerizable monomer (2) with an acidic moiety.

If present, the nature and structure of polymerizable monomer (2) is not particularly limited, unless the desired result cannot be achieved.

The presence of polymerizable monomer (3) can be beneficial because it can provide the composition with a desired acidity.

The polymerizable components with acid moiety (Al) can typically be represented by the following formula

with A being an ethylenically unsaturated group, such as a (meth)acryl moiety,
B being a spacer group, such as (i) linear or branched C1 to C12 alkyl, optionally substituted with other functional groups (e.g. halogenides (including Cl, Br, I), OH or mixtures thereof) (ii) C6 to C12 aryl, optionally substituted with other functional groups (e.g. halogenides, OH or mixtures thereof), (iii) organic group having 4 to 20 carbon atoms bonded to one another by one or more ether, thioether, ester, thioester, thiocarbonyl, amide, urethane, carbonyl and/or sulfonyl linkages, and
C being an acidic group,
m, n being independently selected from 1, 2, 3, 4, 5 or 6, wherein the acidic group comprises one or more carboxylic acid residues, such as —COOH or —CO—O—CO—, phosphoric acid residues, such as —O—P(O)(OH)OH, phosphonic acid residues, such as C—P(O)(OH)(OH), sulphonic acid residues, such as —$SO_3H$ or sulfinic acid residues such as —$SO_2H$.

Examples of polymerizable components with acid moiety include, but are not limited to glycerol phosphate mono (meth)acrylate, glycerol phosphate di(meth)acrylate, hydroxyethyl (meth)acrylate (e.g., HEMA) phosphate, bis ((meth)acryloxyethyl) phosphate, (meth)acryloxypropyl phosphate, bis((meth)acryloxypropyl) phosphate, bis((meth) acryloxy)propyloxy phosphate, (meth)acryloxyhexyl phosphate, bis((meth)acryloxyhexyl) phosphate, (meth)acryloxyoctyl phosphate, bis((meth)acryloxyoctyl) phosphate, (meth)acryloxydecyl phosphate, bis((meth)acryloxydecyl) phosphate, caprolactone methacrylate phosphate, citric acid di-or tri-methacrylate, poly(meth)acrylated oligomaleic acid, poly(meth)acrylated polymaleic acid, poly(meth)acrylated poly(meth)acrylic acid, poly(meth)acrylated polycarboxyl-polyphosphonic acid, poly(meth)acrylated polychlorophosphoric acid, poly(meth)acrylated polysulfonate, poly (meth)acrylated polyboric acid, and the like. Derivatives of these hardenable components bearing an acid moiety that can readily react e.g. with water to form the specific examples mentioned above, like acid halides or anhydrides are also contemplated.

Also monomers, oligomers, and polymers of unsaturated carboxylic acids such as (meth)acrylic acids, aromatic (meth)acrylated acids (e.g., methacrylated trimellitic acids), and anhydrides thereof can be used.

Some of these compounds can be obtained, e.g., as reaction products between isocyanatoalkyl (meth)acrylates and carboxylic acids. Additional compounds of this type having both acid-functional and ethylenically unsaturated components are desoikcribed in U.S. Pat. No. 4,872,936 (Engelbrecht) and U.S. Pat. No. 5,130,347 (Mitra). A wide variety of such compounds containing both the ethylenically unsaturated and acid moieties can be used. If desired, mixtures of such compounds can be used.

Using (meth)acrylate functionalized polyalkenoic acids is often preferred as those components were found to be useful to improve properties like adhesion to hard dental tissue, formation of a homogeneous layer, viscosity, or moisture tolerance.

According to one embodiment, the composition contains (meth)acrylate functionalized polyalkenoic acids, for example, AA:ITA:IEM (copolymer of acrylic acid:itaconic acid with pendent methacrylates).

These components can be made by reacting e.g. an AA:ITA copolymer with 2-isocyanatoethyl methacrylate to convert at least a portion of the acid groups of the copolymer to pendent methacrylate groups. Processes for the production of these components are described, e.g., in Example 11 of U.S. Pat. No. 5,130,347 (Mitra)); and those recited in U.S. Pat. No. 4,259,075 (Yamauchi et al.), U.S. Pat. No. 4,499,251 (Omura et al.), U.S. Pat. No. 4,537,940 (Omura et al.), U.S. Pat. No. 4,539,382 (Omura et al.), U.S. Pat. No. 5,530,038 (Yamamoto et al.), U.S. Pat. No. 6,458,868 (Okada et al.), and EP 0 712 622 A1 (Tokuyama Corp.) and EP 1 051 961 A1 (Kuraray Co., Ltd.).

Mixtures of two, three or more of the polymerizable monomers (2) can be used, if desired.

The polymerizable monomer with acidic moieties (2) can be present in the following amounts:
Lower limit: at least about 0 or at least about 0.1 or at least about 1 wt.-%,
Upper Limit: up to about 60 or up to about 50 or up to about 40 wt.-%,
Range: from about 0 to about 60 or from about 0.1 to about 50 or from about 1 to about 40 wt.-%,
wt.-% with respect to the amount of the whole composition.

The composition described in the present text may optionally also comprise a polymerizable monomer (3) without an acidic moiety being different from polymerizable monomer (1).

If present, the polymerizable monomer (3) forms a further component of the hardenable resin matrix.

The nature and structure of polymerizable monomer (3) is not particularly limited, unless the desired result cannot be achieved.

This component is typically a free-radically polymerizable material, including ethylenically unsaturated monomer, monomers or oligomers or polymers.

Suitable polymerizable components can be characterized by the following formula:

$A_n\text{-}B\text{-}A_m$ with A being an ethylenically unsaturated group, such as a (meth)acryl moiety,
B being selected from (i) linear or branched C1 to C12 alkyl, optionally substituted with other functional groups (e.g. halogenides (including Cl, Br, I), OH or mixtures thereof) (ii) C6 to C12 aryl, optionally substituted with other functional groups (e.g. halogenides, OH or mixtures thereof), or (iii) organic group having 4 to 20 carbon atoms bonded to one another by one or more ether, thioether, ester, thioester, thiocarbonyl, amide, urethane, carbonyl and/or sulfonyl linkages,
m, n being independently selected from 0, 1, 2, 3, 4, 5 or 6 with the proviso that n+m is greater 0, that is that at least one A group is present.

Such polymerizable materials include mono-, di- or polyacrylates and methacrylates such as methyl acrylate, methyl methacrylate, ethyl (meth)acrylate, isopropyl (meth)acrylate, n-hexyl (meth)acrylate, stearyl (meth)acrylate, allyl (meth)acrylate, glycerol di(meth)acrylate, the diurethane dimethacrylate called UDMA (mixture of isomers, e.g. Rohm Plex 6661-0) being the reaction product of 2-hydroxyethyl methacrylate (HEMA) and 2,2,4-trimethylhexamethylene diisocyanate (TMDI), glycerol tri(meth)acrylate, ethyleneglycol di(meth)acrylate, diethyleneglycol di(meth)acrylate, triethyleneglycol di(meth)acrylate, 1,3-propanediol diacrylate, 1,3-propanediol dimethacrylate, 1,6 hexanediol di(meth)acrylate, 1,10 decanediol di(meth)acrylate, 1,12 dodecanediol di(meth)acrylate, trimethylolpropane tri(meth)acrylate, 1,2,4-butanetriol tri(meth)acrylate, 1,4-cyclohexanediol di(meth)acrylate, pentaerythritol tri (meth)acrylate, pentaerythritol tetraacrylate, pentaerythritol tetramethacrylate, sorbitol hexa(meth)acrylate, bis[1-(2-(meth)acryloxy)]-p-ethoxyphenyldimethylmethane, and trishydroxyethyl-isocyanurate trimethacrylate; the bis-acrylates and bis-methacrylates of polyethylene glycols of molecular weight 200-500, copolymerizable mixtures of acrylated monomers (see e.g. U.S. Pat. No. 4,652,274), and acrylated oligomers (see e.g. U.S. Pat. No. 4,642,126); and vinyl compounds such as styrene, divinyl succinate, divinyl adipate and divinylphthalate; polyfunctional (meth)acrylates comprising urethane, urea or amide groups. Mixtures of two or more of these free radically polymerizable materials can be used if desired.

These ethylenically unsaturated monomers can be employed in the dental composition(s) either alone or in combination with other ethylenically unsaturated monomers.

Monomers comprising a hydroxyl moiety can also be added. Suitable compounds include 2-hydroxyethyl (meth)acrylate (HEMA), 2- or 3-hydroxypropyl (meth)acrylate, 4-hydroxybutyl (meth)acrylate, 5-hydroxypentyl (meth)acrylate, 6-hydroxyhexyl (meth)acrylate, 10-hydroxydecyl (meth)acrylate, dialkylene glycol mono(meth)acrylate, for example, diethylene glycol mono(meth)acrylate, triethylene glycol mono(meth)acrylate, tetraethylene glycol mono (meth)acrylate, polyethylene glycol mono(meth)acrylate, dipropylene glycol mono(meth)acrylate, polypropylene glycol mono(meth)acrylate, and further 1,2- or 1,3- and 2,3-dihydroxypropyl (meth)acrylate, 2-hydroxypropyl-1,3-di (meth)acrylate, 3-hydroxypropyl-1,2-di(meth)acrylate, N-(meth)acryloyl-1,2-dihydroxypropylamine, N-(meth)acryloyl-1,3-dihydroxypropylamine, adducts of phenol and glycidyl (meth)acrylate, for example, 1-phenoxy-2-hydroxypropyl (meth)acrylate, 1-naphthoxy-2-hydroxypropyl (meth)acrylate, bisphenol A diglycidyl (meth)acrylate and the like, 2-hydroxyethyl (meth)acrylate, 2-hydroxypropyl (meth)acrylate and 2,3-dihydroxypropyl (meth)acrylate are particularly preferable.

If desired, mixtures of one or more of these components can be used.

In addition or besides those components, other hardenable components which can be added include oligomeric or polymeric compounds, such as polyester urethane (meth) acrylates, polyether urethane (meth)acrylates, polycarbonate urethane (meth)acrylates and poly(meth)acrylate urethane (meth)acrylates. The molecular weight of these compounds is typically less than 20,000 g/mol, particularly less than 15,000 g/mol and in particular less than 10,000 g/mol.

Adding these components may be used to adjust the rheological properties.

Mixtures of two, three or more of the polymerizable monomers (3) can be used, if desired.

The polymerizable monomer (3) can be present in the following amounts:
Lower limit: at least about 0 or at least about 1 or at least about 5 wt.-%,
Upper Limit: up to about 70 or up to about 60 or up to about 50 wt.-%,
Range: from about 0 to about 70 or from about 1 to about 60 or from about 5 to about 50 wt.-%,
wt.-% with respect to the amount of the whole composition.

The composition described in the present text also comprises an initiator being suitable to initiate curing or hardening of the composition, in particular the polymerizable monomer(s) contained in the resin matrix of the composition.

If more than one initiator component is required, the initiator is also referred to as initiator system.

The nature of the initiator is not particularly limited, unless the desired result cannot be achieved.

The initiator system can comprise systems which are capable of initiating polymerization via radiation (i.e. radiation curing), heat (i.e. heat curing), redox reaction (i.e. redox-curing) or a combination thereof.

A class of initiators capable of initiating polymerization of the hardenable components of the resin matrix which contain free radically active functional groups includes free radical-generating photoinitiators, optionally combined with a photosensitizer or accelerator.

Such initiators typically can be capable of generating free radicals for addition polymerization upon exposure to light energy having a wavelength between about 200 and about 700 nm.

Initiator components which can undergo an alpha-cleavage are sometimes preferred.

Using acylphosphine oxides as initiators or part of the initiator system was found to be particularly useful.

Suitable acylphosphine oxides can be characterized by the following formula

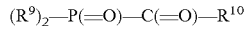

wherein each $R^9$ individually can be a hydrocarbyl group such as alkyl, cycloalkyl, aryl, and aralkyl, any of which can be substituted with a halo-, alkyl- or alkoxy-group, or the two $R^9$ groups can be joined to form a ring along with the phosphorous atom, and wherein $R^{10}$ is a hydrocarbyl group, an S-, O-, or N-containing five- or six-membered heterocyclic group, or a —Z—C(=O)—P(=O)—$(R^9)_2$ group, wherein Z represents a divalent hydrocarbyl group such as alkylene or phenylene having from 2 to 6 carbon atoms.

Suitable systems are also described e.g. in U.S. Pat. No. 4,737,593, the content of which is herewith incorporated by reference.

Preferred acylphosphine oxides useful in the invention are those in which the $R^9$ and $R^{10}$ groups are phenyl or lower alkyl- or lower alkoxy-substituted phenyl. By "lower alkyl" and "lower alkoxy" is meant such groups having from 1 to 4 carbon atoms. Most preferably, the acylphosphine oxide is 2,4,6-trimethylbenzoyl diphenyl phosphine oxide (Lucirin™ TPO, BASF).

Suitable bisacylphosphine oxides can also be described by the following formula

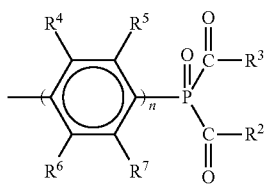

wherein n is 1 or 2, and $R^4$, $R^5$, $R^6$ and $R^7$ are H, C1-4 alkyl, C1-4 alkoxyl, F, Cl or Br; $R^2$ and $R^3$, which are the same or different, stand for a cyclohexyl, cyclopentyl, phenyl, naphthyl, or biphenylyl radical, a cyclopentyl, cyclohexyl, phenyl, naphthyl, or biphenylyl radical substituted by F, Cl, Br, I, C1-4 alkyl and/or C1-4 alkoxyl, or an S or N-containing 5-membered or 6-membered heterocyclic ring; or $R^2$ and $R^3$ are joined to form a ring containing from 4 to 10 carbon atoms and being optionally substituted by 1 to 6 C1-4 alkyl radicals.

More specific examples include: bis-(2,6-dichlorobenzoyl)phenylphosphine oxide, bis-(2,6-dichlorobenzoyl)-2,5-dimethylphenylphosphine oxide, bis-(2,6-dichlorobenzoyl)-4-ethoxyphenylphosphine oxide, bis-(2,6-dichlorobenzoyl)-4-biphenylylphosphine oxide, bis-(2,6-dichlorobenzoyl)-4-propylphenylphosphine oxide, bis-(2,6-dichlorobenzoyl)-2-naphthylphosphine oxide, bis-(2,6-dichlorobenzoyl)-1-napthylphosphine oxide, bis-(2,6-dichlorobenzoyl)-4-chlorophenylphosphine oxide, bis-(2,6-dichlorobenzoyl)-2,4-dimethoxyphenylphosphine oxide, bis-(2,6-dichlorobenzoyl)decylphosphine oxide, bis-(2,6-dichlorobenzoyl)-4-octylphenylphosphine oxide, bis-(2,6-dimethoxybenzoyl)-2,5-dimethylphenylphosphine oxide, bis-(2,6-dimethoxybenzoyl)phenylphosphine oxide, bis-(2,4,6-trimethylbenzoyl)-2,5-dimethylphenylphosphine oxide, bis-(2,6-dichloro-3,4,5-trimethoxybenzoyl)-2,5-dimethylphenylphosphine oxide, bis-(2,6-dichloro-3,4,5-trimethoxybenzoyl)-4-ethoxyphenylphosphine oxide, bis-(2-methyl-1-naphthoyl)-2,5-dimethylphenylphosphine oxide, bis-(2-methyl-1-naphthoyl)phenylphosphine oxide. bis-(2-methyl-1-naphthoyl)-4-biphenylylphosphine oxide, bis-(2-methyl-1-naphthoyl)-4-ethoxyphenylphosphine oxide, bis-(2-methyl-1-naphthoyl)-2-naphthylphosphine oxide, bis-(2-methyl-1-naphthoyl)-4-propylphenylphosphine oxide, bis-(2-methyl-1-naphthol)-2,5-dimethylphosphine oxide, bis-(2-methoxy-1-naphthoyl)-4-ethoxyphenylphosphine oxide, bis-(2-methoxy-1-naphthoyl)-4-biphenylylphosphine oxide, bis-(2-methoxy-1-naphthoyl)-2-naphthylphosphine oxide and bis-(2-chloro-1-naphthoyl)-2,5-dimethylphenylphosphine oxide.

The acylphosphine oxide bis(2,4,6-trimethylbenzoyl)phenyl phosphine oxide (IRGACURE™ 819, Ciba Specialty Chemicals, Tarrytown, N.Y.) is sometimes preferred.

Tertiary amine reducing agents may be used in combination with an acylphosphine oxide. Illustrative tertiary amines useful in the invention include ethyl 4-(N,N-dimethylamino)benzoate (EDMAB) and N,N-dimethylaminoethyl methacrylate (DMAEMA).

Commercially-available phosphine oxide photoinitiators capable of free-radical initiation when irradiated at wavelengths of greater than 400 nm to 1200 nm include a 25:75 mixture, by weight, of bis(2,6-dimethoxybenzoyl)-2,4,4-trimethylpentyl phosphine oxide and 2-hydroxy-2-methyl-1-phenylpropan-1-one (IRGACURE™ 1700, Ciba Specialty Chemicals), 2-benzyl-2-(N,N-dimethylamino)-1-(4-morpholinophenyl)-1-butanone (IRGACURE™ 369, Ciba Specialty Chemicals), bis(η5-2,4-cyclopentadien-1-yl)-bis(2,6-difluoro-3-(1H-pyrrol-1-yl)phenyl) titanium (IRGACURE™ 784 DC, Ciba Specialty Chemicals), a 1:1 mixture, by weight, of bis(2,4,6-trimethylbenzoyl)phenyl phosphine oxide and 2-hydroxy-2-methyl-1-phenylpropane-1-one (DAROCUR™ 4265, Ciba Specialty Chemicals), and ethyl-2,4,6-trimethylbenzylphenyl phosphinate (LUCIRIN™ LR8893X, BASF Corp., Charlotte, N.C.).

A variety of visible or near-IR photoinitiator systems may also be used for photopolymerization of free-radically polymerizable materials.

For example, a photoinitiation system can be used selected from systems which initiate polymerization via a two component system of an amine and an α-diketone. Such systems are described e.g. in U.S. Pat. No. 4,071,424 and WO 2009151957, which are herein incorporated by reference.

Alternatively, the resin can be combined with a three components or ternary photoinitiator system. Suitable systems are described in U.S. Pat. No. 5,545,676 and WO 2009151957, which are incorporated herein by reference.

In the ternary photoinitiator system, the first component is an iodonium salt, i.e., a diaryliodonium salt. The iodonium salt is preferably soluble in the monomer and shelf-stable (i e., does not spontaneously promote polymerization) when dissolved therein in the presence of the sensitizer and donor. Accordingly, selection of a particular iodonium salt may depend to some extent upon the particular monomer, polymer or oligomer, sensitizer and donor chosen. Suitable iodonium salts are described in U.S. Pat. Nos. 3,729,313, 3,741,769, 3,808,006, 4,250,053 and 4,394,403, the iodonium salt disclosures of which are incorporated herein by reference. The iodonium salt can be a simple salt (e.g., containing an anion such as Cl$^-$, Br$^-$, I$^-$ or $C_4H_5$ $SO_3^-$) or a metal complex salt (e.g., containing $SbF_5OH^-$ or $AsF_6^-$). Mixtures of iodonium salts can be used if desired. Preferred iodonium salts include diphenyliodonium salts such as diphenyliodonium chloride, diphenyliodonium hexafluorophosphate and diphenyliodonium tetrafluoroborate.

The second component in a ternary photoinitiator system is a sensitizer. The sensitizer desirably is soluble in the monomer, and is capable of light absorption somewhere within the range of wavelengths of greater than 400 to 1200 nanometers, more preferably greater than 400 to 700 nanometers and most preferably greater than 400 to about 600 nanometers. The sensitizer may also be capable of sensitizing 2-methyl-4,6-bis(trichloromethyl)-s-triazine, using the test procedure described in U.S. Pat. No. 3,729,313, which is incorporated herein by reference. Preferably, in addition to passing this test, a sensitizer is also selected based in part upon shelf stability considerations. Accordingly, selection of a particular sensitizer may depend to some extent upon the particular monomer, oligomer or polymer, iodonium salt and donor chosen.

Suitable sensitizers can include compounds in the following categories: ketones, coumarin dyes (e.g., ketocoumarins), xanthene dyes, acridine dyes, thiazole dyes, thiazine dyes, oxazine dyes, azine dyes, aminoketone dyes, porphyrins, aromatic polycyclic hydrocarbons, p-substituted aminostyryl ketone compounds, aminotriaryl methanes, merocyanines, squarylium dyes and pyridinium dyes. Ketones (e.g., monoketones or alpha-diketones), ketocoumarins, aminoarylketones and p-substituted aminostyryl ketone compounds are preferred sensitizers. For applications requiring high sensitivity, it is preferred to employ a sensitizer containing a julolidinyl moiety. For applications requiring deep cure (e.g., cure of highly-filled composites), it is preferred to employ sensitizers having an extinction coefficient below about 1000, more preferably below about 100, at the desired wavelength of irradiation for photopolymerization. Alternatively, dyes that exhibit reduction in light absorption at the excitation wavelength upon irradiation can be used.

For example, a preferred class of ketone sensitizers has the formula: ACO(X)$_b$ B, where X is CO or CR$^5$ R$^6$, where R$^5$ and R$^6$ can be the same or different, and can be hydrogen, alkyl, alkaryl or aralkyl, b is zero or one, and A and B can be the same or different substituted (having one or more non-interfering substituents) or unsubstituted aryl, alkyl, alkaryl, or aralkyl groups, or together A and B can form a cyclic structure which can be a substituted or unsubstituted cycloaliphatic, aromatic, heteroaromatic or fused aromatic ring.

Suitable ketones of the above formula include monoketones (b=0) such as 2,2-,4,4- or 2,4-dihydroxybenzophenone, di-2-pyridyl ketone, di-2-furanyl ketone, di-2-thiophenyl ketone, benzoin, fluorenone, chalcone, Michler's ketone, 2-fluoro-9-fluorenone, 2-chlorothioxanthone, acetophenone, benzophenone, 1- or 2-acetonaphthone, 9-acetylanthracene, 2-, 3- or 9-acetylphenanthrene, 4-acetylbiphenyl, propiophenone, n-butyrophenone, valerophenone, 2-, 3- or 4-acetylpyridine, 3-acetylcoumarin and the like. Suitable diketones include aralkyldiketones such as anthraquinone, phenanthrenequinone, o-, m- and p-diacetylbenzene, 1,3-, 1,4-, 1,5-, 1,6-, 1,7- and 1,8-diacetylnaphthalene, 1,5-,1,8- and 9,10-diacetylanthracene, and the like. Suitable alpha-diketones (b=1 and X=CO) include 2,3-butanedione, 2,3-pentanedione, 2,3-hexanedione, 3,4-hexanedione, 2,3-heptanedione, 3,4-heptanedione, 2,3-octanedione, 4,5-octanedione, benzil, 2,2'-3 3'- and 4,4'-dihydroxylbenzil, furil, di-3,3'-indolylethanedione, 2,3-bornanedione (camphorquinone), biacetyl, 1,2-cyclohexanedione, 1,2-naphthaquinone, acenaphthaquinone, and the like.

The third component of a ternary initiator system is a donor. Preferred donors include, for example, amines (including aminoaldehydes and aminosilanes), amides (including phosphoramides), ethers (including thioethers), ureas (including thioureas), ferrocene, sulfinic acids and their salts, salts of ferrocyanide, ascorbic acid and its salts, dithiocarbamic acid and its salts, salts of xanthates, salts of ethylene diamine tetraacetic acid and salts of tetraphenylboronic acid. The donor can be unsubstituted or substituted with one or more non-interfering substituents. Particularly preferred donors contain an electron donor atom such as a nitrogen, oxygen, phosphorus, or sulfur atom, and an abstractable hydrogen atom bonded to a carbon or silicon atom alpha to the electron donor atom. A wide variety of donors is disclosed in U.S. Pat. No. 5,545,676, which is incorporated herein by reference.

Another free-radical initiator system that can alternatively be used in the dental compositions described in the present text is the class of ionic dye counterion complex initiators comprising a borate anion and a complementary cationic dye.

Borate salt photoinitiators are described, for example, in U.S. Pat. Nos. 4,772,530, 4,954,414, 4,874,450, 5,055,372, and 5,057,393, the disclosures of which are incorporated herein by reference.

Borate anions useful in these photointiators generally can be of the formula R$^1$R$^2$R$^3$R$^4$B$^-$, wherein R$^1$, R$^2$, R$^3$, and R$^4$ independently can be alkyl, aryl, alkaryl, allyl, aralkyl, alkenyl, alkynyl, alicyclic and saturated or unsaturated heterocyclic groups. Preferably, R$^2$, R$^3$, and R$^4$ are aryl groups and more preferably phenyl groups, and R$^1$ is an alkyl group and more preferably a secondary alkyl group.

Cationic counterions can be cationic dyes, quaternary ammonium groups, transition metal coordination complexes, and the like. Cationic dyes useful as counterions can be cationic methine, polymethine, triarylmethine, indoline, thiazine, xanthene, oxazine or acridine dyes. More specifically, the dyes may be cationic cyanine, carbocyanine, hemicyanine, rhodamine, and azomethine dyes. Specific examples of useful cationic dyes include Methylene Blue, Safranine O, and Malachite Green. Quaternary ammonium groups useful as counterions can be trimethylcetylammonium, cetylpyridinium, and tetramethylammonium. Other organophilic cations can include pyridinium, phosphonium, and sulfonium.

Photosensitive transition metal coordination complexes that may be used include complexes of cobalt, ruthenium, osmium, zinc, iron, and iridium with ligands such as pyridine, 2,2'-bipyridine, 4,4'-dimethyl-2,2'-bipyridine, 1,10-phenanthroline, 3,4,7,8-tetramethylphenanthroline, 2,4,6-tri (2-pyridyl-s-triazine) and related ligands.

Yet another alternative class of initiators capable of initiating polymerization of free radically active functional groups includes conventional chemical initiator systems such as a combination of a peroxide and an activator such as an amine. These initiators, which rely upon a thermal redox reaction, are often referred to as "auto-cure catalysts." They are typically supplied as two-part systems in which the reactants are stored apart from each other and then combined immediately prior to use.

In particular, compounds such as lauroyl peroxide, benzoyl peroxide and p-chlorobenzoyl peroxide and p-methylbenzoyl peroxide can be considered as organic peroxide compounds.

Suitable as activators are, for example, tertiary aromatic amines, such as the N,N-bis-(hydroxyalkyl)-3,5-xylidines known from U.S. Pat. No. 3,541,068 as well as N,N-bis-(hydroxyalkyl)-3,5-di-t-butylanilines, in particular N,N-bis-([beta]-oxybutyl)-3,5-di-t-butylaniline as well as N,N-bis-(hydroxyalkyl)-3,4,5-trimethylaniline.

Well-suited activators are also the barbituric acids and barbituric acid derivatives as described in US 2003/008967, DE 14 95 520 as well as the malonyl sulfamides described in U.S. Pat. No. 4,544,742 (corresponding to EP 0 059 451). Preferred malonyl sulfamides are 2,6-dimethyl-4-isobutyl-malonyl sulfamide, 2,6-diisobutyl-4-propylmalonyl sulfamide, 2,6-dibutyl4-propylmalonyl sulfamide, 2,6-dimethyl4-ethylmalonyl sulfamide and 2,6-dioctyl4-isobutyl malonyl sulfamide.

For further acceleration, the polymerization is in this case preferably carried out in the presence of heavy-metal compounds and ionogenic halogen or pseudohalogen. The heavy metal is suitably used in the form of soluble organic compounds Likewise, the halide and pseudohalide ions are suitably used in the form of soluble salts, as examples there can be named the soluble amine hydrochlorides as well as quarternary ammonium chloride compounds. Suitable accelerators are in particular metals from the iron or copper group, preferably copper and iron complexes and in particular copper complexes. The heavy metal is preferably employed in the form of soluble organic compounds. Suitable are, for example, iron carboxylates, copper carboxylates, iron procetonate, copper procetonate, copper naphthenate, copper acetate and iron naphthenate.

In a further alternative, heat may be used to initiate the hardening, or polymerization, of free radically active groups. Examples of heat sources suitable for the dental materials described in the present text include inductive, convective, and radiant. Thermal sources should be capable of generating temperatures of at least 40° C. to 15° C. This procedure is sometime preferred for initiating polymerization of materials occurring outside of the oral environment.

Yet another alternative class of initiators capable of initiating polymerization of free radically active functional groups that are useful for the dental materials as described in the present text are those that include free radical-generating thermal initiators. Examples include peroxides such as, for example, benzoyl peroxide and lauryl peroxide, and azo compounds such as, for example, 2,2-azobis-isobutyronitrile (AIBN).

If the color of the cured composition matters, an initiator system which does not lead to undesired discoloration should be used.

The initiator or initiator system is typically contained in the following amounts:
 Lower limit: at least about 0.1 or at least about 0.2 or at least about 0.3 wt.-%,
 Upper Limit: up to about 10 or up to about 8 or up to about 6 wt.-%,
 Range: from about 0.1 to about 10 or from about 0.2 to about 8 or from about 0.3 to about 6 wt.-%,
wt.-% with respect to the amount of the whole composition.

The composition described in the present text also comprises filler.

Adding a filler can be beneficial e.g. for adjusting the rheological properties like viscosity. The content of the filler also typically influences the physical properties of the composition after hardening, like hardness or flexural strength.

The chemical nature of the filler(s) is not particularly limited unless the intended purpose cannot be achieved.

The size of the filler particles should be such that a homogeneous mixture with the hardenable component forming the resin matrix can be obtained.

The particle size of the filler may be in a range from about 0.001 to about 10 μm.

The filler(s) typically comprise non acid reactive fillers. A non-acid reactive filler is a filler which does not undergo an acid/base reaction with an acid.

Useful non acid reactive fillers include fumed silica, quartz, ground glasses, non-water-soluble fluorides such as $CaF_2$, silica gels such as silicic acid, in particular pyrogenic silicic acid and granulates thereof, cristobalite, calcium silicate, zirconium silicate, zeolites, including the molecular sieves, barium sulphate, yttrium fluoride.

Suitable fumed silicas include for example, products sold under the tradename Aerosil™ series OX-50, -130, -150, and -200, Aerosil R8200 available from Degussa AG, (Hanau, Germany), CAB-O-SIL™ M5 available from Cabot Corp (Tuscola, Ill.), and HDK types, e.g. HDK-H 2000, HDK H15; HDK H18, HDK H20 and HDK H30 available from Wacker.

The average surface area of the silica particles is preferably greater than about 15 $m^2/g$ more preferably greater than about 30 $m^2/g$.

Filler(s) which can also be used include nano-sized fillers such as nano-sized silica. Suitable nano-sized particles typically have a mean particle size in the range of about 5 to about 80 nm.

Preferred nano-sized silicas are commercially available from Nalco Chemical Co. (Naperville, Ill.) under the product designation NALCO COLLOIDAL SILICAS (for example, preferred silica particles can be obtained from using NALCO products 1040, 1042, 1050, 1060, 2327 and 2329), Nissan Chemical America Company, Houston, Tex. (for example, SNOWTEX-ZL, -OL, -O, -N, -C, -20L, -40, and -50); Admatechs Co., Ltd., Japan (for example, SX009-MIE, SX009-MIF, SC1050-MJM, and SC1050-MLV); Grace GmbH & Co. KG, Worms, Germany (for example, those available under the product designation LUDOX, e.g., P-W50, P-W30, P-X30, P-T40 and P-T40AS); Akzo Nobel Chemicals GmbH, Leverkusen, Germany (for example, those available under the product designation LEVASIL, e.g., 50/50%, 100/45%, 200/30%, 200A/30%, 200/40%, 200A/40%, 300/30% and 500/15%), and Bayer Material-Science AG, Leverkusen, Germany (for example, those available under the product designation DISPERCOLL S, e.g., 5005, 4510, 4020 and 3030).

Surface-treating the nano-sized silica particles before loading into the dental material can provide a more stable dispersion in the resin. Preferably, the surface-treatment stabilizes the nano-sized particles so that the particles will be well dispersed in the hardenable resin and results in a substantially homogeneous composition. Furthermore, it is preferred that the silica be modified over at least a portion of its surface with a surface treatment agent so that the stabilized particle can copolymerize or otherwise react with the hardenable resin during curing.

Thus, the silica particles as well as other suitable non acid-reactive fillers can be treated with a resin-compatibilizing surface treatment agent.

Particularly preferred surface treatment or surface modifying agents include silane treatment agents capable of polymerizing with a resin. Preferred silane treatment agent include gamma-methacryloxylpropyltrimethoxysilane, available commercially under the trade designation A-174, available commercially from Witco OSi Specialties (Danbury, Conn.) and gamma-glycidoxypropyltrimethoxy silane, a product available under the trade designation G6720, available from United Chemical Technologies (Bristol, Pa.).

Alternatively a combination of surface modifying agents can be useful, wherein at least one of the agents has a functional group co-polymerizable with a hardenable resin. For example, the polymerizing group can be ethylenically unsaturated or a cyclic function subject to ring opening polymerization. An ethylenically unsaturated polymerizing group can be, for example, an acrylate or methacrylate, or vinyl group. A cyclic functional group subject to ring opening polymerization generally contains a heteroatom such as oxygen, sulfur or nitrogen, and preferably is a 3-membered ring containing oxygen such as an epoxide. Other surface modifying agents which do not generally react with hardenable resins can be included to enhance dispersibility or rheological properties. Examples of silane of this type include, for example, alkyl or aryl polyethers, alkyl, hydroxy alkyl, hydroxy aryl, or amino alkyl functional silanes.

Besides an inorganic material the filler(s) can also be based on an organic material. Examples of suitable organic filler particles include filled or unfilled pulverized polycarbonates, poly(meth)acrylates, polyepoxides, and the like.

If desired, the measurement of the particle size of the filler particles can be done with a TEM (transmission electron microscopy) method, whereby a population is analyzed to obtain an average particle diameter.

A preferred method for measuring the particle diameter can be described is as follows: Samples approximately 80 nm thick are placed on 200 mesh copper grids with carbon stabilized formvar substrates (SPI Supplies—a division of Structure Probe, Inc., West Chester, Pa.). A transmission electron micrograph (TEM) is taken, using JEOL 200CX (JEOL, Ltd. of Akishima, Japan and sold by JEOL USA, Inc.) at 200 Kv. A population size of about 50-100 particles can be measured and an average diameter is determined.

The amount of filler to be used in the filler matrix usually depends on the purpose for which the composition should be used.

The filler is typically used in the following amounts:
Lower limit: at least about 20 or at least about 30 or at least about 40 wt.-%,
Upper Limit: up to about 95 or up to about 90 or up to about 85 wt.-%,
Range: from about 20 to about 95 or from about 30 to about 90 or from about 40 to about 85 wt.-%,
wt.-% with respect to the amount of the whole composition.

Besides the above mentioned components, the dental composition described in the present text may further contain one, two or more of the following additives:

x-ray visible particles,
pigments,
photobleachable colorants,
fluoride release agents,
stabilizers,
retarders,
and mixtures thereof.

Suitable x-ray visible particles which may be present include particles of metal oxides like the oxides of yttrium, ytterbium, strontium, barium, zirconium, hafnium, niobium, tantalum, tungsten, bismuth, molybdenum, tin, zinc, lanthanide elements (i.e. elements having atomic numbers ranging from 57 to 71, inclusive), cerium and combinations thereof. Most preferably, the oxides of heavy metals having an atomic number greater than 30, but less than 72 are optionally included in the materials of the invention. Particularly preferred radiopacifying metal oxides include lanthanum oxide, zinc oxide, tin oxide, zirconium oxide, yttrium oxide, ytterbium oxide, barium oxide, strontium oxide, cerium oxide, and combinations thereof.

Examples of pigments, which can be used include titanium dioxide or zinc sulphide (lithopones), red iron oxide 3395, Bayferrox 920 Z Yellow, Neazopon Blue 807 (copper phthalocyanine-based dye) or Helio Fast Yellow ER. These additives may be used for individual coloring of the dental compositions.

Examples of photobleachable colorants which can be present include Rose Bengal, Methylene Violet, Methylene Blue, Fluorescein, Eosin Yellow, Eosin Y, Ethyl Eosin, Eosin bluish, Eosin B, Erythrosin B, Erythrosin Yellowish Blend, Toluidine Blue, 4',5'-Dibromofluorescein and blends thereof. Further examples of photobleachable colorants can be found in U.S. Pat. No. 6,444,725. The color of the compositions of the invention may be additionally imparted by a sensitizing compound.

Examples of fluoride release agents which can be present include naturally occurring or synthetic fluoride minerals. These fluoride sources can optionally be treated with surface treatment agents.

Further additives, which can be added, include stabilizers, especially free radical scavengers such as substituted and/or unsubstituted hydroxyaromatics (e.g. butylated hydroxytoluene (BHT), hydroquinone, hydroquinone monomethyl ether (MEHQ), 3,5-di-tert-butyl-4-hydroxyanisole (2,6-di-tert-butyl-4-ethoxyphenol), 2,6-di-tert-butyl-4-(dimethylamino)methylphenol or 2,5-di-tert-butyl hydroquinone, 2-(2'-hydroxy-5'-methylphenyl)-2H-benzotriazole, 2-(2'-hydroxy-5'-t-octylphenyl)-2H-benzotriazole, 2-hydroxy-4-methoxybenzophenone (UV-9), 2-(2'-hydroxy-4',6'-di-tert-pentylphenyl)-2H-benzotriazole, 2-hydroxy-4-n-octoxybenzophenone, 2-(2'-hydroxy-5'-methacryloxyethylphenyl)-2H-benzotriazole, phenothiazine, and HALS (hindered amine light stabilizers).

Further additives, which can be added, include retarders, (such as 1,2-diphenylethylene), plasticizers (including polyethylene glycol derivatives, polypropylene glycols, low-molecular-weight polyesters, dibutyl, dioctyl, dinonyl and diphenyl phthalate, di(isononyl) adipate), tricresyl phosphate, paraffin oils, glycerol triacetate, bisphenol A diacetate, ethoxylated bisphenol A diacetate, and silicone oils), flavorants, anti-microbials, fragrance, agents that impart fluorescence and/or opalescence and fluoride releasing materials.

There is no need for the additive(s) to be present. The additive(s) may be present in the following amounts:
Lower limit: at least about 0 or at least about 0.1 or at least about 1 wt.-%, Upper Limit: up to about 10 or up to about 8 or up to about 5 wt.-%,
Range: from about 0 to about 10 or from about 0.1 to about 8 or from about 1 to about 5 wt.-%,
wt.-% with respect to the amount of the whole composition.

According to a further embodiment, the dental composition described in the present text is described as follows:
Polymerizable monomer (1): from about 1 to about 75 wt.-%, or from about 5 to about 70 wt.-%, or from about 10 to about 65 wt.-%;
Polymerizable monomer (2): from about 0 to about 60 wt.-%, or from about 0.1 to about 50 wt.-%, or from about 1 to about 40 wt.-%;
Polymerizable monomer (3): from 0 to about 70 wt.-%, or from about 1 to about 60 wt.-%, or from about 5 to about 50 wt.-%;
Initiator(s): from about 0.1 to about 10 wt.-%, or from about 0.2 to about 8 wt.-%, or from about 0.3 to about 6 wt.-%;
Filler(s): from about 20 to about 95 wt.-%, or from about 30 to about 90 wt.-%, or from about 40 to about 85 wt.-%;
Additive(s): from 0 to about 10 wt.-%, or from about 0.1 to about 8 wt.-%, or from about 1 to about 5 wt.-%;
wt.-% with respect to the weight of the whole composition.

The dental composition described in the present text can be produced as follows:
providing the respective components,
mixing the components.

Mixing can be achieved by using any means known to the practitioner. That is, the adhesive composition can be prepared in an one-pot synthesis simply by putting the respective components together and mixing them.

If desired, the production process is performed under save light conditions to avoid an undesired polymerization of the composition.

The hardenable dental composition described in the present text is typically stored in a container until use. Depending on the formulation and the curing status, various containers can be used.

The composition can be provided in the form of a one-component system or as a two-component system. This typically depends on the initiator system chosen. If the composition is redox curable or curing, it is usually provided as a two-component system.

If the dental composition is provided as a one-component system, it can be stored in a container having only one chamber such as a compule or screw tube.

A compule typically has a cylindrical housing with a front and a rear end and a nozzle. The rear end of the housing is usually sealed with a movable piston. Typically, the dental composition is dispensed out of the compule or container using an applier having a movable plunger (e.g. an application device having the shape of a caulk gun). Examples of suitable compules or containers are described in U.S. Pat. No. 5,624,260, EP 1 340 472 A1, US 2007/0172789 A1, U.S. Pat. Nos. 5,893,714 and 5,865,803, the content of which with regard to the description of compules or containers is herewith incorporated by reference.

Suitable two-component systems for storage include two-barrel cartridges.

Suitable two-component systems are described e.g. in US 2007/0090079 or U.S. Pat. No. 5,918,772. The content of these documents with respect to the description of the vial or bottle is herewith incorporated by reference. Cartridges which can be used are also commercially available from SulzerMixpac AG (Switzerland).

The volume of each compartment of the two-barrel cartridges is typically in the range from about 0.1 to about 100 ml or from about 0.5 to about 50 ml or from about 1 to about 30 ml.

The volume ratio of compartment (I) to compartment (II) is typically within a range of about 1:1 to about 10:1.

Static mixing tips which can be used for mixing the compositions contained in the compartments are described e.g. in US 2006/0187752 or in U.S. Pat. No. 5,944,419. The disclosure of these patents is herewith incorporated by reference. Mixing tips which can also be used are commercially available from SulzerMixpac AG (Switzerland).

If the dental composition is provided in the form of a dental mill blank, it is typically fixed to a holding device including frames or mandrels.

The invention described in the present text is also directed to a kit of parts.

Such a kit typically comprises the dental composition described in the present text, a dental adhesive and/or a dental cement, optionally an applicator and optionally an instruction of use.

The instruction of use typically contains hints to the practitioner how and under what conditions the adhesive composition should be applied to the surface of hard dental tissue.

The dental composition can be used as or for producing a dental filling material, dental cement, dental crown or bridge material or a dental mill blank.

The dental composition is typically used in the mouth of a patient and is disposed adjacent to natural teeth. The phrase "disposed adjacent to" as used herein refers to the placing of a dental material in temporary or permanent (e.g., occlusal or proximal) contact with a natural tooth.

The term "composite" as used herein in the context of a dental material refers to a filled dental material. The term "restorative" as used herein refers to a dental composite that is polymerized after it is disposed adjacent to a tooth. The term "prosthesis" as used herein refers to a composite that is shaped and polymerized for its final use (e.g., as a crown, bridge, veneer, inlay, onlay or the like) before it is disposed adjacent to a tooth.

A typical application process for the composition described in the present text to be used as a restorative composite typically includes the following steps in the desired order:
providing the composition,
placing the composition in contact with hard dental tissue, especially the surface thereof,
curing the composition, e.g. by applying radiation (e.g. visible light) to the composition for a period of time sufficient to initiate the polymerisation process (e.g. about 5 to about 20 s).

Suitable tools for applying radiation include dental curing lights. Suitable dental curing lights are described e.g. in US 2005/0236586. The content of this document is herewith incorporated by reference. Suitable dental curing lights are also commercially available e.g. under the trade names Elipar™ S10 (3M ESPE).

The dental composition described in the present text can also be used for producing a dental crown, bridge, onlay or inlay outside the mouth of a patient.

The production can be done either by a so-called constructive approach (i.e. build-up approach) or by a so-called destructive approach (i.e. machining or milling approach).

The build-up approach can be performed by any means known to the skilled person including rapid-prototyping techniques.

Rapid-prototyping techniques include ink-jet printing, 3d-printing, robo-casting, laminated object manufacturing, stereolithography, photostereolithography, or combinations thereof.

A suitable example for a suitable process is described e.g. in US 2012/068388 (3M). The content of this reference is herewith incorporated by reference.

The machining approach can also be performed by any means known to the skilled person including milling the desired dental restoration out of a dental mill blank.

If desired, the dental mill blank can be attached to a holding device. Suitable holding devices include frames and stubs or mandrels. Sometimes it can be desirable, if the dental mill blank is put in a magazine, either for storing or for machining. The holding device typically facilitates the machining of the dental article, e.g. by using a machining or milling device.

Examples of holding devices are shown in US 2003/0132539, U.S. Pat. No. 6,769,912 and EP 0 455 854 B1. The content of these documents with regard to holding devices (e.g. frames and stubs or supporting body) is herewith incorporated by reference and regarded part of the text of the present invention.

Fixing of the dental mill blank to the holding device can be achieved e.g. by gluing. The fixing should be such that the dental milling blank can be processed in a milling machine.

Besides gluing other means for attaching the holding device include bonding, screwing, and combinations thereof.

Thus, a further embodiment of the present invention is directed to a process for producing a dental mill blank, the process comprising the steps of
- providing a dental composition as described in the present text, the dental composition being in its uncured state,
- hardening or curing the dental composition to obtain a hardened or cured dental composition,
- optionally fixing the hardened dental composition to a holding device, the dental composition being provided in the shape of a dental mill blank.

The dental mill blank can be produced by placing the curable dental composition into a mould followed by a curing step.

Another option for producing a dental mill blank is to apply a build-up or layer technique. In that case, the dental composition is typically provided in the form of a flat layer, the layer is cured and a further curable layer of the dental composition is applied on top of the previous layer followed by a further curing step. These steps are repeated until the object has the desired dimensions.

Yet, a further embodiment of the present invention is directed to a process for producing a dental restoration, the process comprising the steps of
- providing a dental mill blank as described in the present text, the dental mill blank comprising the dental composition described in the present text, the dental composition being in its cured state,
- machining the dental mill blank to obtain a dental restoration, the dental restoration having typically the shape of a dental crown, bridge, inlay or veneer.

According to a particular embodiment, the dental composition described in the present text is characterized as follows:

- Polymerizable monomer(s) (1): being represented by a formula as described in the text above with respect to the polymerizable monomer (1) in an amount from about 1 to about 75 wt.-%,
- Radiation curing initiator(s),
- Filler(s) being selected from silica or silica/zirconia filler(s) in an amount from about 20 to about 95 wt.-%.

All components used in the dental composition of the invention should be sufficiently biocompatible, that is, the composition should not produce a toxic, injurious, or immunological response in living tissue.

According to one embodiment, the dental composition described in the present text does not contain or is essentially free of solvent(s) selected from water, alcohols (e.g. ethanol) or combinations thereof in an amount of more than about 5, 10 or 20 wt.-%, wt.-% with respect to the weight of the whole composition.

The dental composition does also typically not contain Bis-GMA or bisphenol moiety(s) containing components in an amount of more than about 1 or 5 wt.-%, with respect to the weight of the whole composition.

The complete disclosures of the patents, patent documents, and publications cited herein are incorporated by reference in their entirety as if each were individually incorporated. Various modifications and alterations to this invention will become apparent to those skilled in the art without departing from the scope and spirit of this invention. The above specification, examples and data provide a description of the manufacture and use of the compositions and methods of the invention. The invention is not limited to the embodiments disclosed herein. One skilled in the art will appreciate that many alternative embodiments of the invention can be made without departing from the spirit and scope of thereof.

The following examples are given to illustrate, but not limit, the scope of this invention. Unless otherwise indicated, all parts and percentages are by weight.

EXAMPLES

Unless otherwise indicated, all parts and percentages are on a weight basis, all water is deionized water, and all molecular weights are weight average molecular weight. Moreover, unless otherwise indicated all Experiments were conducted at ambient conditions (23° C.; 1013 mbar). Moreover, nearly all process steps are conducted under an atmosphere of dry air:

Compressive Strength (CS)

The measurement of the compressive strength was carried out according to ISO 4049 using specimens having the dimension of 3 mm×3 mm×5 mm. The compressive strength 1 is given in MPa.

Shrinkage Stress (Stress)

Shrinkage stress was measured according to the procedure of Sakaguchi et al. (Dent. Mater. 1997, 13, 233-239). Irradiation of 45 mg samples was done for 40 s using a 3M XL3000 (650 mW) irradiation device. The stress value in µstrain was recorded 10 min after start of the irradiation.

Compositions

Abbreviations

The name and/or structure of the components used are given in Table 1.

TABLE 1
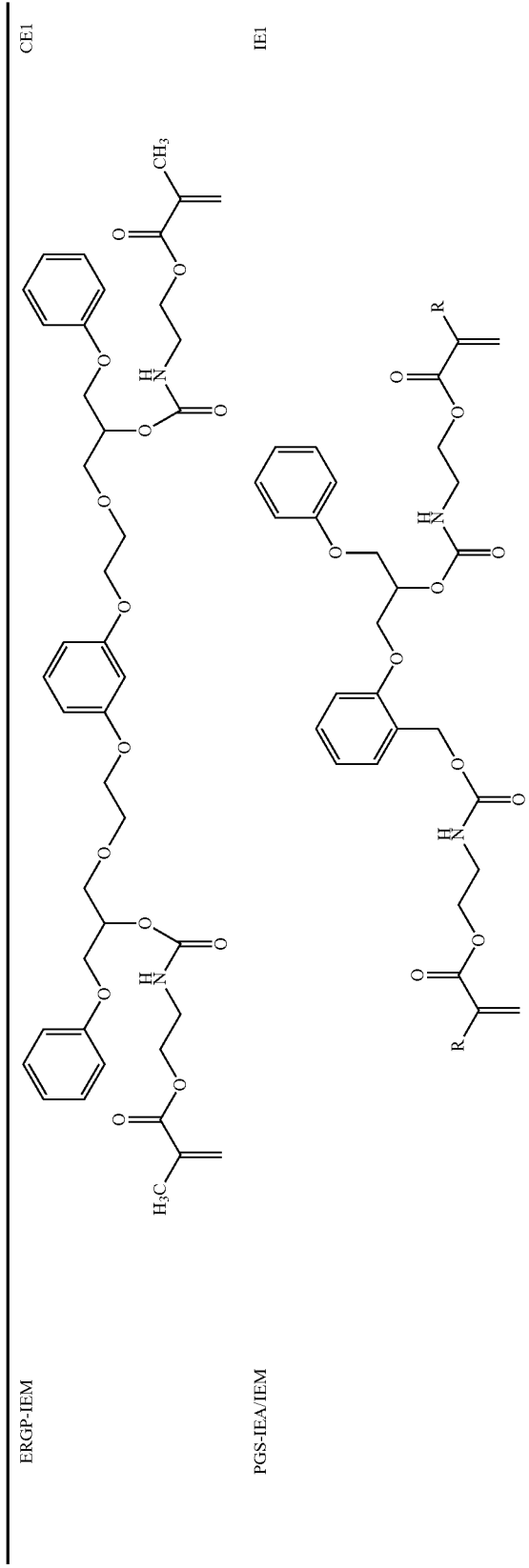
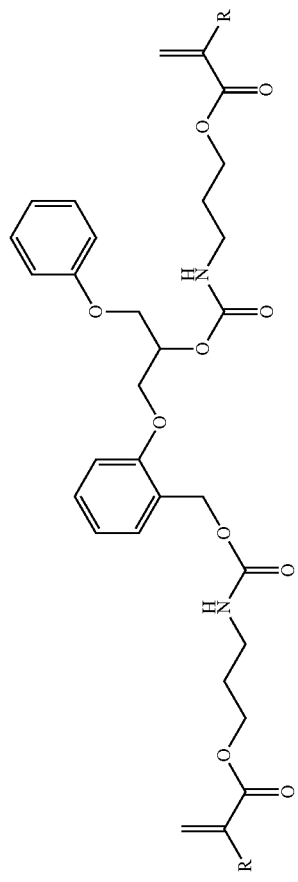

TABLE 1-continued
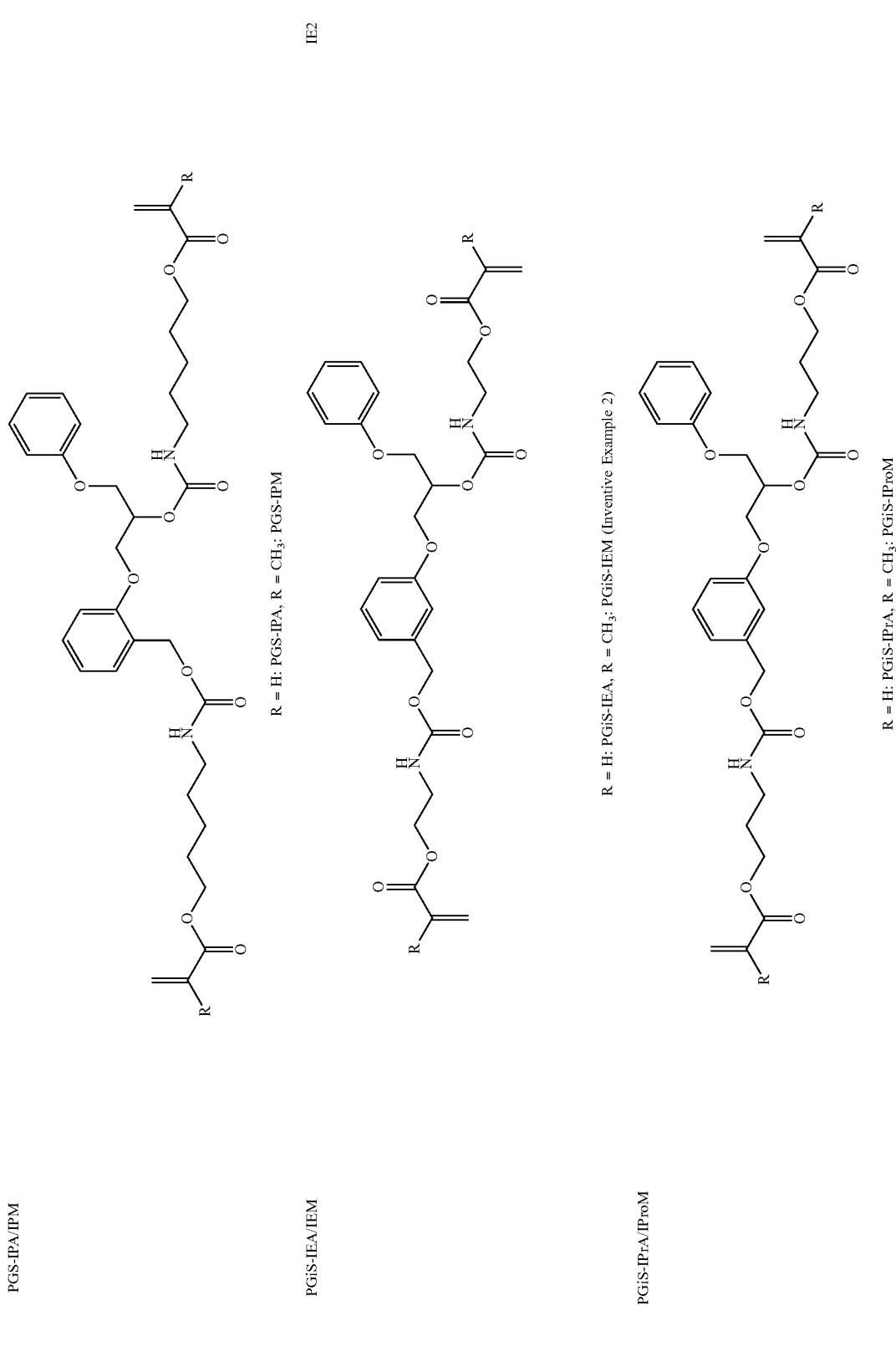

TABLE 1-continued

PGiS-IPA/IPM

R = H: PGiS-IPA, R = CH₃; PGiS-IPM

PGT-IEA/IEM

R = H: PGT-IEA (Inventive Example 3), R = CH₃; PGT-IEM (Inventive Example 4)

PGT-IPrA/IProM

R = H: PGT-IPrA (Inventive Example 5), R = CH₃; PGT-IProM (Inventive Example 6)

TABLE 1-continued
| PGT-IPA/IPM | 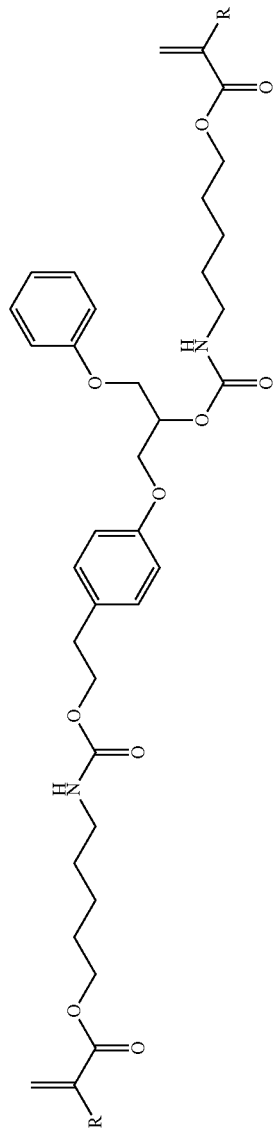 R = H: PGT-IPA R = CH₃: PGT-IPM (Inventive Example 9) | IE9 |
| --- | --- | --- |
| PGSA/PGSM-IEA/IEM | 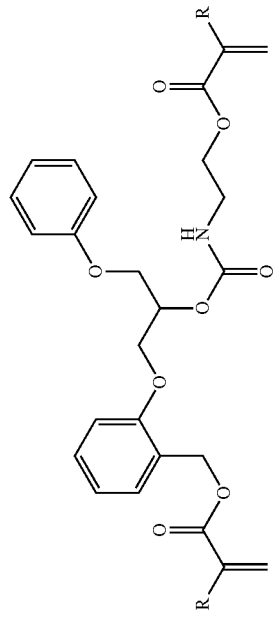 R = H: PGSA-IEA, R = CH₃: PGSM-IEM | |
| PGiSA/PGiSM-IEA/IEM | 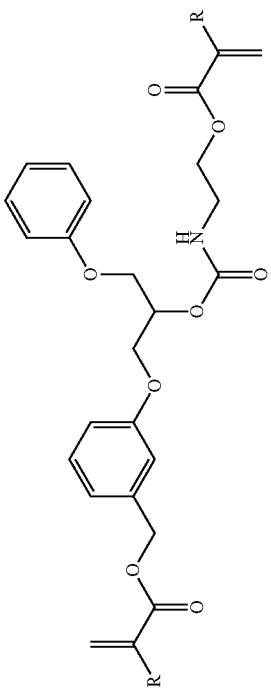 R = H: PGiSA-IEA, R = CH₃: PGiSM-IEM | |

TABLE 1-continued
| | IE7 |
|---|---|
| PGTA/PGTM-IEA/IEM | 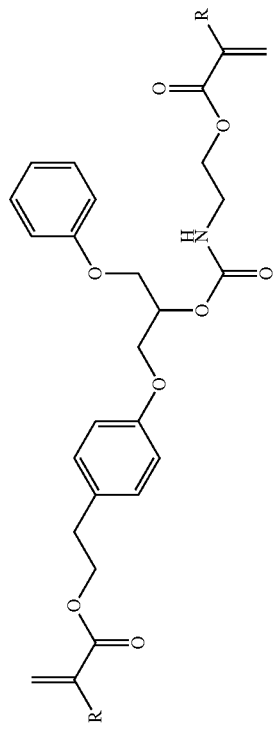<br>R = H: PGTA-IEA, R = CH₃: PGTM-IEM (Inventive Example 7) |
| PGSA/PGSM-IPrA/IProM | 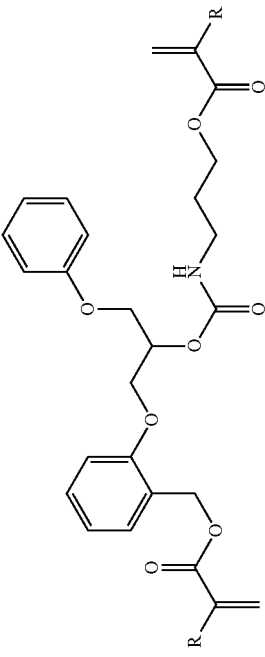<br>R = H: PGSA-IPrA, R = CH₃: PGSM-IProM |
| PGiSA/PGiSM-IPrA/IProM | 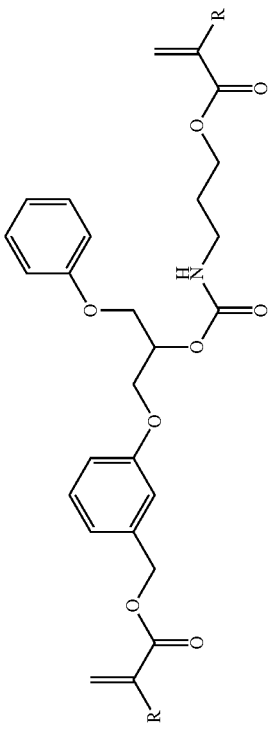<br>R = H: PGiSA-IPrA, R = CH₃: PGiSM-IProM |

TABLE 1-continued
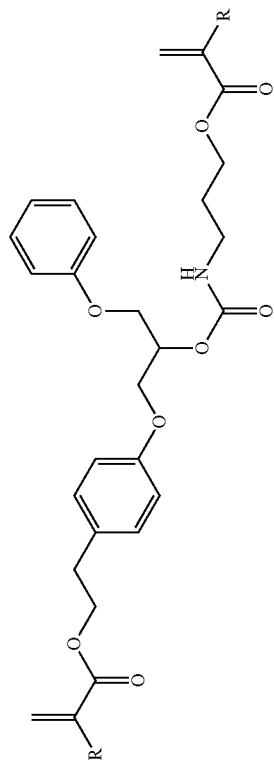
R = H: PGTA-IPrA, R = CH₃: PGTM-IProM (Inventive Example 10)
PGTA/PGTM-IPrA/IProM
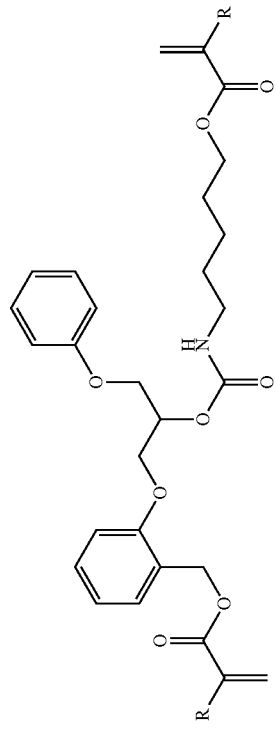
R = H: PGSA-IPA, R = CH₃: PGSM-IPM
PGSA/PGSM-IPA/IPM
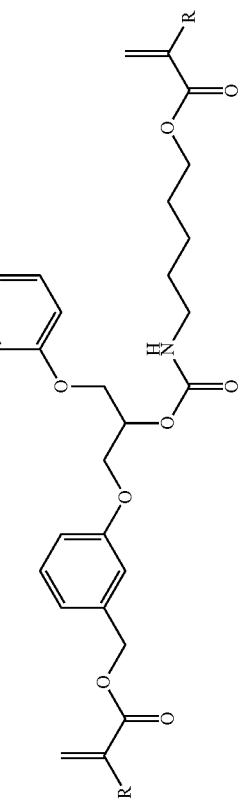
R = H: PGiSA-IPA, R = CH₃: PGiSM-IPM
PGiSA/PGiSM-IPA/IPM TABLE 1-continued
| PGTA/PGTM-IPA/IPM | 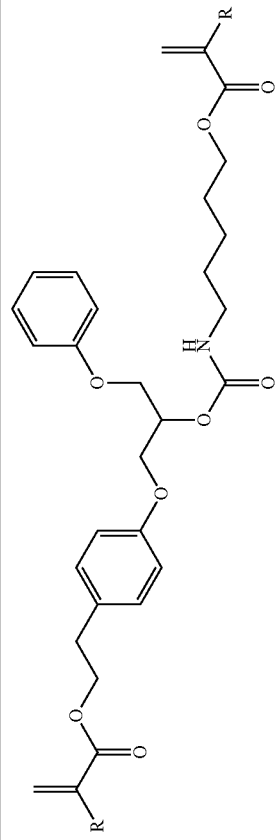 IE11<br>R = H: PGTA-IPA, R = CH₃; PGTM-IPM (Inventive Example 11) |
| --- | --- |
| GS-IEA/IEM | 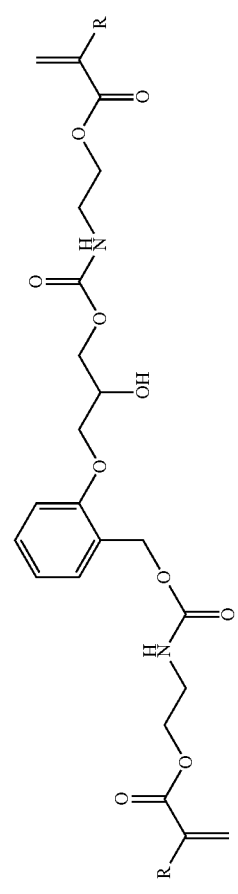<br>R = H: GS-IEA, R = CH₃; GS-IEM |
| GS-IPrA/IProM | 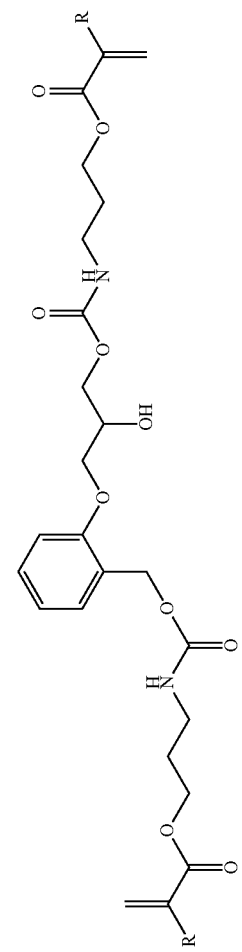<br>R = H: GS-IPrA, R = CH₃; GS-IProM |

TABLE 1-continued
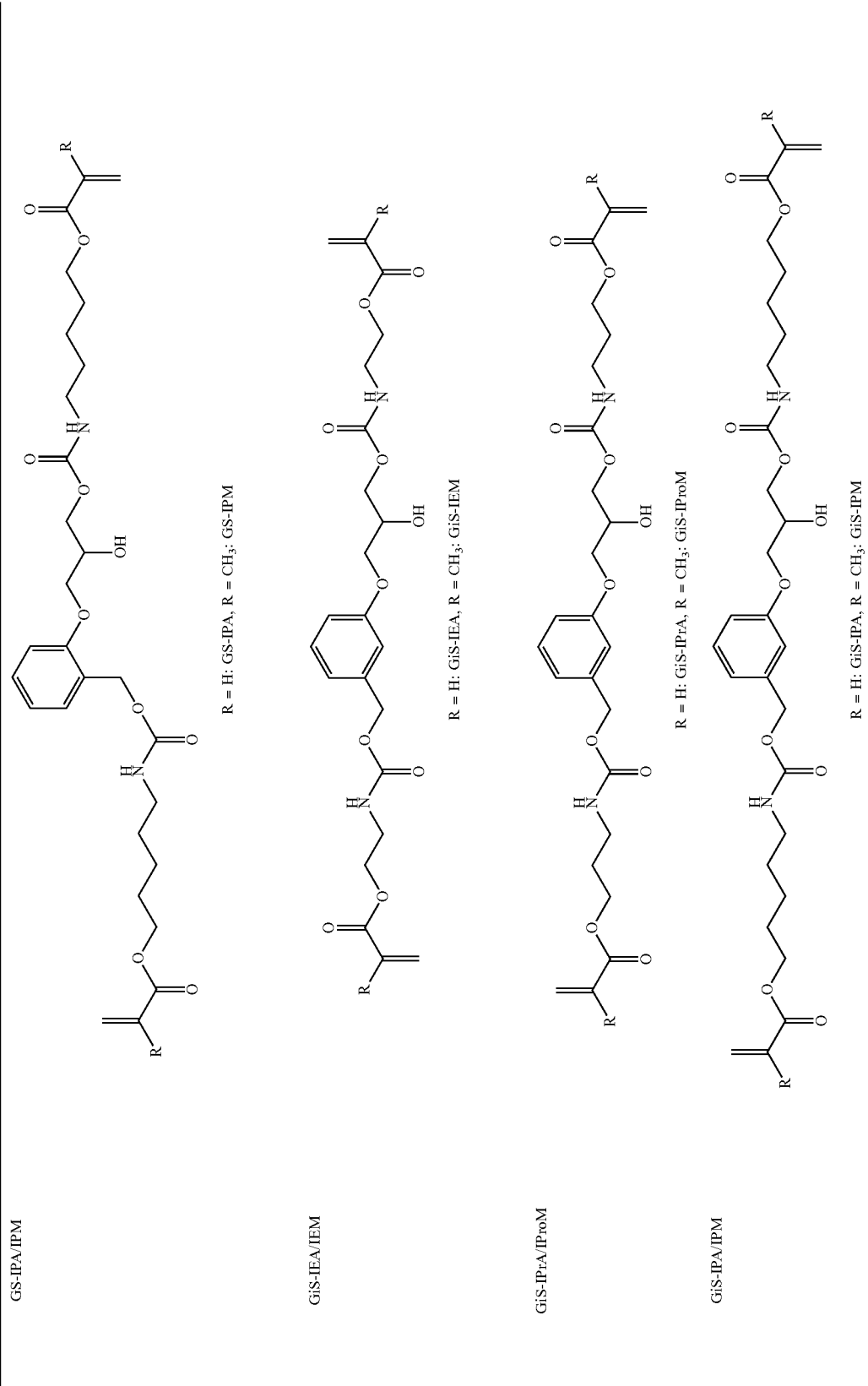

TABLE 1-continued
| | |
|---|---|
| GT-IEA/IEM | 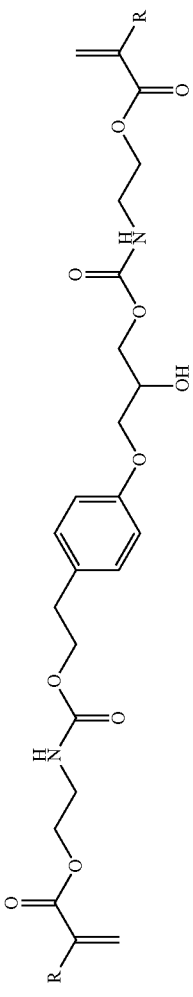 R = H: GT-IEA, R = CH₃: GT-IEM (Inventive Example 8) |
| GT-IPrA/IProM | 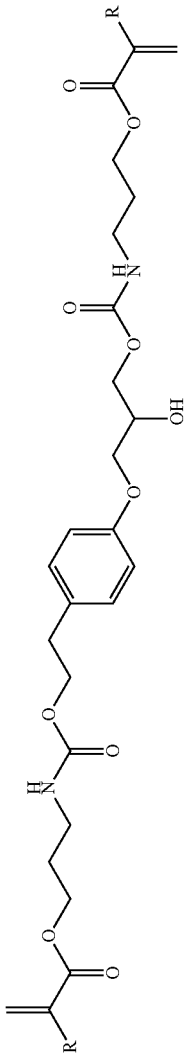 R = H: GT-IPrA, R = CH₃: GT-IProM |
| GT-IPA/IPM | 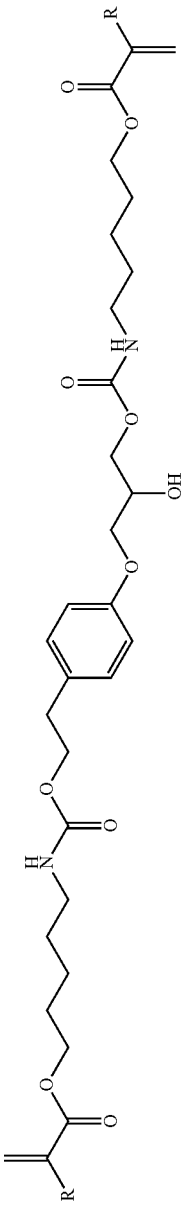 R = H: GT-IPA, R = CH₃: GT-IPM |
| GSA/GSM-IEA/IEM | 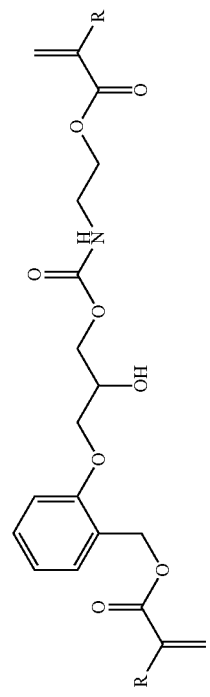 R = H: GSA-IEA, R = CH₃: GSM-IEM |

TABLE 1-continued
| | |
|---|---|
| GSA-GSM-IPrA/IProM | 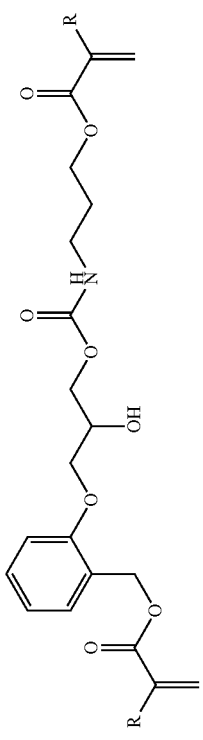 R = H: GSA-IPrA, R = CH₃; GSM-IProM |
| GSA/GSM-IPA/IPM | 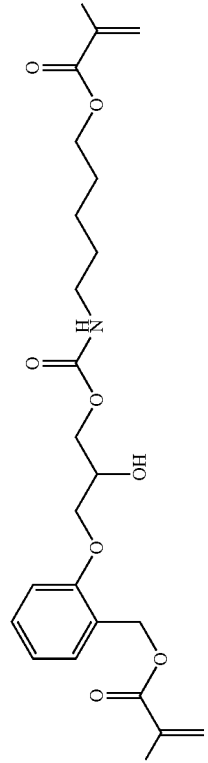 R = H: GSA-IPA, R = CH₃; GSM-IPM |
| GiSA/GiSM-IEA/IEM | 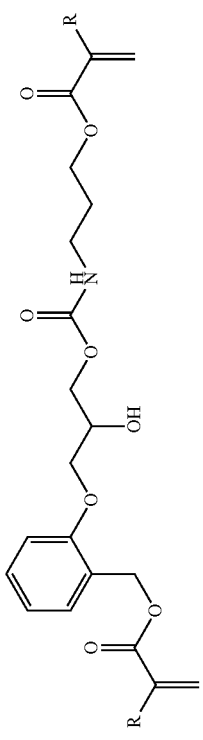 R = H: GiSA-IEA, R = CH₃; GiSM-IEM |
| GiSA/GiSM-IPrA/IProM | 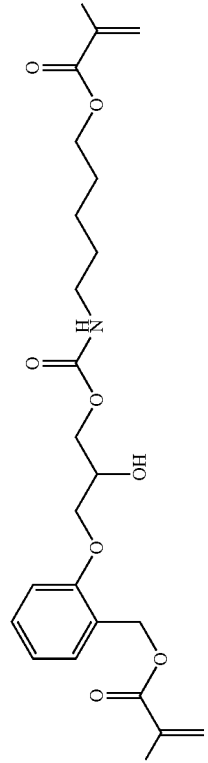 R = H: GiSA-IPrA, R = CH₃; GiSM-IProM |
| GiSA/GiSM-IPA/IPM | 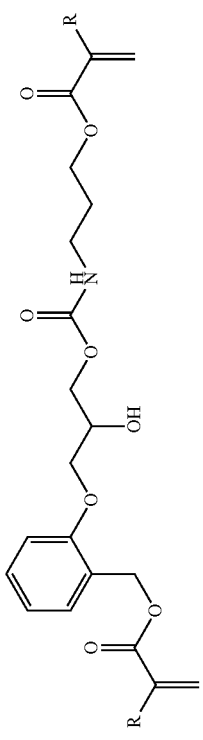 R = H: GiSA-IPA, R = CH₃; GiSM-IPM |

TABLE 1-continued
| GTA/GTM-IEA/IEM | 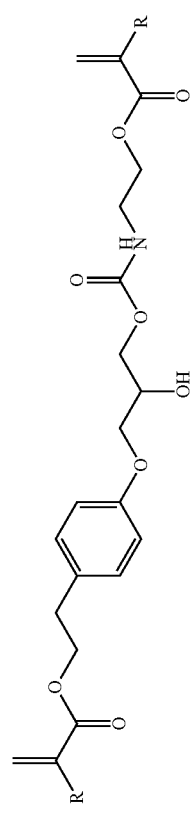 R = H: GTA-IEA, R = CH₃: GTM-IEM |
| --- | --- |
| GTA/GTM-IPrA/IProM | 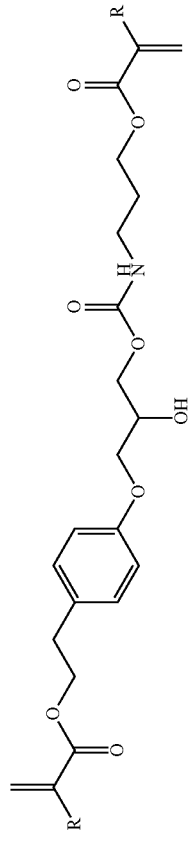 R = H: GTA-IPrA, R = CH₃: GTM-IProM |
| GTA/GTM-IPA/IPM | 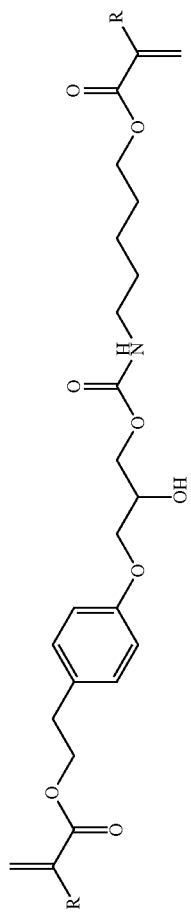 R = H: GTA-IPA, R = CH₃: GTM-IPM |
| ET-IEA/IEM | 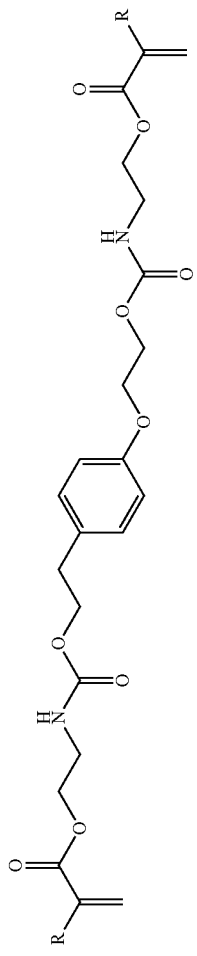 R = H: ET-IEA, R = CH₃: ET-IEM |

TABLE 1-continued

| | |
|---|---|
| ET-IPrA/IProM | R = H: ET-IPrA, R = CH₃: ET-IProM |
| ET-IPA/IPM | R = H: ET-IPA, R = CH₃: ET-IPM |
| E2T-IEA/IEM | R = H: E2T-IEA, R = CH₃: E2T-IEM |
| E2T-IPrA/IProM | R = H: E2T-IPrA, R = CH₃: E2T-IProM |

TABLE 1-continued

R = H: E2T-IPA, R = CH₃; E2T-IPM

E2T-IPA/IPM

OoHBGP/OoHBGP-IEA/IEM

E2oHBGP/E2oHBGP-IEA/IEM

OmHBGP/OmHBGP-IEA/IEM

TABLE 1-continued
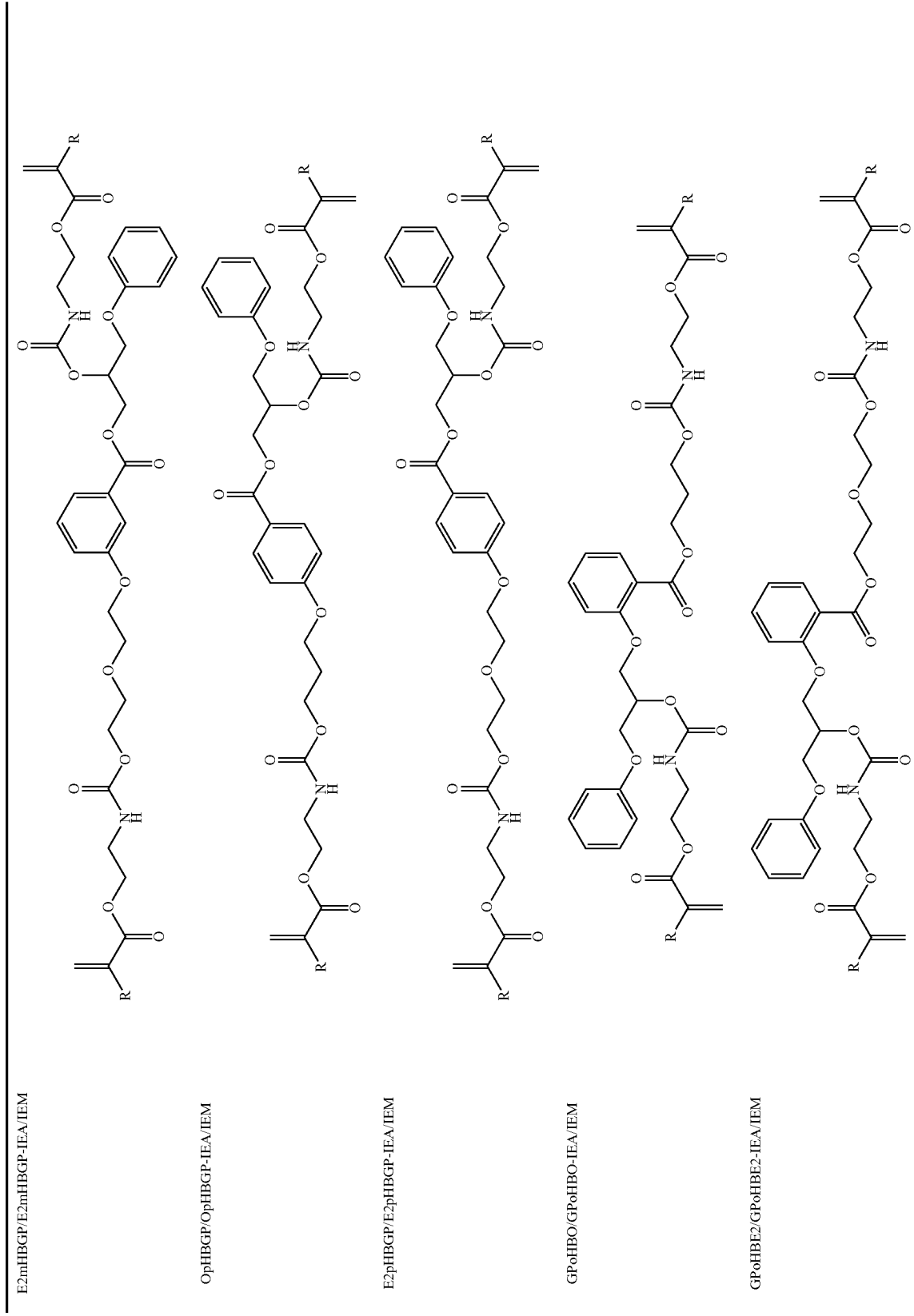

TABLE 1-continued
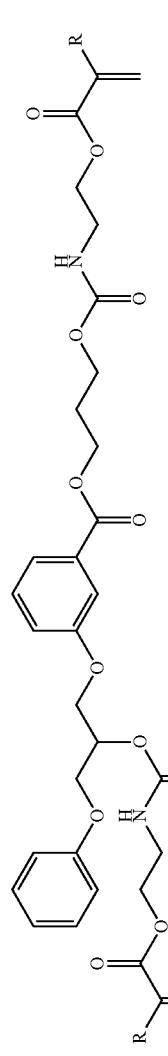
GPmHBO/GPmHBO-IEA/IEM
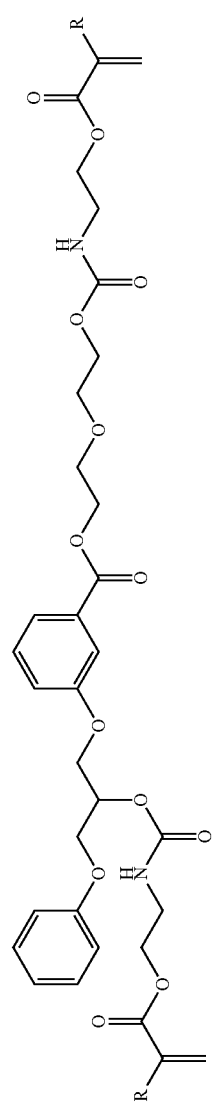
GPmHBE2/GPmHBE2-IEA/IEM
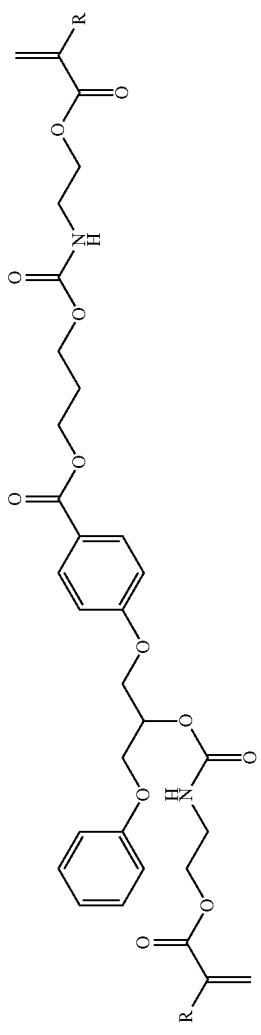
GPpHBO/GPpHBO-IEA/IEM
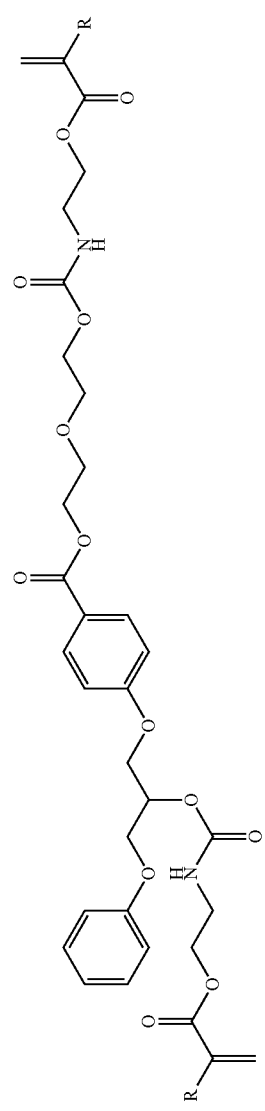
GPpHBE2/GPpHBE2-IEA/IEM TABLE 1-continued

| | |
|---|---|
| ETA/ETM-IEA/IEM | R = H: ETA-IEA, R = CH₃: ETM-IEM |
| ETA/ETM-IPrA/IProM | R = H: ETA-IPrA, R = CH₃: ETM-IProM |
| ETA/ETM-IPA/IPM | R = H: ETA-IPA, R = CH₃: ETM-IPM |
| E2TA/E2TM-IEA/IEM | R = H: E2TA-IEA, R = CH₃: E2TM-IEM |

TABLE 1-continued
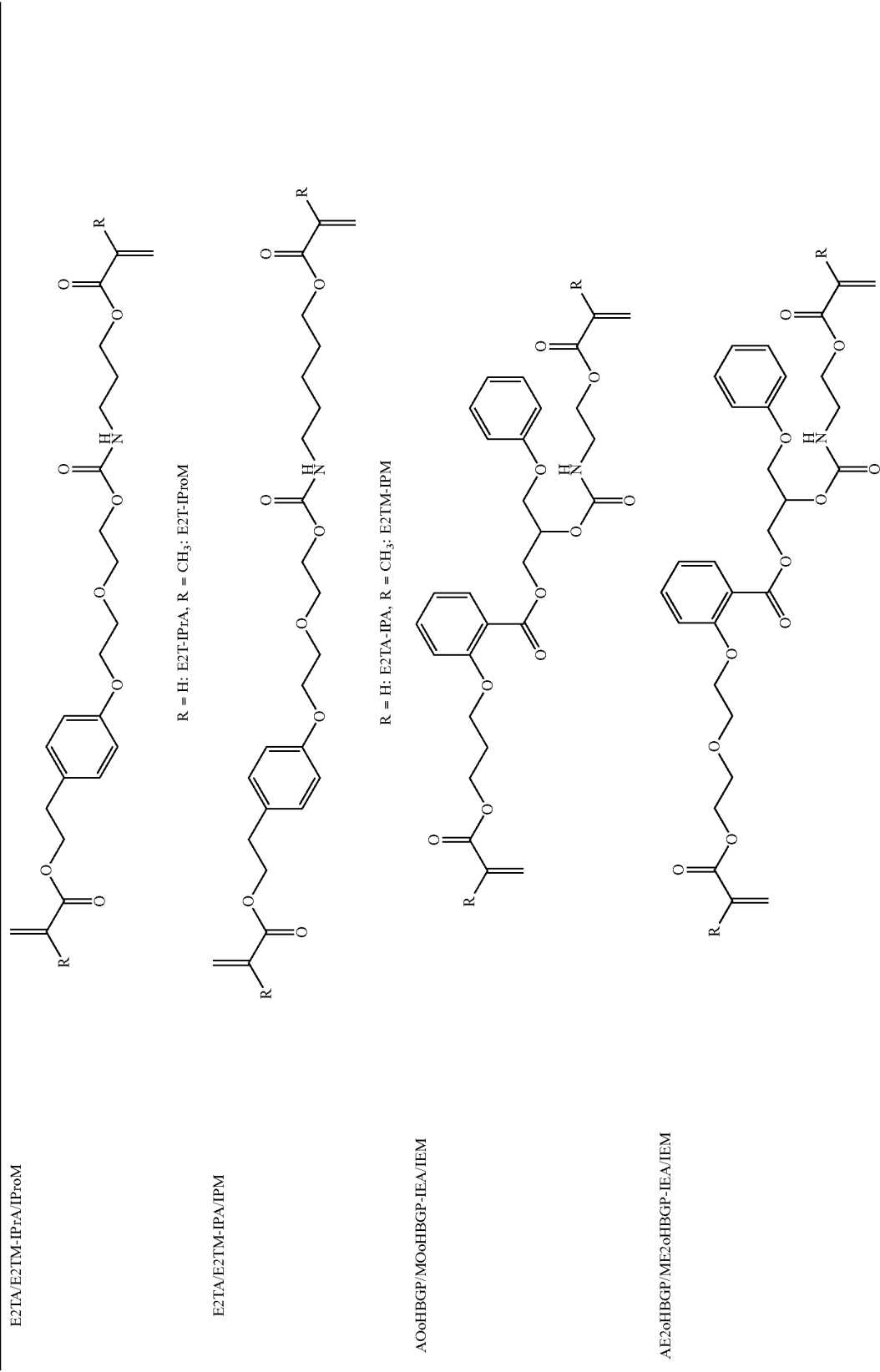

TABLE 1-continued
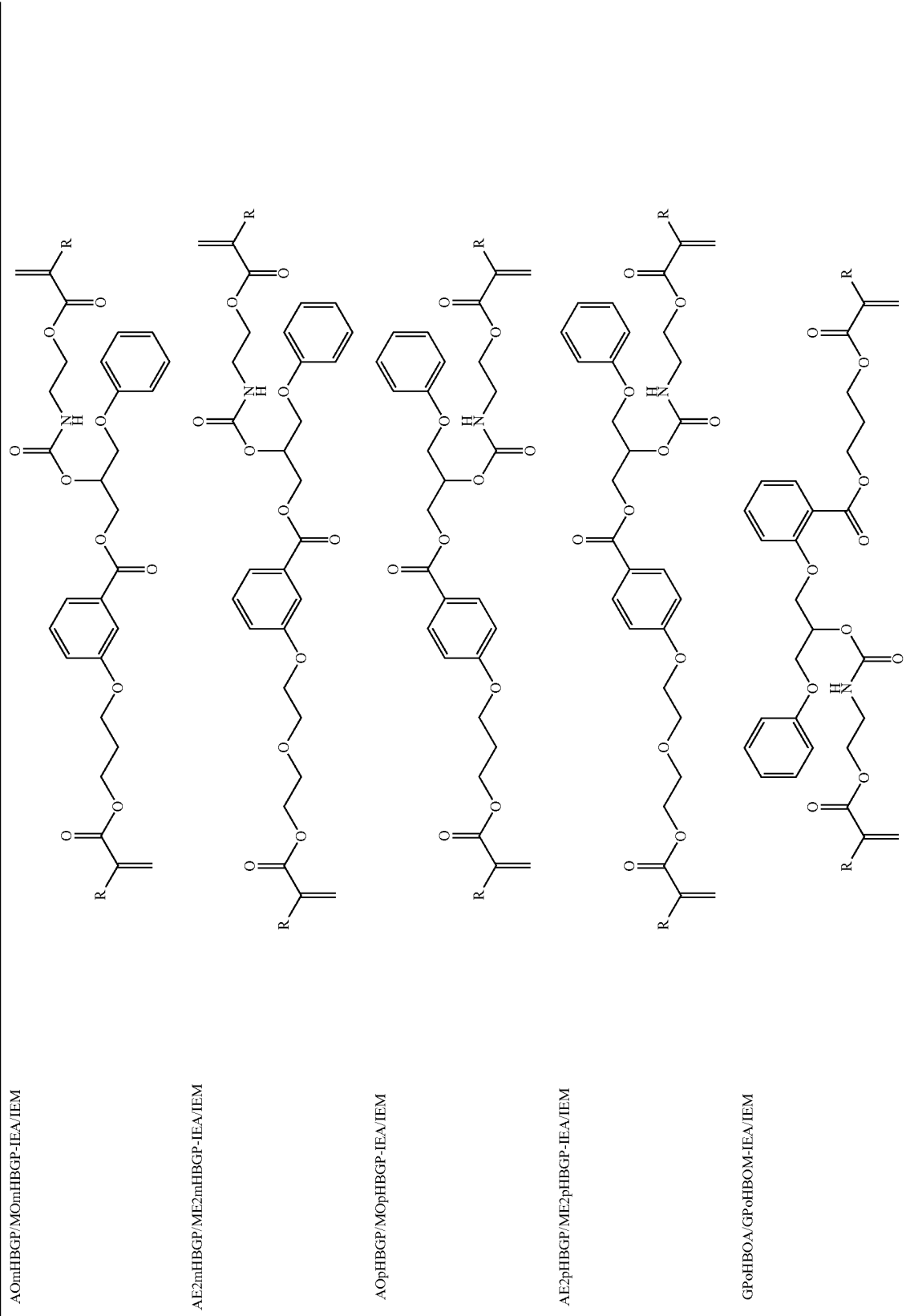

TABLE 1-continued
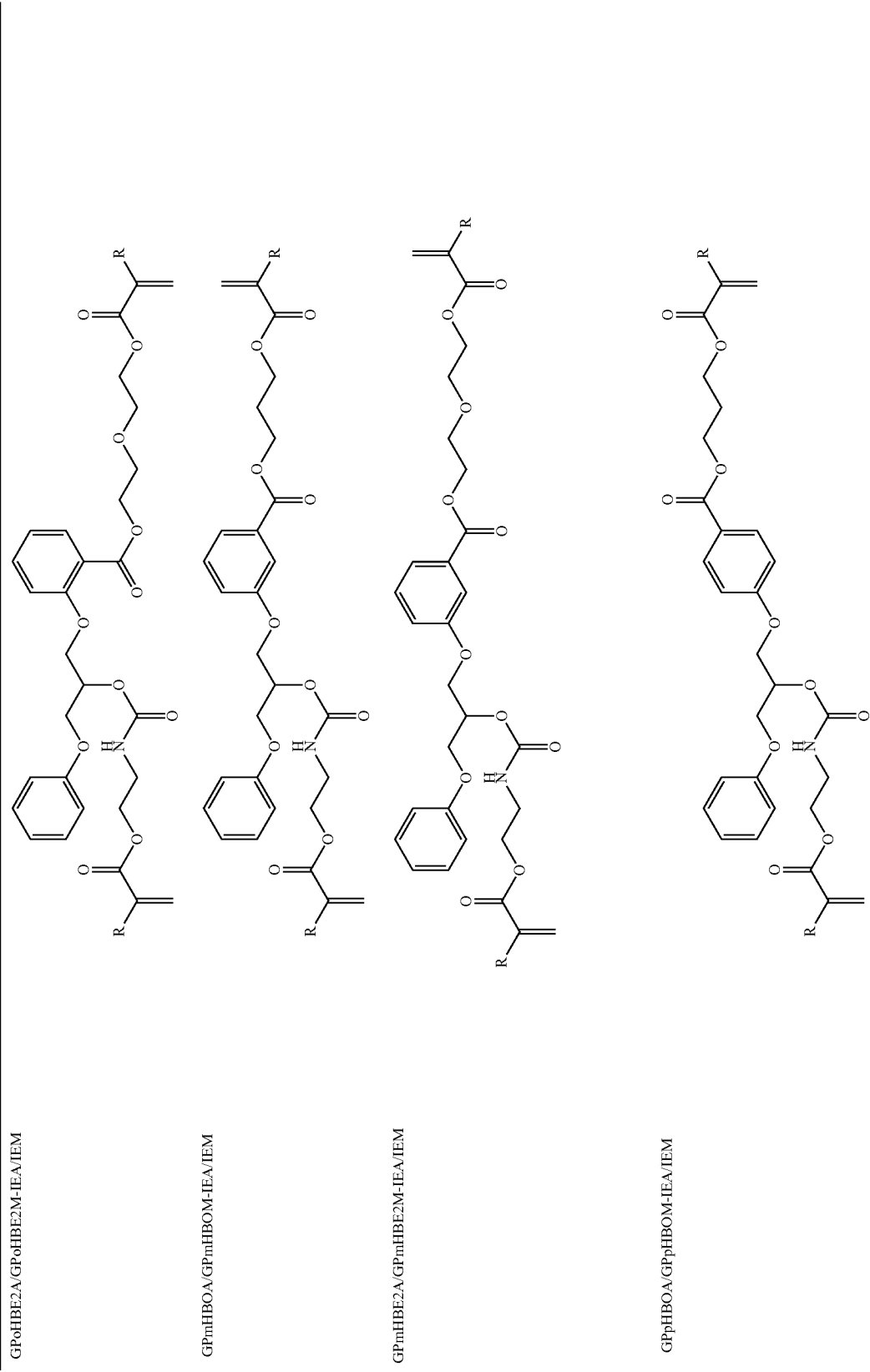
GPoHBE2A/GPoHBE2M-IEA/IEM
GPmHBOA/GPmHBE2M-IEA/IEM
GPmHBE2A/GPmHBOM-IEA/IEM
GPpHBOA/GPpHBOM-IEA/IEM TABLE 1-continued
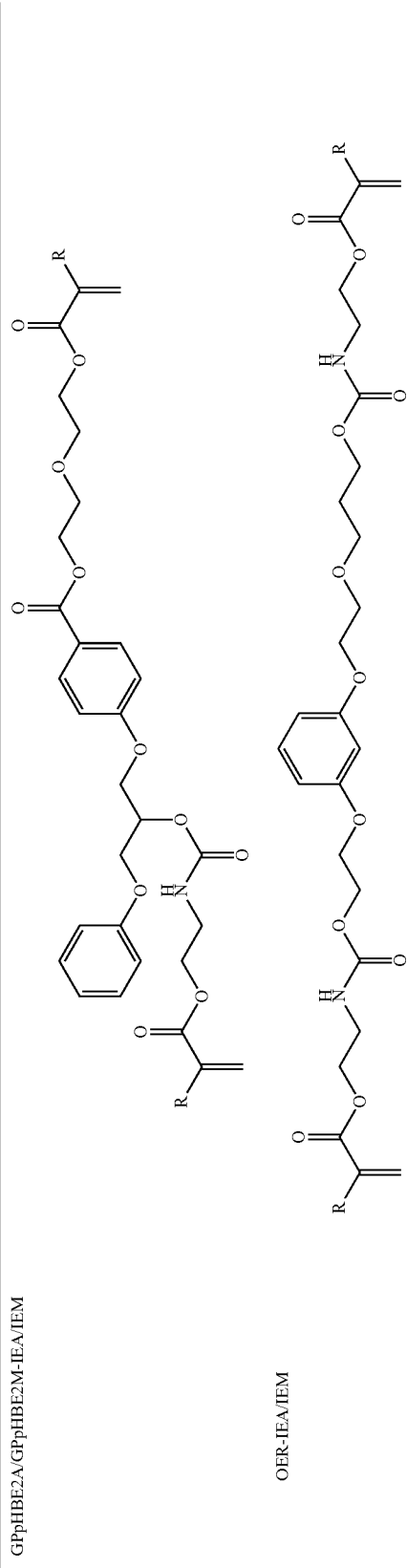
GPpHBE2A/GPpHBE2M-IEA/IEM
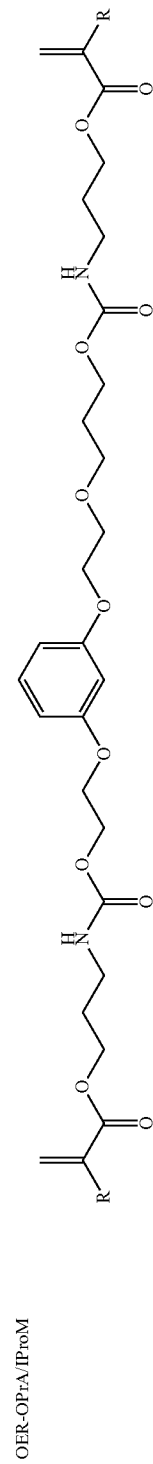
OER-IEA/IEM
R = H: OER-IEA, R = CH₃; OER-IEM
OER-OPrA/IProM
R = H: OER-IPrA, R = CH₃; OER-IProM
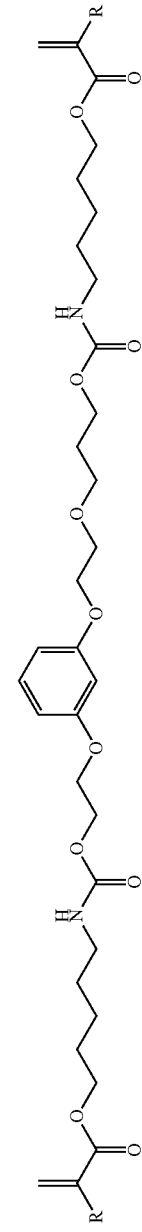
OER-IPA/IPM
R = H: OER-IPA, R = CH₃; OER-IPM TABLE 1-continued
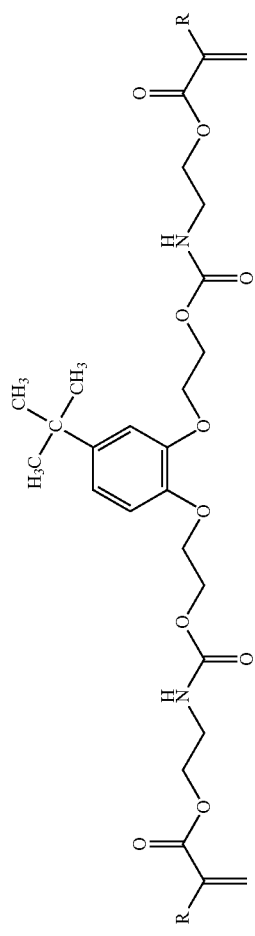
EBC-IEA/IEM
R = H: EBC-IEA, R = CH₃: EBC-IEM
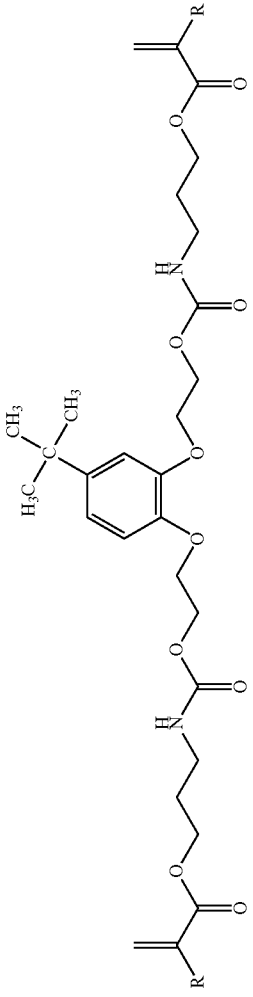
EBC-IPrA/IProM
R = H: EBC-IPrA, R = CH₃: EBC-IProM
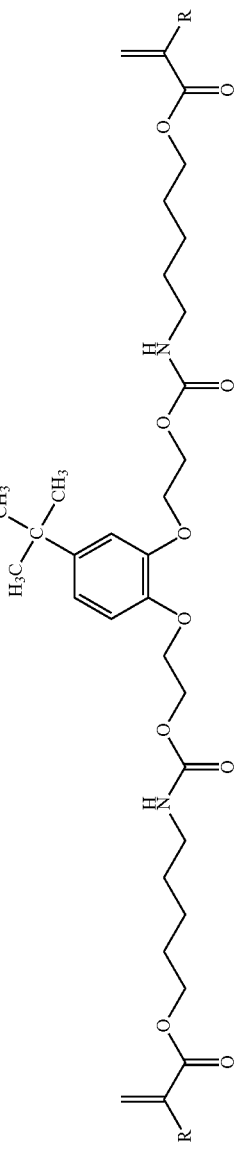
EBC-IPA/IPM
R = H: EBC-IPA, R = CH₃: EBC-IPM TABLE 1-continued
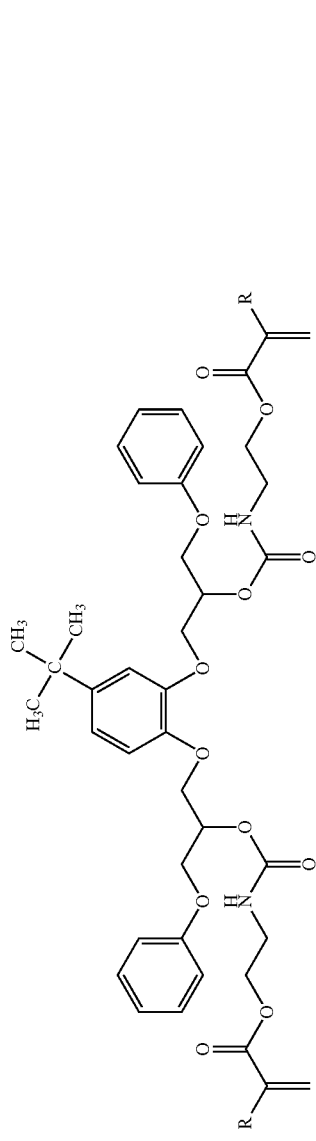
BCGP-IEA/IEM
R = H: BCGP-IEA, R = CH₃; BCGP-IEM
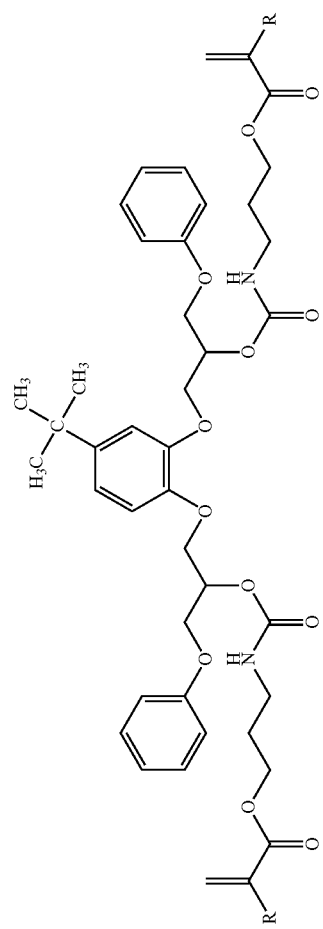
BCGP-IPrA/IProM
R = H: BCGP-IPrA, R = CH₃; BCGP-IProM TABLE 1-continued

| BCGP-IPA/IPM | 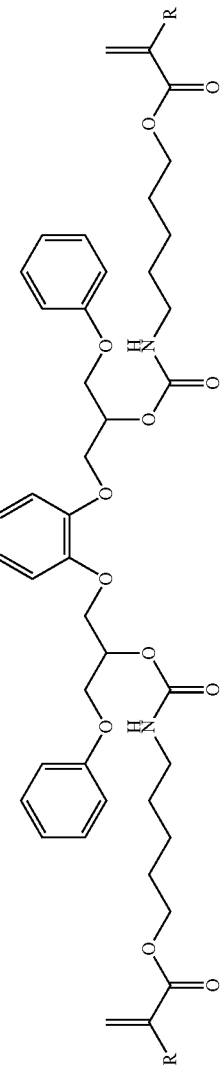 | IE12 |
|---|---|---|
| | R = H: BCGP-IPA, R = CH₃: BCGP-IPM (Inventive Example 12) | |
| Resorcinol | 1,3-dihydroxybenzene, CAS 108-46-3, EC 203-585-2 | R |
| Catechol | 1,2-dihydroxybenzene, CAS 120-80-9, EC 204-427-5 | C |
| Tert-butylcatechol | 4-tert-butylcatechol, 4-tert-butyl-1,2-dihydroxybenzene, CAS 98-29-3, EC 202-653-9 | BC |
| Tyrosol | 4-(2-hydroxyethyl)phenol, 2-(4-hydroxyphenyl)ethanol, CAS 501-94-0, EC 207-930-8 | T |
| Salicyl alcohol | 2-hydroxybenzyl alcohol, 2-hydroxymethylphenol, Saligenin, CAS 90-01-7, EC 201-960-5 | S |
| iso-Salicyl alcohol | 3-hydroxybenzyl alcohol, 3-hydroxymethylphenol, CAS 620-24-6, EC 210-633-6 | iS |
| ortho-Hydroxybenzoic Acid | Salicylic acid, 2-hydroxybenzoic acid, CAS 69-72-7, EC 200-712-3 | oHB |
| meta-Hydroxybenzoic Acid | Iso-Salicylic acid, 3-hydroxybenzoic acid, CAS 99-06-9, EC 202-726-5 | mHB |
| para-Hydroxybenzoic Acid | 4-hydroxybenzoic acid, CAS 99-96-7, EC 202-804-9 | pHB |
| Tyrosol Mono (Meth)acrylate | 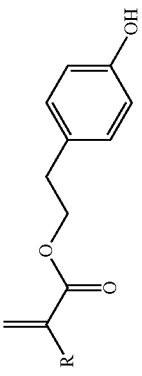<br>R = H: TA, R = CH₃; TM | TM |
| Salicyl Alcohol Mono (Meth)acrylate | 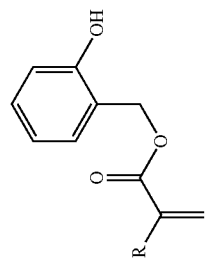<br>R = H: SA, R = CH₃; SM | SM |

TABLE 1-continued
| iso-Salicyl Alcohol Mono (Meth)acrylate | 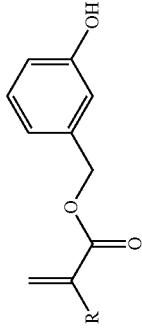 R = H: iSA, R = CH₃: iSM | iSM |
|---|---|---|
| AOoHB/MOoHB | 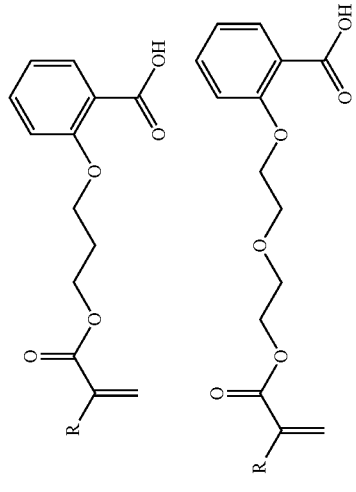 | |
| AE2oHB/ME2oHB | 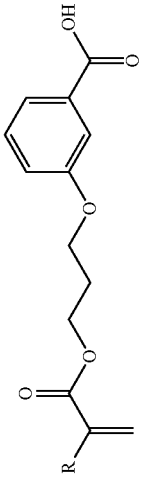 | |
| AOmHB/MOmHB | 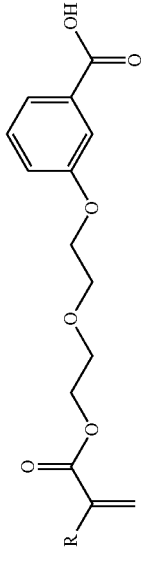 | |
| AE2mHB/ME2mHB | 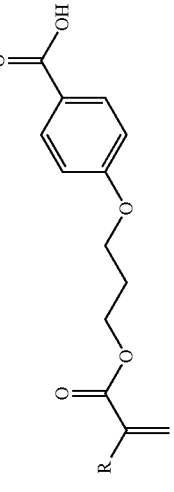 | |
| AOpHB/MOpHB | 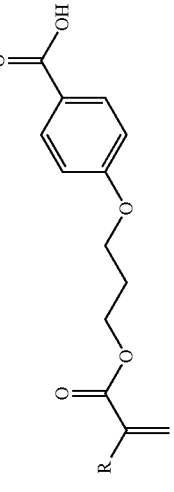 | |

TABLE 1-continued
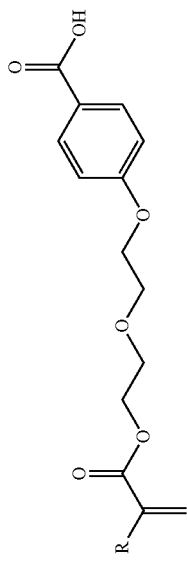
AE2pHB/ME2pHB
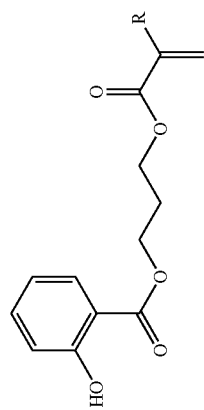
oHBOA/oHBOM
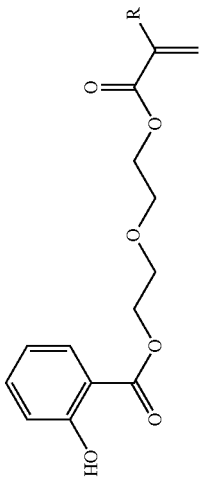
oHBE2A/oHBE2M
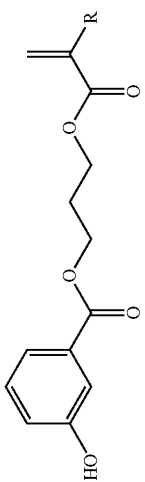
mHBOA/mHBOM
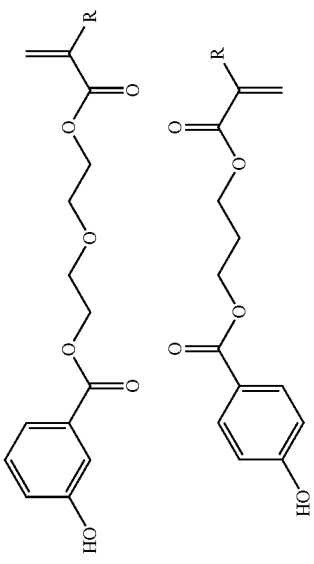
mHBE2A/mHBE2M    pHBOA/pHBOM TABLE 1-continued
| | | |
|---|---|---|
| pHBE2A/pHBE2M | 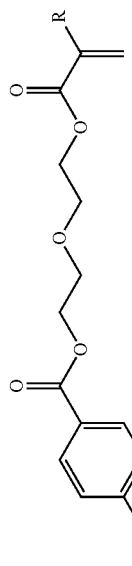 | |
| PGTA/PGTM | 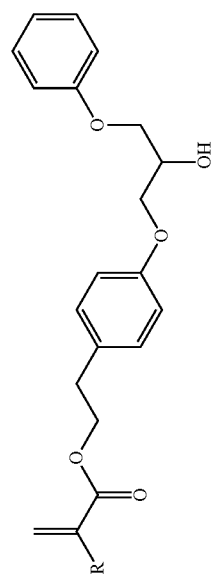 R = H: PGTA, R = CH₃; PGTM | |
| PGSA/PGSM | 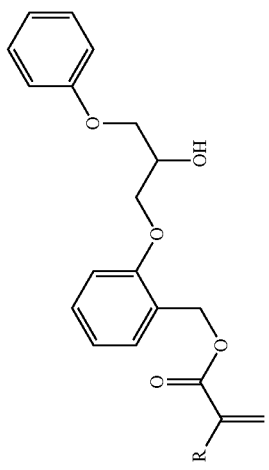 R = H: PGSA, R = CH₃; PGSM | |
| PGiSA/PGiSM |  R = H: PGiSA, R = CH₃; PGiSM | PG |
| Resorcinol monoacetate<br>Resorcinol diacetate<br>2-chloroethanol<br>3-chloro-1-propanol | 3-hydroxyphenyl acetate, CAS 102-29-4, EC 203-022-0<br>1,3-diacetoxybenzene, CAS 108-58-7, EC 203-596-2<br>Ethylene chlorohydrin, CAS 107-07-3, EC 203-459-7<br>1-chloro-3-hydroxypropane, CAS 627-30-5, EC 210-992-9 | RAc<br>RAc2 |

TABLE 1-continued

| Name | Description | Abbreviation |
|---|---|---|
| 2-(2-chloroethoxy)-ethanol | 3-oxa-5-chloro-1-pentanol, CAS 628-89-7, EC 211-059-9 | GP |
| 5-chloro-1-pentanol | Pentamethylene chlorohydrin, CAS 5259-98-3, EC 226-067-8 | AA |
| 6-chloro-1-hexanol | Hexamethylene chlorohydrin, CAS 2009-83-8, EC 217-925-2 | MA |
| Ethylene carbonate | 1,3-Dioxolan-2-one, CAS 96-49-1, EC 202-510-0 | MSA |
| Glycidyl phenyl ether | 2-(phenoxymethyl)oxirane, 2,3-epoxypropyl phenyl ether, phenyl glycidyl ether, CAS 122-60-1, EC 204-557-2 | THF |
| Acrylic acid | Propenoic acid, CAS 79-10-7, EC 201-177-9 | IPA |
| Methacrylic acid | 2-Methacrylic acid, 2-Methylpropenoic acid, CAS 79-41-4, EC 201-204-4 | HOtBu |
| Methanesulfonic acid | CAS 75-75-2, EC 200-898-6 | KOtBu |
| Tetrahydrofuran | CAS 109-99-9, EC 203-726-8 | NaOH |
| iso-Propanol | 2-propanol, CAS 67-63-0, EC 200-661-7 | KOH |
| tert-Butanol | 2-methyl-2-propanol, CAS 75-65-0, EC 200-889-7 | MTBE |
| Potassium tert-butoxide | Potassium tert-butylate, CAS 865-47-4, EC 212-740-3 | EA |
| Sodium hydroxide | CAS 1310-73-2, EC 215-185-5 | MEK |
| Potassium hydroxide | CAS 1310-58-3, EC 215-181-3 | BHT |
| Methyl tert-butyl ether | tert-Butyl methyl ether, CAS 1634-04-4, EC 216-653-1 | HQ |
| Ethyl acetate | Acetic acid ethyl ester, CAS 141-78-6, EC 205-500-4 | HQME |
| Methyl ethyl ketone | Ethyl methyl ketone, 2-butanone, CAS 78-93-3, EC 201-159-0 | |
| 2,6-di-tert-Butyl-4-methylphenol | 2,6-Di-tert-butyl-p-cresol, Butylated hydroxytoluene, Butylhydroxytoluene, DBPC, CAS 128-37-0, EC 204-881-4 | |
| hydroquinone | 1,4-dihydroxybenzene, 1,4-benzenediol, CAS 123-31-9, EC 204-617-8 | |
| Hydroquinone monomethyl ether | 4-methoxyphenol, 4-Hydroxyanisole, 4-MP, HQMME, MEHQ, MQ-F, CAS 150-76-5, EC 205-769-8 | |
| Methylene blue | 3,7-bis(Dimethylaminophenazathionium chloride, Basic Blue 9, Tetramethylthionine chloride, CAS 7220-79-3, EC 200-515-2 | |
| Sodium carbonate | CAS 497-19-8, EC 207-838-8 | Na2CO3 |
| Potassium carbonate | CAS 584-08-7, EC 209-529-3 | K2CO3 |
| Filler 1 | Non agglomerated silanized silica nano filler, (50 nm); produced according to U.S. Pat. No. 6,899,948 B2 | F1 |
| Filler 2 | Aggregated Zr/Si nanoclusters; produced as described in U.S. Pat. No. 6,730,156, column 25, preparatory example A; surface treated according to process as described in preparatory example B. | F2 |
| CPQ | Camphorquinone (CAS no. 10373-78-1) | Ini1 |
| DPI-PF6 | Diphenyliodonium hexafluorophosphate (CAS no. 58109-40-3) | Ini2 |
| EDMAB | Ethyl 4-dimethylaminobenzoate (CAS no. 10287-53-3) | Ini3 |
| Triphenylphosphine | Triphenylphosphine, CAS no. 603-35-0, EC 210-036-0 | PPh₃ |
| Triethylamine | CAS no. 121-44-8, EC 204-469-4 | TEA |
| Glycidol | Oxirane-2-methanol, 2,3-Epoxy-1-propanol, Glycerolglycide, CAS no. 556-52-5 | |
| Glycerol Carbonate | 4-(Hydroxymethyl)-1,3-dioxolan-2-one, CAS no. 931-40-8, EC 213-235-0 | |
| para-Toluene Sulfonic Acid | Toluene 4-Sulfonic Acid, CAS no. 6192-52-5, EC 203-180-0 | HOTos |
| 3-aminopropan-1-ol | 3-amino-1-propanol, CAS no. 156-87-6, EC 205-864-4 | |
| 1,1-Carbonyl-diimidazolide | 1,1-Carbonylbisimidazol, 1,1′-Carbonylbis-1H-imidazol, N,N′-Carbonylbisimidazol, CAS no. 530-62-1, EC 208-488-9 | CDI |
| UDMA | 7,7,9 (resp. 7,9,9,)Trimethyl-4,13-dioxo-3,14-dioxa-5,12-diaza-hexadecane-1,16-diol dimethacrylate (mixture of isomers), CAS no. 72869-86-4, EC 276-957-5 | Co1 |
| DDDMA | Dodecane-1,12-diol dimethacrylate, 1,12-Dodecanediyl bismethacrylate, 2-Propenoic acid, 2-methyl, 1,12-dodecanediyl ester, CAS no. 72829-09-5, EC 276-900-4 | Co2 |
| Orthophosphoric Acid | Phosphoric Acid, ≥85 wt.-% in water, CAS no. 7664-38-2, EC | |
| APrA-TS | 3-Acryoyloxypropyl-ammonium Tosylate | |
| APA-TS | 5-Acryoyloxypentyl-ammonium Tosylate | |
| MAPrA-TS | 3-Methacroyloxypropyl-ammonium Tosylate | |
| MAPA-TS | 5-Methacroyloxypentyl-ammonium Tosylate | |

General Procedure A:
Synthesis of Precursors (e.g. E2T) via Etherification of Dihydroxybenzenes (e.g. Resorcinol) or Hydroxyalkylphenols (e.g. Tyrosol) or Hydroxybenzoic Acids (e.g. mHB) or via Nucleophilic Esterification of Hydroxybenzoic Acids (e.g. mHB) with Halogenated Alcohols (e.g. 3-Chloro-1-propanol)

To a solution of the corresponding Dihydroxybenzene or Hydroxyalkylphenol and the corresponding Halogenated Alcohol/s in water an aqueous solution of alkaline hydroxide (e.g. NaOH) or alkaline carbonate (e.g. Na2CO3) or ammonia is added at reflux. Optionally the synthesis can be done under a protective gas atmosphere (e.g. nitrogen).

Alternatively IPA or tBuOH can be used as solvent and solid alkaline hydroxide (e.g. KOH) or alkaline carbonate (e.g. Na2CO3) as base.

Also a subsequent reaction pattern is possible for Dihydroxybenzenes or Dihydroxybenzene Monoesters (e.g. RAc) where in the first reaction step one equivalent of base and one half of the Halogenated Alcohol/s is reacted with the Dihydroxybenzene or Dihydroxybenzene Monoester and afterwards in the second reaction step another equivalent of base and the remaining half of the Halogenated Alcohol/s is reacted (if a Dihydroxybenzene Monoester is used then after the first reaction step an ester hydrolysis, e.g. a basic ester hydrolysis, has to be done before the second reaction step can occur).

After stirring over night at reflux the reaction mixture is cooled to room temperature, and the reaction mixture is extracted (e.g. MTBE or EA or MEK) if water is used as solvent. Optionally the reaction mixture can be extracted as it is or the organic phase can be separated and only the aqueous phase can be extracted, afterwards the organic phase is combined with the extracts. Optionally the combined organic phases can be extracted with aqueous alkaline (e.g. NaOH) solutions and/or aqueous acid (e.g. $H_2SO_4$) solutions and/or water.

If IPA or tBuOH is used as solvent the reaction mixture is first filtered to remove the precipitate, then the solvent is stripped off in vacuo, and then the residue is extracted against water as described above.

If a Hydroxybenzoic Acid is used as building block first the reaction mixture is acidified with aqueous acid (e.g $H_2SO_4$) and then extracted against water as described above to isolate the etherification product Hydroxyalkoxybenzoic Acid and/or the nucleophilic esterification product Hydroxybenzoic Acid Hydroxyalkyl Ester.

Optionally the combined organic phases are filtered through silica or alumina and/or are stirred with charcoal to achieve improved decolorization. After drying over anhydrous Na2SO4 and filtration the solvent is stripped off in vacuo.

Alternatively an alkylation according to the so-called Carbonate Method according to Houben-Weyl, Methoden der Organischen Chemie, Band VI/3 Teil 3, Sauerstoffverbindungen 1, 4. Auflage, 1965, Georg Thieme Verlag, Stuttgart, p. 55, or a deacylating alkylation of mono or diacylated Dihydroxybenzenes (e.g. RAc or RAc2) according to Houben-Weyl, Methoden der Organischen Chemie, Band VI/3 Teil 3, Sauerstoffverbindungen 1, 4. Auflage, 1965, Georg Thieme Verlag, Stuttgart, p. 59, is possible.

General Procedure B:
Synthesis of Precursors (e.g. OER) via Etherification of Already Alkoxylated Dihydroxybenzenes (e.g. ethoxylated resorcinol) with Halogenated Alcohols (e.g. 3-Chloro-1-propanol)

Under a protective gas atmosphere (e.g. nitrogen) to a mixture of the corresponding Already Alkoxylated Dihydroxybenzene and the corresponding Halogenated Alcohol/s a solution of KOtBu in e.g. THF or tBuOH is added slowly at elevated temperature (e.g. 80° C.). After stirring over night at elevated temperature the reaction mixture is cooled to room temperature, the precipitate is separated by filtration, and the solvent is stripped off from the filtrate in vacuo. Optionally further purification of this residue via an aqueous workup as described in General Procedure A can be achieved.

General Procedure C:
Synthesis of Ethoxylated Precursors (e.g. ET) or Glycerylated Precursors (e.g. GT) Via Etherification of Dihydroxybenzenes (e.g. BC) or Hydroxyalkylphenols (e.g. Tyrosol) with Ethylene Carbonate or Glycerol Carbonate To a solution of the corresponding Dihydroxybenzene or Hydroxyalkylphenol and Ethylene Carbonate or Glycerin Carbonate in IPA or tBuOH solide alkaline hydroxide (e.g. KOH) or alkaline carbonate (e.g. K2CO3) or alkaline tert-butoxide (e.g. KOtBu) is added and the reaction mixture is stirred at reflux over night. Optionally the synthesis can be done under a protective gas atmosphere (e.g. nitrogen).

The reaction mixture is cooled to room temperature, the solvent is stripped off in vacuo, and then the residue is extracted against water and further worked up as described in General Procedure A. Optionally the isolated product can be further purified by crystallization using water as solvent.

General Procedure D:
Synthesis of Precursors (e.g. PGT or GT) via Addition of Dihydroxybenzenes (e.g. BC) or Hydroxyalkylphenols (e.g. Tyrosol) or Hydroxybenzoic Acids (e.g. mHB) or Already Etherified and/or Nucleophilic Esterified Hydroxybenzoic Acids (e.g. OmHB) onto Epoxies (e.g. GP or Glycidol) under Ring-Opening Solvent Base Route: To an aqueous solution of the corresponding Hydroxyalkylphenol (e.g. Tyrosol) and alkaline hydroxide (e.g. NaOH) or alkaline carbonate (e.g. Na2CO3) or ammonia the epoxy (e.g. GP) is added at reflux. Optionally the synthesis can be done under a protective gas atmosphere (e.g. nitrogen). Optionally the synthesis can be done using IPA or HOtBu as solvent and solid alkaline hydroxide (e.g. KOH) or alkaline carbonate (e.g. K2CO3) or alkaline tert-butoxide (e.g. KOtBu). After stirring over night at reflux the reaction mixture is cooled to room temperature, and the reaction mixture is extracted and further worked up as described in General Procedure A.

Solvent Free Route: To the mixture of the corresponding Dihydroxybenzenes (e.g. BC) and the epoxy (e.g. GP) a catalyst (e.g. $PPh_3$ or TEA) is added under stirring and the reaction mixture is warmed to an elevated temperature. Optionally the synthesis can be done under a protective gas atmosphere (e.g. nitrogen). After stirring over night at elevated temperature the reaction mixture is cooled to room temperature, and the reaction mixture is extracted and further worked up as described in General Procedure A.

Optionally the isolated product can be further purified by crystallization using water as solvent or by fractionated subsequent organic-organic extraction using organic solvents of different polarities.

General Procedure E:
One Step Reaction of Precursors (e.g. PGT or GT) with an Isocyanato Functional (Meth)acrylate Building Block (e.g. IEM)

To the corresponding Precursor 200-640 ppm of BHT and 100 ppm of bismuth neodecanoate (Bi-Cat, 20 wt.-% of bismuth, 100 ppm with respect to the amount of bismuth alone) are added. At a temperature of about 50° C. e.g. IEM is added while stirring so that the temperature does not exceed about 55° C. After completion of the addition the reaction mixture is stirred for at least additional about 16 hours at a temperature of about 50° C. until completion of the addition reaction (measured via FTIR: the corrected height of the NCO band at about 2270 cm-1 is below 0.05).

General Procedure F:

Synthesis of an Ammonium Functional (Meth)acrylate Building Block (e.g. MAPrA-TS)

Out of a mixture of para-toluene sulfonic acid monohydrate (HOTos), e.g. 3-aminopropan-1-ol, and methacrylic acid (MA) in toluene water is stripped off using a Dean-Starck apparatus. After completion of the reaction the product (e.g. MAPrA-TS) crystallizes during cooling. The precipitate is separated by filtration, washed with toluene, and dried in vacuo.

General Procedure G:

Two Step One Pot Reaction of Precursors (e.g. PGT or GT) with an Ammonium Functional (Meth)acrylate Building Block (e.g. MAPrA-TS)

To a solution of the corresponding Precursor in toluene CDI is added and the resulting mixture is stirred over night. Orthophosphoric acid is added and the colorless precipitate of imidazolium dihydrogenphosphate is removed by filtration. To the filtrate (a solution of the diimidazolide of the corresponding Precursor) 500-2000 ppm of HQME, 200-1000 ppm of BHT, and e.g. MAPrA-TS are added. The resulting mixture is stirred over night at a temperature of about 80° C. At room temperature the colorless precipitate of imidazolium tosylate is removed by filtration. The filtrate is subsequently extracted with phosphoric acid, sodium hydroxide solution, phosphoric acid, and water. After stirring over night with charcoal and filtration through acidic alumina 100-500 ppm of HQME and 100-500 ppm of BHT are added to the filtrate and the solvent is stripped off in vacuo while bubbling air through the crude product.

General Procedure H:

Acid Catalyzed (e.g. MSA) Esterification of Hydroxy Functional Building Blocks (e.g. T, S, or iS) with Unsaturated Acids (e.g. MA)

To the corresponding Hydroxy Functional Building Block in e.g. cyclohexane or a hexane/toluene mixture or a cyclohexane/toluene mixture BHT, HQME, optionally methylene blue and/or HQ, the catalyst (e.g. MSA) and the unsaturated acid (e.g. MA) are added. At reflux water is removed using a Dean Starck apparatus. After completion of the reaction the crude reaction mixture is extracted at least twice with 4N NaOH solution or 2N NaOH solution, then at least once washed with water, and then dried over anhydrous Na2SO4. After filtration, the filtrate is optionally filtered through basic alumina. 100-300 ppm of BHT and 100-300 ppm of HQME are added to the filtrate. Then the solvent is stripped off in vacuo while air is bubbling through the crude sample.

ERGP-IEM (Comparative Example 1)

Synthesis according to WO 2012/003136, page 52.

PGS-IEM (Inventive Example 1)

According to General Procedure D (Solvent Based Route) 51.5 g of S, 3.30 g of NaOH, and 61.1 g of GP were reacted in 150 mL of water to give 90.3 g of PGS. According to General Procedure E 50.0 g of PGS and 55.4 g of IEM were reacted to give 101.7 g of PGS-IEM.

PGiS-IEM (Inventive Example 2)

According to General Procedure D (Solvent Based Route) 34.7 g of iS, 2.30 g of NaOH, and 42.40 g of GP were reacted in 70 mL of water to give 65.3 g of PGiS. According to General Procedure E 30.0 g of PGiS and 33.3 g of IEM were reacted to give 62.3 g of PGiS-IEM.

PGT-IEA (Inventive Example 3)

According to General Procedure D (Solvent Based Route) 100.0 g of tyrosol, 5.73 g of NaOH, and 108.0 g of GP were reacted in 200 mL of water to give 203.4 g of crude PGT. After re-crystallization from water 188.9 g of purified PGT were collected. According to General Procedure E 18.4 g of purified PGT and 17.7 g of IEA were reacted to give 31.9 g of PGT-IEA.

PGT-IEM (Inventive Example 4)

According to General Procedure D (Solvent Based Route) 100.0 g of tyrosol, 5.73 g of NaOH, and 108.0 g of GP were reacted in 200 mL of water to give 203.4 g of crude PGT. After re-crystallization from water 188.9 g of purified PGT were collected. According to General Procedure E 48.2 g of purified PGT and 50.8 g of IEM were reacted to give 93.9 g of PGT-IEM.

PGT-IPrA (Inventive Example 5)

According to General Procedure D (Solvent Based Route) 100.0 g of tyrosol, 5.73 g of NaOH, and 108.0 g of GP were reacted in 200 mL of water to give 203.4 g of crude PGT. After re-crystallization from water 188.9 g of purified PGT were collected. According to General Procedure G 32.4 g of purified PGT, 37.1 g of CDI, 26.0 g of orthophosphoric acid, and 71.1 g of APrA-Ts were reacted in 200 ml of toluene to give 54.1 g of PGT-IPrA.

PGT-IProM (Inventive Example 6)

According to General Procedure D (Solvent Based Route) 100.0 g of tyrosol, 5.73 g of NaOH, and 108.0 g of GP were reacted in 200 mL of water to give 203.4 g of crude PGT. After re-crystallization from water 188.9 g of purified PGT were collected. According to General Procedure G 55.1 g of purified PGT, 63.1 g of CDI, 44.3 g of orthophosphoric acid, and 127 g of MAPrA-Ts were reacted in 300 ml of toluene to give 87.7 g of PGT-IProM.

PGTM-IEM (Inventive Example 7)

According to General Procedure H 136.8 g of tyrosol, 125.3 g of MA, and 8.90 g of MSA were reacted to give 183.4 g of TM. According to General Procedure D (Solvent Free Route) 20.0 g of TM, 0.17 g of TEA, and 14.7 g of GP were reacted to give 32.3 g of PGTM. According to General Procedure E 24.3 g of PGTM and 10.5 g of IEM were reacted to give 36.5 g of PGTM-IEM.

GT-IEM (Inventive Example 8)

According to General Procedure D (Solvent Based Route) 80.0 g of tyrosol, 7.49 g of KOH, and 46.0 g of glycidol were reacted in 100 mL of IPA to give 112.3 g of GT. According to General Procedure E 50.0 g of GT and 73.1 g of IEM were reacted to give 117 g of GT-IEM.

PGT-IPM (Inventive Example 9)

According to General Procedure D (Solvent Based Route) 100.0 g of tyrosol, 5.73 g of NaOH, and 108.0 g of GP were reacted in 200 mL of water to give 203.4 g of crude PGT. After re-crystallization from water 188.9 g of purified PGT were collected. According to General Procedure G 55.0 g of purified PGT, 63.0 g of CDI, 44.2 g of orthophosphoric acid, and 138 g of MAPA-Ts were reacted in 300 ml of toluene to give 95.1 g of PGT-IPM.

PGTM-IProM (Inventive Example 10)

According to General Procedure H 136.8 g of tyrosol, 125.3 g of MA, and 8.90 g of MSA were reacted to give 183.4 g of TM. According to General Procedure D (Solvent Free Route) 92.2 g of TM, 0.81 g of TEA, and 67.5 g of GP were reacted to give 143.4 g of PGTM. According to General Procedure G 100 g of PGTM, 46.3 g of CDI, 32.4 g of orthophosphoric acid, and 92.9 g of MAPrA-Ts were reacted in 300 ml of toluene to give 129 g of PGTM-IProM.

PGTM-IPM (Inventive Example 11)

According to General Procedure H 136.8 g of tyrosol, 125.3 g of MA, and 8.90 g of MSA were reacted to give 183.4 g of TM. According to General Procedure D (Solvent Free Route) 92.2 g of TM, 0.81 g of TEA, and 67.5 g of GP were reacted to give 143.4 g of PGTM. According to General Procedure G 50 g of PGTM, 23.2 g of CDI, 16.2 g of orthophosphoric acid, and 50.6 g of MAPA-Ts were reacted in 300 ml of toluene to give 57.3 g of PGTM-IPM.

BCGP-IPM (Inventive Example 12)

According to General Procedure D (Solvent Free Route) 42.8 g of 4-tert-butylcatechol, 0.59 g of TEA, and 75.0 g of GP were reacted at a temperature of 80° C. to give 114.3 g of BCGP. According to General Procedure G 54.2 g of BCGP, 38.3 g of CDI, 13.4 g of orthophosphoric acid, and 41.7 g of MAPA-Ts were reacted in 300 ml of toluene to give 63.8 g of BCGP-IPM.

Light Curing One Component Compositions

Some of the compounds synthesized were used for producing a (dental) composition.

The compositions produced and tested with respect to their mechanical properties are given in Tables 2 and 3 below. In Tables 2 and 3 the values of the components represent %-weight of the individual components in the corresponding dental formulation.

General Procedure I:

With magnetic stirring and under the exclusion of light the initiator system components were dissolved within the monomers at temperatures not above 50° C. (depending on the intrinsic viscosity of the used monomers).

General Procedure II:

According to General Procedure I the initiator system components were dissolved within the monomers. Under the exclusion of light and using a two-arm kneader the filler was mixed in portions with this mixture of initiator system and monomers. The amount of filler was manually determined depending on the desired handling properties of the dental composition. The dental composition was then light cured using a 800 mW halogen curing light (3M ESPE Elipar™ Trilight) and tested according to the corresponding measurements listed above. The respective values are given in Table 2.

Dental Composition A contains component CE1 but not compound (A) according to the invention. In Table 2 below, compound (A) is represented by components IE1 to IE8. Thus, Dental Composition A can be considered as Comparative Example, whereas Dental Compositions B to I can be considered as Inventive Examples.

TABLE 2

| | Dental Composition | | | | | | | | |
|---|---|---|---|---|---|---|---|---|---|
| | A | B | C | D | E | F | G | H | I |
| CE1 | 17.9 | | | | | | | | |
| IE1 | | 17.9 | | | | | | | |
| IE2 | | | 17.9 | | | | | | |
| IE3 | | | | 17.9 | | | | | |
| IE4 | | | | | 17.9 | | | | |
| IE5 | | | | | | 17.9 | | | |
| IE6 | | | | | | | 17.9 | | |
| IE7 | | | | | | | | 17.9 | |
| IE8 | | | | | | | | | 17.9 |
| Co1 | 3.78 | 3.78 | 3.78 | 3.78 | 3.78 | 3.78 | 3.78 | 3.78 | 3.78 |
| Co2 | 1.89 | 1.89 | 1.89 | 1.89 | 1.89 | 1.89 | 1.89 | 1.89 | 1.89 |
| Ini1 | 0.05 | 0.05 | 0.05 | 0.05 | 0.05 | 0.05 | 0.05 | 0.05 | 0.05 |
| Ini2 | 0.07 | 0.07 | 0.07 | 0.07 | 0.07 | 0.07 | 0.07 | 0.07 | 0.07 |
| Ini3 | 0.26 | 0.26 | 0.26 | 0.26 | 0.26 | 0.26 | 0.26 | 0.26 | 0.26 |
| F1 | 7.22 | 7.22 | 7.22 | 7.22 | 7.22 | 7.22 | 7.22 | 7.22 | 7.22 |
| F2 | 68.8 | 68.8 | 68.8 | 68.8 | 68.8 | 68.8 | 68.8 | 68.8 | 68.8 |
| Stress [μstrain] | 2035 ± 132 | 2063 ± 108 | 2144 ± 137 | 2309 ± 23 | 2021 ± 63 | 2265 ± 37 | 2255 ± 139 | 2228 ± 96 | 2224 ± 84 |
| CS [MPa] | 367 ± 34.0 | 396 ± 36.0 | 414 ± 25.0 | 443 ± 23.0 | 397 ± 7.00 | 451 ± 21.0 | 405.0 ± 22.0 | 386 ± 13.0 | 401 ± 18.0 |

As can be seen, compositions containing compound (A) according to the invention are superior with respect to certain properties compared to compositions not containing compound (A) according to the invention.

The invention claimed is:

1. A dental composition comprising:
   polymerizable monomer (1);
   initiator;
   filler component(s) in an amount of more than about 20 wt.-%, with respect to the whole weight of the composition;
   the polymerizable monomer (1) being characterized as follows:
   having exactly two (meth)acrylate reactive moieties;
   having an unsymmetrical backbone as linkage between the (meth)acrylate reactive moieties;
   the two (meth)acrylate reactive moieties being attached onto the unsymmetrical monomer backbone as alkyl esters;
   the unsymmetrical backbone comprising one aromatic moiety of the phenolic type;
   having one or two urethane moieties within the unsymmetrical backbone;
   the polymerizable monomer (1) not containing:
   an acidic moiety;
   other atoms than carbon, hydrogen, nitrogen, and oxygen;
   a bisphenol moiety;

the polymerizable monomer (1) being characterized by formula (I)

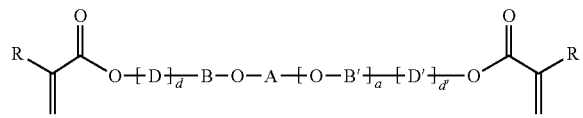

with:
a=0 or 1,
A=

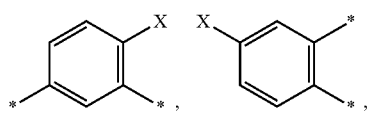

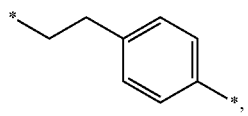

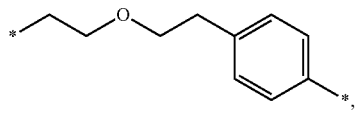

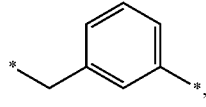

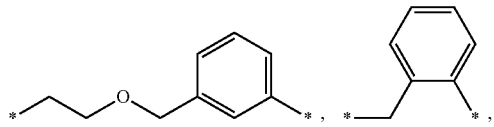

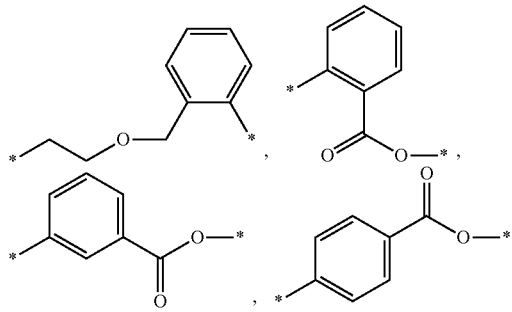

A being always attached as aryl-alkyl ether onto B and / or B',

B=*—(CH$_2$)$_b$—* , *—(CH$_2$—CH$_2$—O—CH$_2$—CH$_2$)—* , *—(CH$_2$—CH$_2$—O—CH$_2$—CH$_2$—CH$_2$)—* , *—(CH$_2$—CH$_2$—CH$_2$—O—CH$_2$—CH$_2$—CH$_2$)—*,

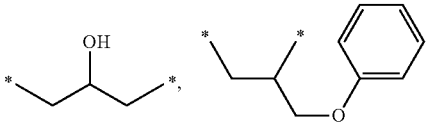

B being attached as alkyl ester onto the (meth)acrylate reactive group or as urethane onto D, b=2 to 6, B'=*—(CH$_2$)$_{b'}$—* , *—(CH$_2$—CH$_2$—O—CH$_2$—CH$_2$)—* ,

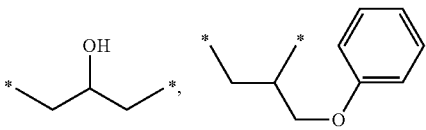

B' being attached as alkyl ester onto the (meth)acrylate reactive group or as urethane onto D', b'=2- 6, D, D' being independently selected from *—(CH$_2$)n—NH—(C=O)—O—* , *—(CH$_2$—C(CH$_3$)$_2$—CH$_2$)—NH—(C=O)—O—* , *—(CH$_2$—CH$_2$—C(CH$_3$)$_2$)—NH—(C=O)—O—*

D and D' being always attached via the oxygen of the urethane linkage onto B and/or B', d=0 or 1 and d'=0 or 1 with the proviso that (d+d')=1 or 2, n=2 to 5, R being independently selected from H, methyl, X being independently selected from H and C1 to C6 alkyl, "*" representing those site(s) of a moiety of the monomer, where that moiety is bonded to another moiety of the monomer, wherein the polymerizable monomer (1) being selected from one of the following monomers and mixtures thereof:

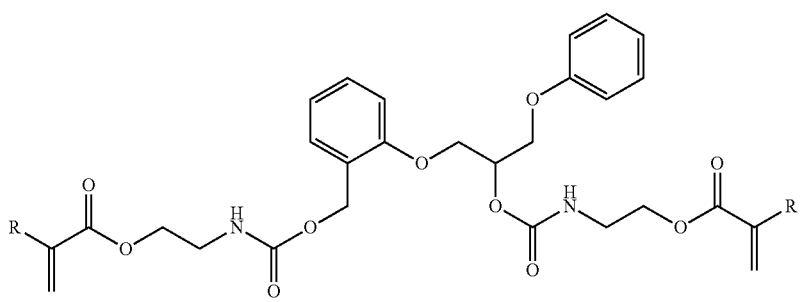

-continued
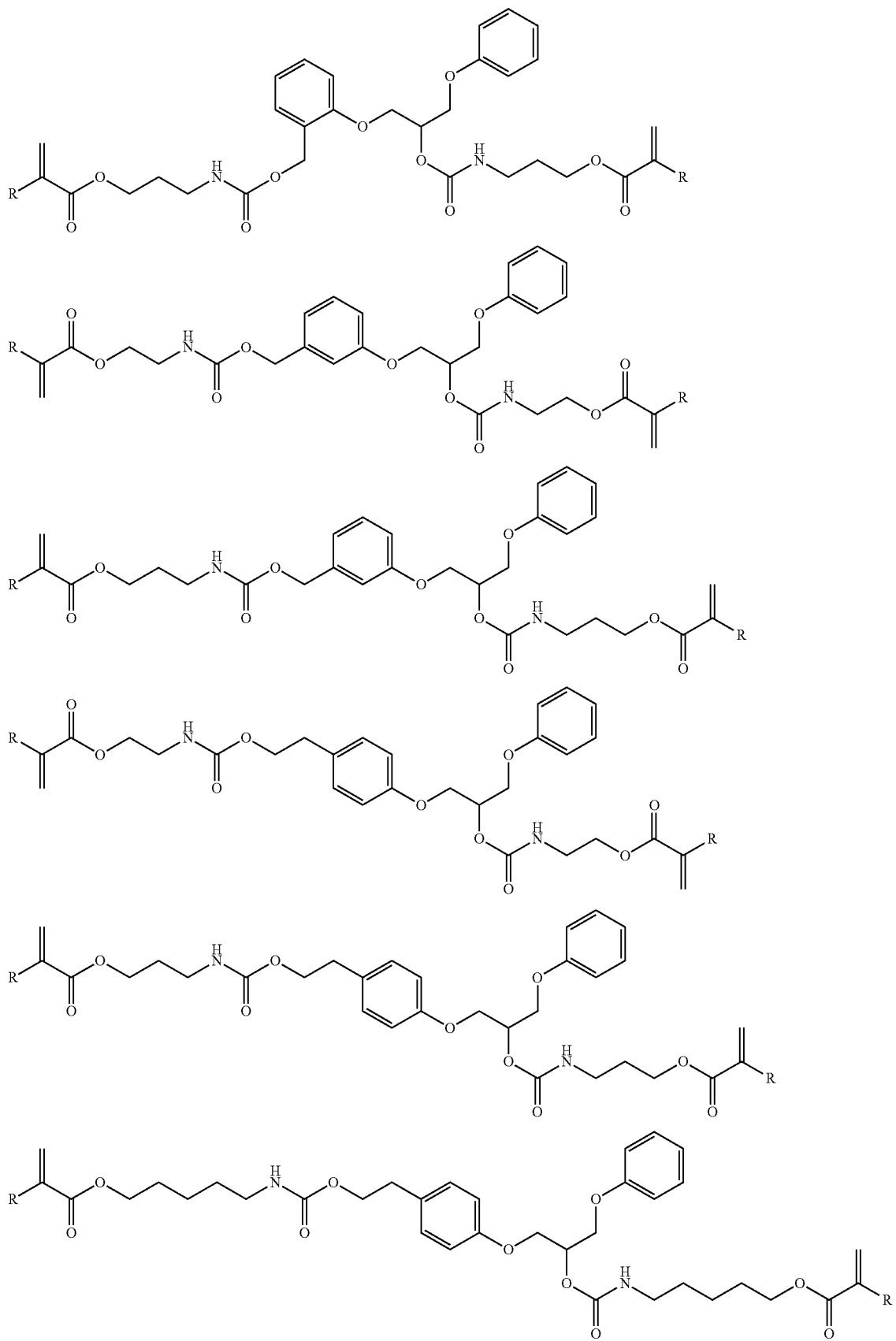

-continued
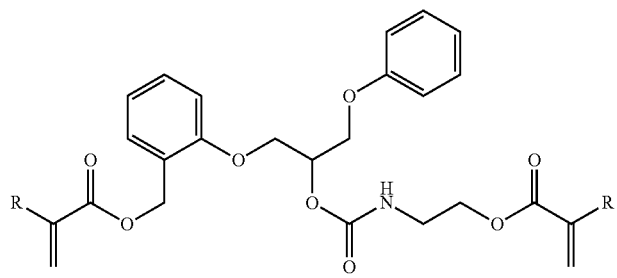
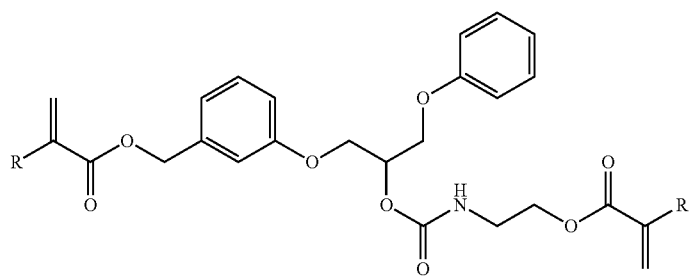
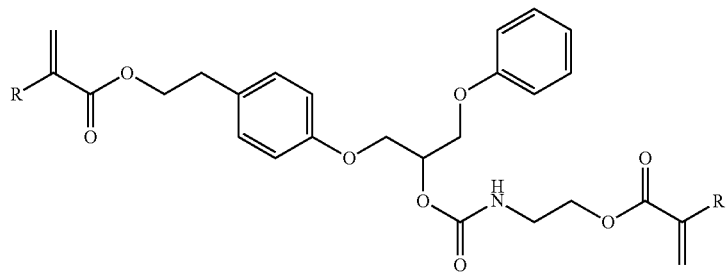
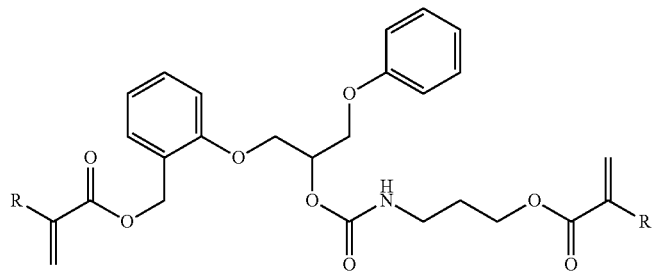
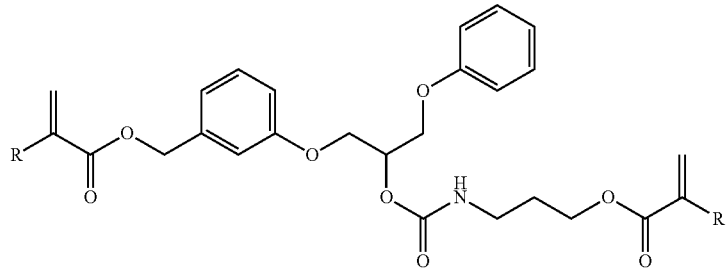
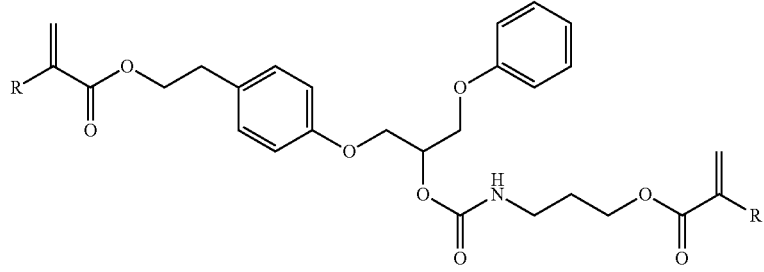

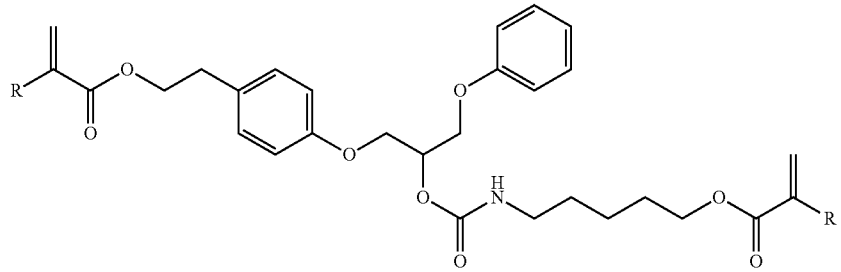
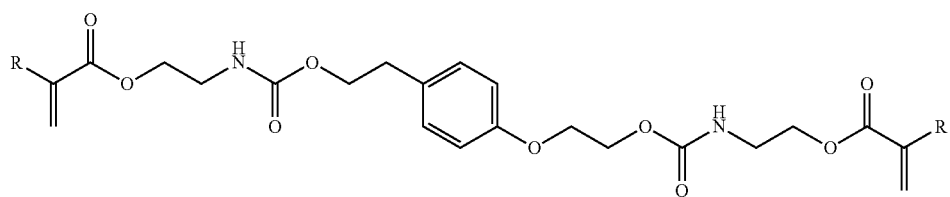
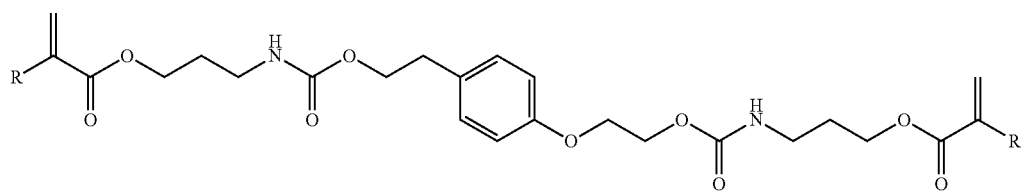
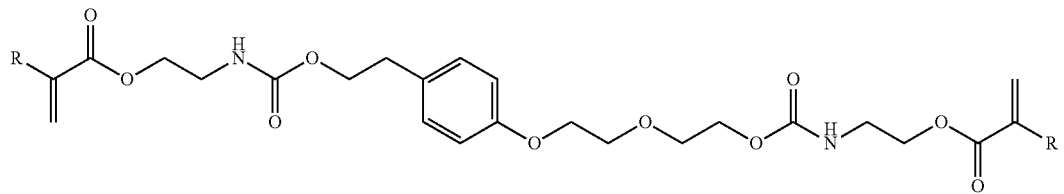
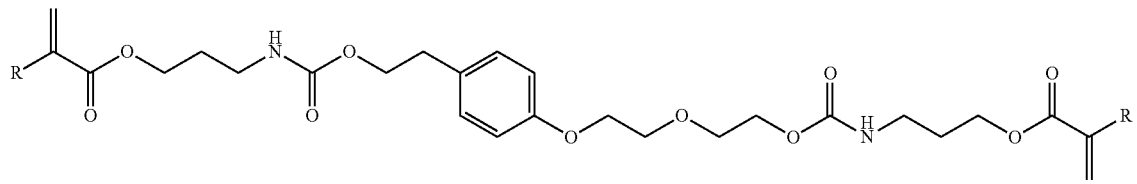
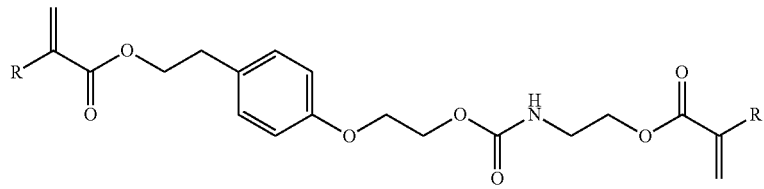
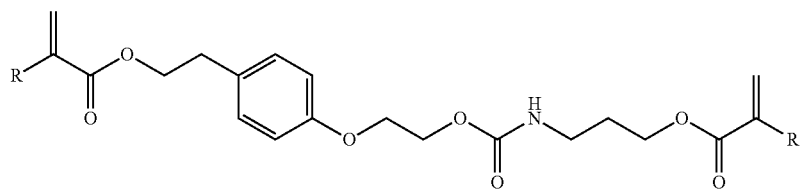
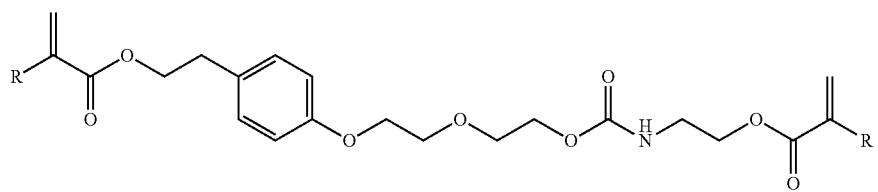

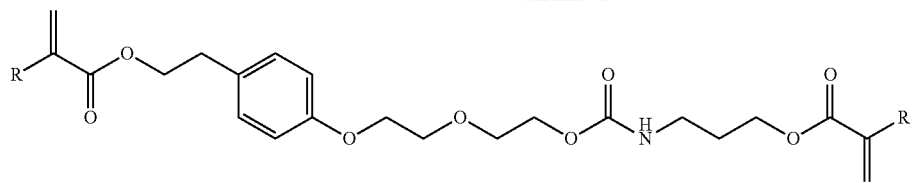
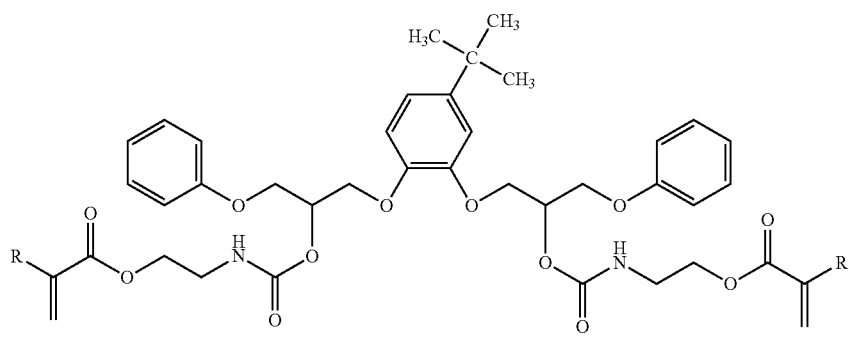
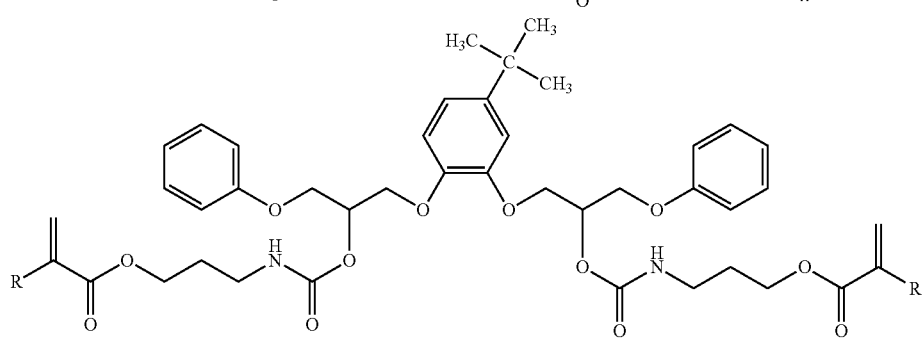
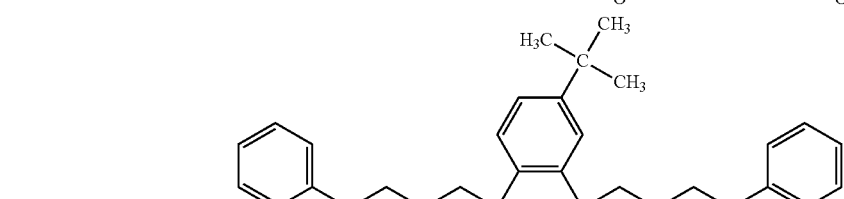
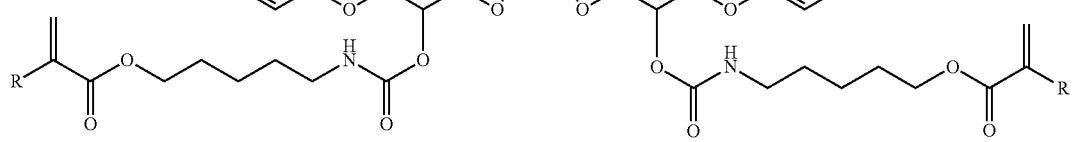
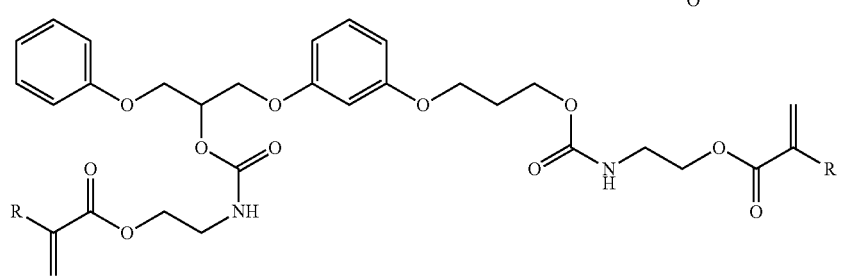
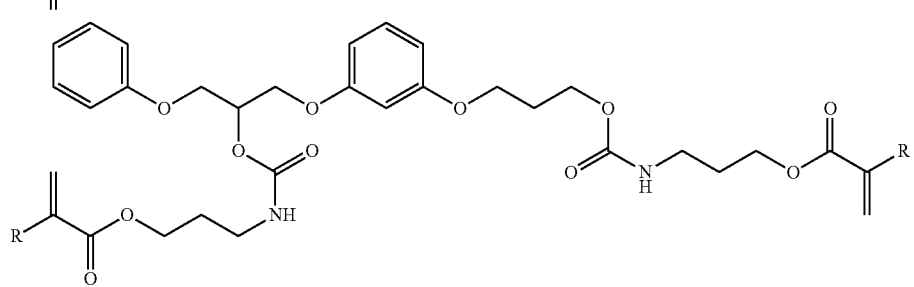

-continued
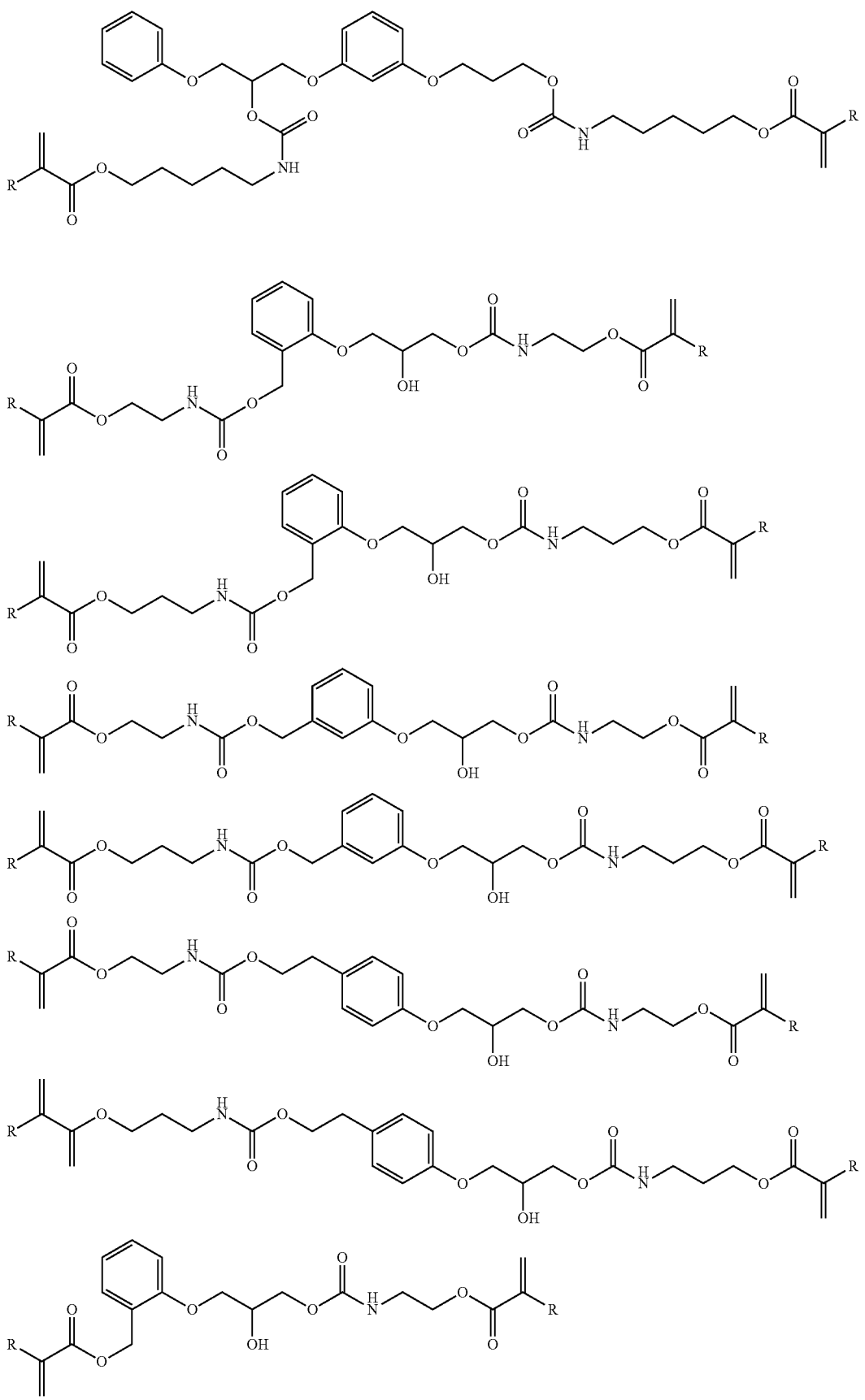

-continued
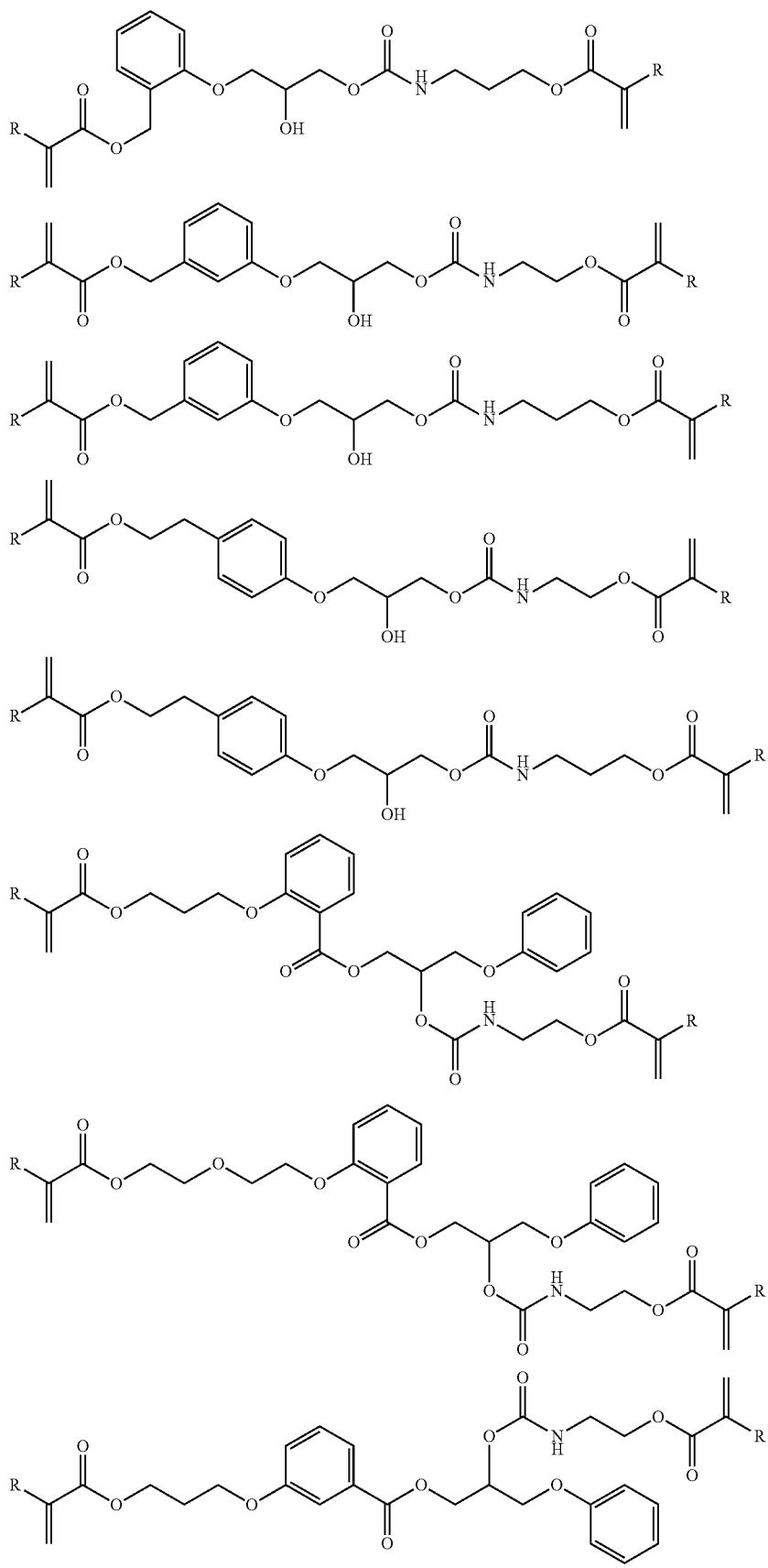

-continued
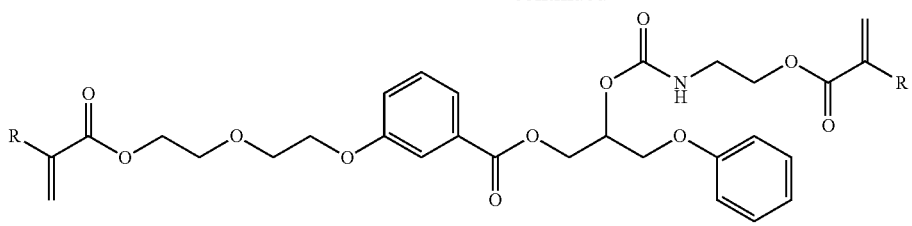
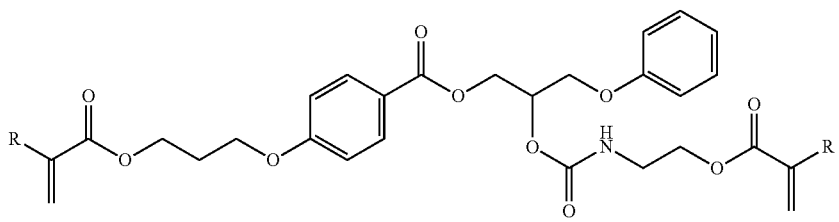
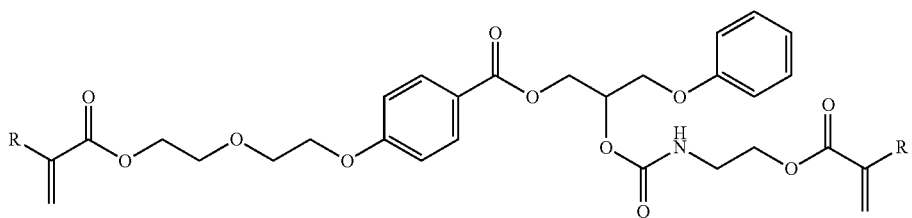
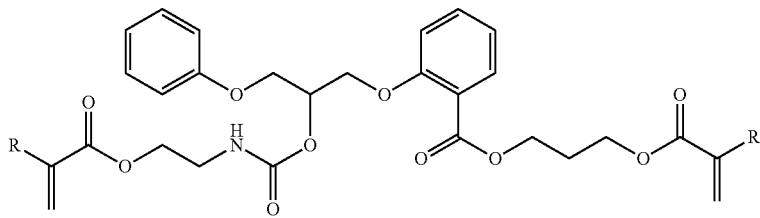
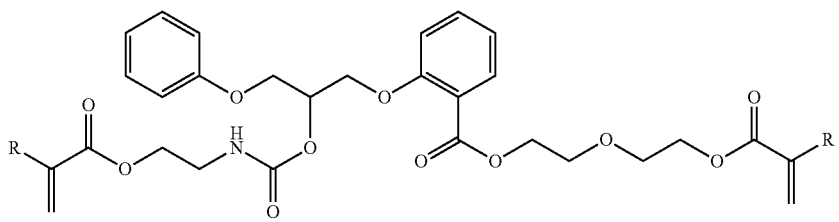
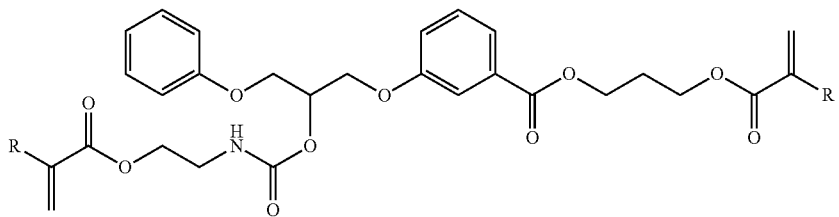
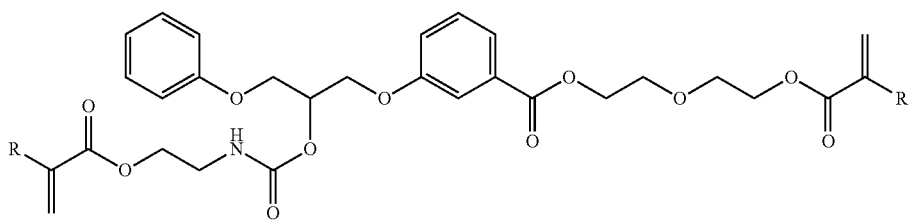

-continued
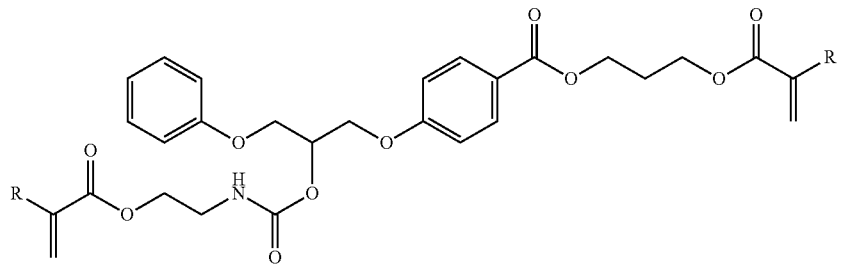
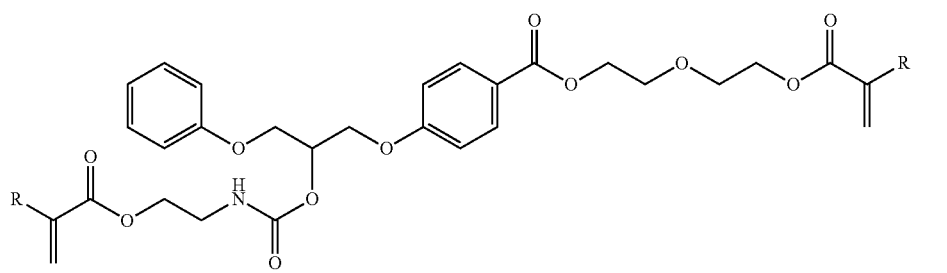
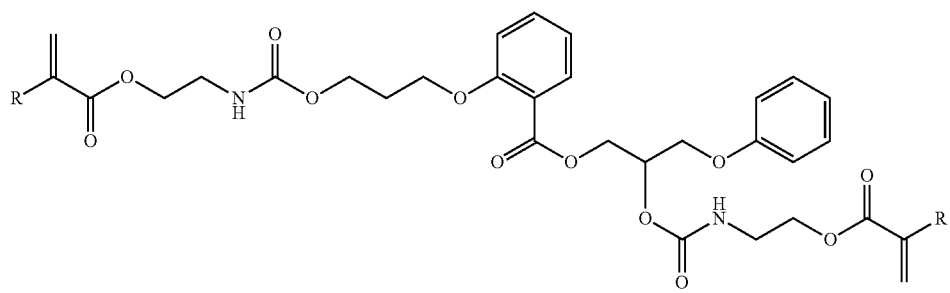
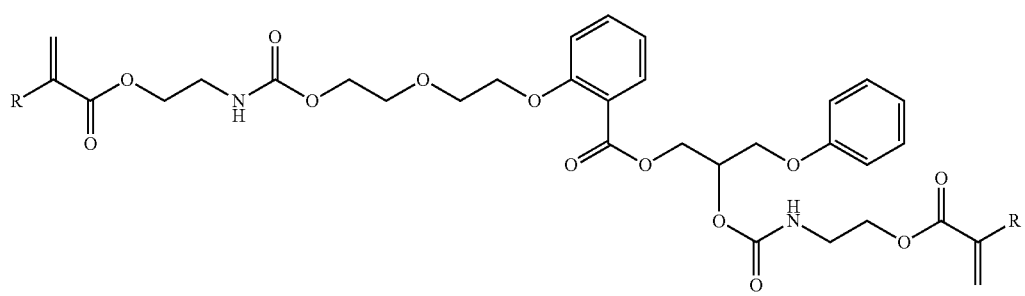
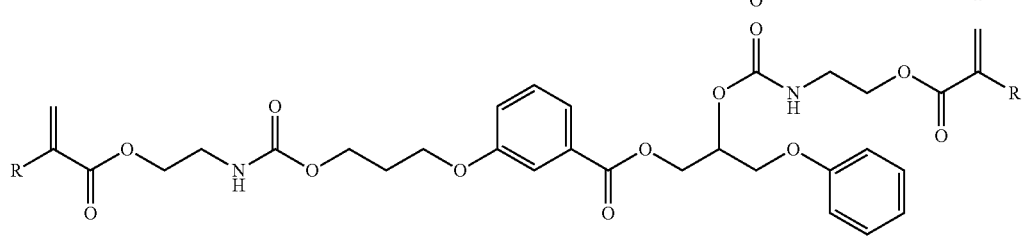
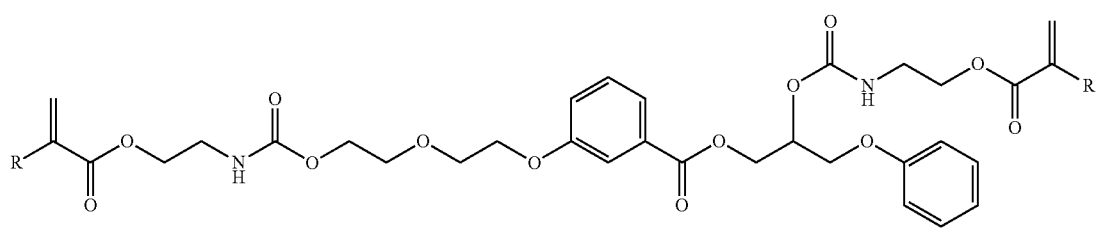

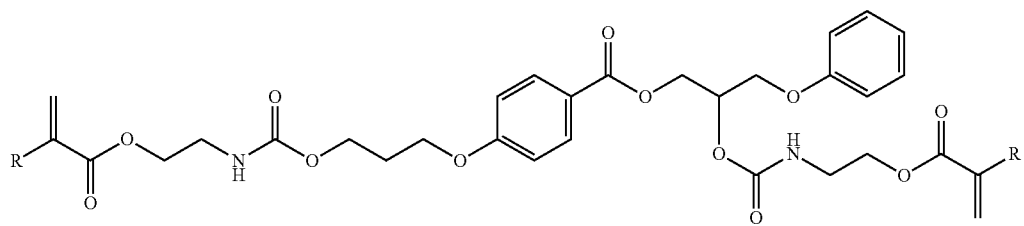
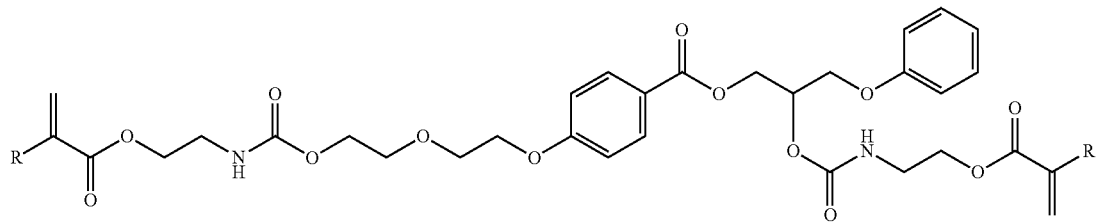
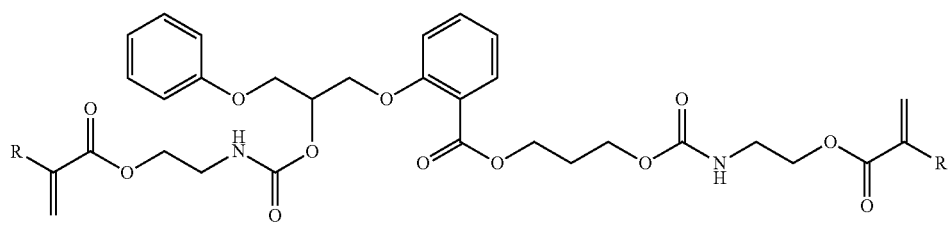
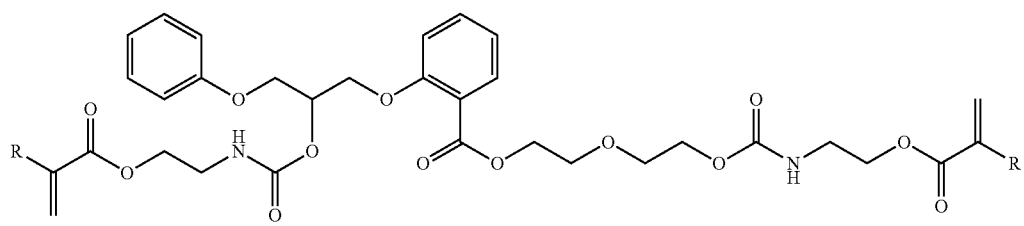
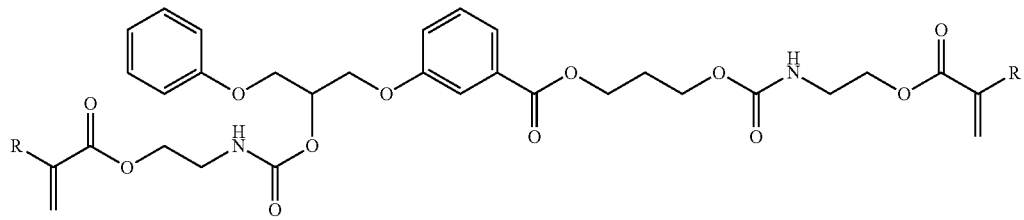
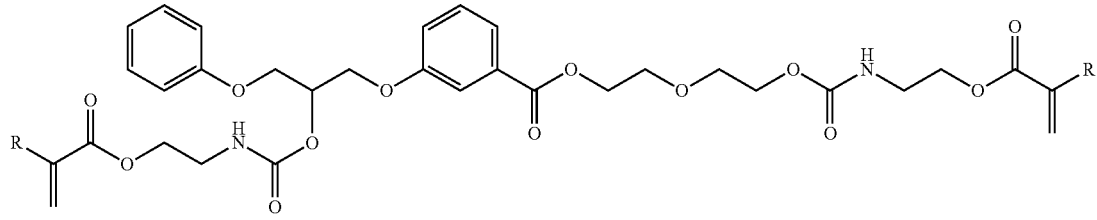
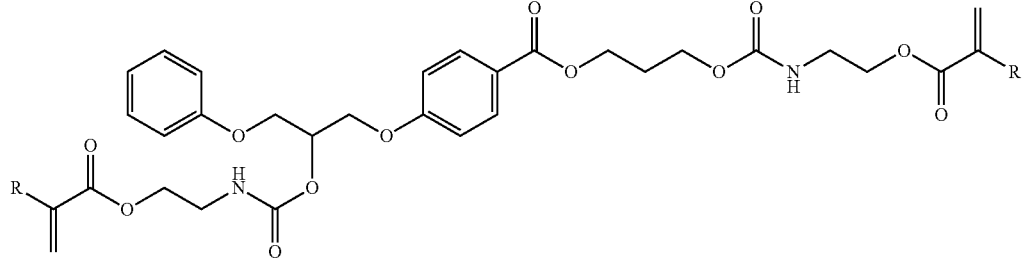

-continued with R being independently selected from H and methyl.

2. The dental composition of claim 1, the initiator being selected from radiation curing, redox curing, heat curing initiators and combinations thereof.

3. The dental composition of claim 1, comprising the respective components in the following amounts:
polymerizable monomer(s) (1): from about 1 to about 75 wt.-%,
initiator(s): from about 0.1 to about 10 wt.-%, and
filler(s): from about 20 to about 95 wt.-%.

4. The dental composition of claim 1 further comprising a polymerizable monomer (2) bearing an acidic moiety.

5. The dental composition of claim 1, not comprising either or all of the following components:
Bis-GMA or bisphenol moiety(s) containing components in an amount above 5 wt.-%,
Solvent(s) in an amount above 5 wt.-%.

6. The dental composition of claim 1, the adhesive composition being characterized by at least one or all of the following features after curing:
compressive strength: at least about 380 MPa;
shrinkage stress: not more than about 2350 μstrain.

7. The dental composition of claim 1 being characterized as follows:
polymerizable monomer(s) (1) being represented by the formula as described in claim 1 in an amount from about 1 to about 75 wt.-%,
initiator(s) being selected from radiation curing or redox curing initiators,
filler(s) being selected from silica, silica/zirconia filler(s) and mixtures thereof in an amount from about 20 to about 90 wt.-%.

8. The dental composition of claim 1 being provided as one or two part system.

9. The dental composition of claim 1 being in a cured state and being provided in the shape of a dental crown, bridge, inlay, onlay, veneer, orthodontic device or dental mill blank.

10. A process for performing a dental procedure comprising:
providing the dental composition of claim 1; and
producing a dental filling material, dental cement, crown and bridge material, inlay, onlay, veneer, orthodontic device or dental mill blank.

11. A process for producing a dental mill blank, the process comprising:
providing a dental composition of claim 1, the dental composition being in its uncured state;
hardening or curing the dental composition to obtain a hardened or cured dental composition;
fixing the hardened dental composition to a holding device; and
the dental composition being provided in the shape of a dental mill blank.

12. A process for producing a dental restoration, the process comprising:
providing a dental mill blank, the dental mill blank comprising the dental composition of claim 1, the dental composition being in its cured state; and
machining the dental mill blank to obtain a dental restoration.

* * * * *

UNITED STATES PATENT AND TRADEMARK OFFICE
CERTIFICATE OF CORRECTION

PATENT NO. : 10,010,488 B2
APPLICATION NO. : 15/116873
DATED : July 3, 2018
INVENTOR(S) : Eckert et al.

Page 1 of 3

It is certified that error appears in the above-identified patent and that said Letters Patent is hereby corrected as shown below:

In the Specification

Column 1
Line 44, After "groups" insert -- . --.

Column 4
Line 42, Delete "C(O)O—" and insert -- —C(O)O— --, therefor.

Column 29
Line 31, After "wt.-%" insert -- , --.

Column 29
Line 33, After "wt.-%" insert -- , --.

Column 29
Line 65, Delete "linkages,and" and insert -- linkages, and --, therefor.

Column 30
Line 58, Delete "desoikcribed" and insert -- described --, therefor.

Column 32
Line 3, Delete "hexandiol" and insert -- hexanediol --, therefor.

Column 33
Line 64, Delete "different,stand" and insert -- different, stand --, therefor.

Column 34
Line 12, Delete "napthylphosphine" and insert -- naphthylphosphine --, therefor.

Signed and Sealed this
Twenty-third Day of April, 2019

Andrei Iancu
*Director of the United States Patent and Trademark Office*

CERTIFICATE OF CORRECTION (continued)

Column 34
Line 29, Delete "-naphthol)-" and insert -- -naphthoyl)- --, therefor.

Column 36
Line 17, Delete "4,4'-dihydroxylbenzil," and insert -- 4,4'-dihydroxybenzil, --, therefor.

Column 36
Line 20, Delete "acenaphthaquinone," and insert -- acenaphthoquinone, --, therefor.

Column 36
Line 46, Delete "photointiators" and insert -- photoinitiators --, therefor.

Column 37
Line 31, Delete "2,6-dibutyl4-" and insert -- 2,6-dibutyl-4- --, therefor.

Column 37
Lines 31-32, Delete "2,6-dimethyl4-" and insert -- 2,6-dimethyl-4- --, therefor.

Column 37
Line 32, Delete "2,6-dioctyl4-" and insert -- 2,6-dioctyl-4- --, therefor.

Column 37
Line 38, After "compounds" insert -- . --.

Column 37
Line 41, Delete "quarternary" and insert -- quaternary --, therefor.

Column 40
Line 23, Delete "Neazopon" and insert -- Neozapon --, therefor.

Column 41
Line 67, Delete "SulzerMixpac" and insert -- Sulzer Mixpac --, therefor.

Column 42
Line 12, Delete "SulzerMixpac" and insert -- Sulzer Mixpac --, therefor.

Column 44
Lines 1-4, Delete "being represented by a formula as described in the text above with respect to the polymerizable monomer (1) in an amount from about 1 to about 75 wt.-%, Radiation curing initiator(s), Filler(s) being selected from silica or silica/zirconia filler(s) in an amount from about 20 to about 95 wt.-%." and insert the same on Column 44, Line 2, as a new paragraph.

Column 100
Line 9, Delete "Via" and insert -- via --, therefor.

CERTIFICATE OF CORRECTION (continued)
U.S. Pat. No. 10,010,488 B2

Column 101
Line 8, Delete "Starck" and insert -- Stark --, therefor.

Column 101
Line 11, Delete "dried" and insert -- dryed --, therefor.

Column 101
Line 37 (approx.), Delete "Starck" and insert -- Stark --, therefor.

Column 101
Lines 54-55, Delete "According to General Procedure E 50.0 g of PGS and 55.4 g of IEM were reacted to give 101.7 g of PGS-IEM." and insert the same on Column 101, Line 53, as a continuation of the same paragraph.

In the Claims

Column 106
Lines 1-2, In Claim 1, "and / or" and insert -- and/or --, therefor.

Column 106
Line 3, In Claim 1, "—* ," and insert -- —*, --, therefor.

Column 106
Line 4, In Claim 1, "—* ," and insert -- —*, --, therefor.

Column 106
Line 5, In Claim 1, "—* ," and insert -- —*, --, therefor.

Column 106
Line 20, In Claim 1, "—* ," and insert -- —*, --, therefor.

Column 106
Line 21, In Claim 1, "—* ," and insert -- —*, --, therefor.

Column 106
Line 32, In Claim 1, "b'=2- 6," and insert -- b'=2-6, --, therefor.

Column 106
Line 35, In Claim 1, "—* ," and insert -- —*, --, therefor.

Column 106
Line 36, In Claim 1, "—* ," and insert -- —*, --, therefor.

Column 106
Line 41, In Claim 1, "or1" and insert -- or 1 --, therefor.